(12) United States Patent
Shinagawa et al.

(10) Patent No.: US 6,916,956 B2
(45) Date of Patent: Jul. 12, 2005

(54) CALCIUM RECEPTOR ANTAGONIST

(75) Inventors: Yuko Shinagawa, Takatsuki (JP);
Takeo Katsushima, Takatsuki (JP);
Takashi Nakagawa, Takatsuki (JP)

(73) Assignee: Japan Tobacco, Inc., Tokyo (JP)

( * ) Notice: Subject to any disclaimer, the term of this patent is extended or adjusted under 35 U.S.C. 154(b) by 122 days.

(21) Appl. No.: 10/344,157

(22) PCT Filed: Aug. 10, 2001

(86) PCT No.: PCT/JP01/06903
§ 371 (c)(1),
(2), (4) Date: Feb. 10, 2003

(87) PCT Pub. No.: WO02/14259
PCT Pub. Date: Feb. 21, 2002

(65) Prior Publication Data
US 2004/0006130 A1 Jan. 8, 2004

(30) Foreign Application Priority Data
Aug. 11, 2000 (JP) ........................................ 2000-244536
Apr. 27, 2001 (JP) ........................................ 2001-132879

(51) Int. Cl.$^7$ ................... C07C 217/10; C07D 213/30; C07D 33/16; C07D 307/42; C07D 277/24

(52) U.S. Cl. ........................ 564/88; 564/165; 564/220; 564/346; 562/451; 560/42; 549/58; 549/70; 549/71; 549/78; 549/491; 548/205; 546/334; 514/357; 514/365; 514/438; 514/433; 514/466; 514/471; 514/531

(58) Field of Search .................. 564/88, 165, 220, 564/346; 562/451; 560/42; 549/58, 70, 71, 78, 491; 548/205; 546/334; 514/357, 365, 438, 443, 466, 471, 531, 567, 604, 620, 630, 651

(56) References Cited

U.S. PATENT DOCUMENTS

| | | |
|---|---|---|
| 5,336,663 A | 8/1994 | Wenger et al. |
| 5,684,049 A | 11/1997 | Van Daele et al. |
| 5,856,576 A | 1/1999 | Harrington et al. |

FOREIGN PATENT DOCUMENTS

| | | |
|---|---|---|
| EP | 0 489 670 A1 | 6/1992 |
| EP | 0 542 685 A1 | 5/1993 |
| EP | 0 682 007 A1 | 11/1995 |
| EP | 0 852 224 A1 | 7/1998 |
| WO | WO 97/37967 A1 | 10/1997 |
| WO | WO 98/45255 A1 | 10/1998 |
| WO | WO 99/51241 A1 | 10/1999 |
| WO | WO 99/51569 A1 | 10/1999 |
| WO | WO 00/09132 A1 | 2/2000 |
| WO | WO 00/09491 A1 | 2/2000 |
| WO | WO 00/45816 A1 | 8/2000 |
| WO | WO 01/53254 A1 | 7/2001 |
| WO | WO 02/07673 A2 | 1/2002 |

OTHER PUBLICATIONS

Chem, abstr., vol. 88, (Columbus, Ohio, USA) p. 358, col. 2, abstract No. 62084 (f)m Ibanez et al., "New derivatives of 2–diphenylmethoxyethylamine with vasodilator and spasmolytic activity," *Eur. J. Med. Chem. Chim. Ther.*,1977, pp. 459–465 (Eng.).

Adams et al., "The Synthesis of New Bronchodilator Prodrugs," *Synthetic Communications,*1999, pp. 2419–2430, vol. 29, No. 14, Republic of South Africa.

Bect et al., "Preparation of Tetrahydrobenz[cd]indoles from 1–Tetralones," *J. Chem. Soc. Perkin Trans.*, 1990, pps. 689–693, United Kingdom.

Brown et al., "Cloning and Characterization of an Extracellular $Ca^{2+}$–Sensing Receptor from Bovine Parathyroid," *Nature*, Dec. 9, 1993, pps. 575–580, vol. 366, United States.

E.M. Brown, "Homeostatic Mechanisms Regulating Extracellular and Intracellular Calcium Metabolism," *The Parathyroids*, 1994, pps. 15–54, Chapter 2, United States.

Ejersted et al., "Human Parathyroid Hormone (1–34) and (1–84) Increase the Mechanical Strength and Thickness of Cortical Bone in Rats," *Journal of Bone and Mineral Research*, 1993, pps. 1097–1101, vol. 8, No. 9, United Kingdom.

(Continued)

*Primary Examiner*—Brian Davis
(74) *Attorney, Agent, or Firm*—Foley & Lardner LLP

(57) ABSTRACT

A compound of the formula [I]

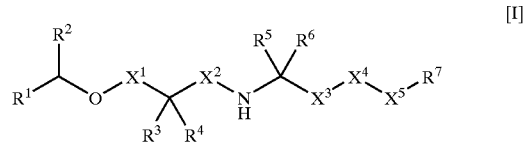

wherein $R^1$ is optionally substituted aryl group or optionally substituted heteroaryl group; $R^2$ is optionally substituted $C_{1-6}$ alkyl group, $C_{3-7}$ cycloalkyl group and the like; $R^3$ is hydrogen atom, $C_{1-6}$ alkyl group, hydroxyl group and the like; $R^4$ is hydrogen atom, $C_{1-6}$ alkyl group and the like; $R^5$ and $R^6$ are each $C_{1-6}$ alkyl group and the like; $R^7$ is optionally substituted aryl group or optionally substituted heteroaryl group; $X^1$, $X^2$ and $X^3$ are each $C_{1-6}$ alkylene group and the like; and $X^4$ and $X^5$ are each a single bond, methylene group and the like, a salt thereof, a solvate thereof or a prodrug thereof, and a pharmaceutical composition containing the compound, particularly a calcium receptor antagonist and a therapeutic agent for osteoporosis, are provided. The compound of the present invention is useful as a therapeutic drug of diseases accompanied by abnormal calcium homeostasis, or osteoporosis, hypoparathyreosis, osteosarcoma, periodontal disease, bone fracture, steoarthrosis, chronic rheumatoid arthritis, Paget's disease, humoral hypercalcemia, autosomal dominant hypocalcemia and the like.

In addition, an intermediate for the compound is provided.

16 Claims, 5 Drawing Sheets

OTHER PUBLICATIONS

Gowen et al., "Antagonizing the Parathyroid Calcium Receptor Stimulates Parathyroid Hormone Secretion and Bone Formation in Osteopenic Rats," *The Journal of Clinical Investigation*, 2000, pps. 1595–1604, vol. 105, No. 11, United States.

Ibanez et al., "New Derivatives of 2–Diphenylmethoxyethylamine with Vasodilator and Spasmolytic Activity," *Eur. J. Med. Chem.*, Sep.–Oct., 1977, pps. 459–462, No. 5, Spain.

J. Mizoguchi, "Effect of Intermittent Administration of hPTH Under a Hyperparathyroidism Condition in Male Rats," *Journal of Japanese Society of Bone Morphometry*, 1995, pps. 33–39, vol. 5, Japan.

Mosekilde et al., The Anabolic Effects of Human Parathyroid Hormond (hPTH) on Rat Vertebral Body Mass Are also Reflected in the Quality of Bone, Assessed by Biomechanical Testing: A Comparison Study Between hPTH–(1–34) and hPTH–(1–84), *Endocrinology*, 1991, pps. 421–428, vol. 129, No. 1, United States.

Scutt et al., "Time–Dependent Effects of Parathyroid Hormone and Prostaglandin $E_2$ on DNA Synthesis by Periosteal Cells From Embryonic Chick Calvaria," *Calcif Tissue Int.*, 1994, pps. 208–215, vol. 55, United States.

C.S. Tam et al., "Parathyroid Hormone Stimulates the Bone Apposition Rate Independently of Its Resorptive Action: Differential Effects of Intermittent and Continuous Administration," *Endocrinology*, 1982, pps. 506–512, vol. 110, No. 2, United States.

T. Uzawa et al., "Comparison of the Effects of Intermittent and Continuous Administration of Human Parathyroid Hormone (1–34) on Rat Bone," *Elsevier*, Apr. 1995, pps. 477–484, vol. 16, No. 4, Japan.

T. J. Wronski et al., "Anabolic Effects of Parathyroid Hormone on Cortical Bone in Ovariectomized Rats," *Pergamon*, 1994, pps. 51–58, vol. 15, No. 1, United States.

T. J. Wronski et al., "Parathyroid Hormone is More Effective Than Estrogen or Bisphosphonates for Restoration of Lost Bone Mass in Ovariectomized Rats," *Endocrinology*, pps. 823–831, vol. 132, No. 2, United States.

Xu et al., "Relation Between Radioprotection and Estrogenic Effect of Nonsteroidal Estrogens," (Chem. abstr. vol. 95 (1984) (Columbus Ohio USA) p. 112 abs. No. 969j).

Kibe et al., "Effects of Taurine on Metabolism of Cholesterol–Bile Acid in Rabbit," (Chem. abstr. vol. 95 (1981) (Columbus Ohio USA) p. 112 abs. No. 970c).

Padawer et al., "Combined Treatment with Radiostradiol-Lucanthone in Mouse C3HBA Mammary Adenocarcinoma and With Estradiol–Lucanthone in an Estrogen Bioassay," (Chem. abstr. vol. 95 (1981) (Columbus Ohio USA) p. 112 abs. No. 971d).

R. Takao et al., "Effects of Human PTH(1–34) On Bone Metabolism In Rats (Fifth Report): Efficacy Of Once Weekly Administration In Normal Rats," Japanese Journal of Bone Metabolism, 1994, p. S343, vol. 12 (Suppl.), Japan.

Chem, abstr. vol. 88, (1978), (Columbus, Ohio, USA), p. 358, column 2, abstract No. 62084 (f)m IBANEZ et al., "New derivatives of 2–diphenylmethoxyethylamine with vasodilator and spasmolytic activity," *Eur. J. Med. Chem. Chim. Ther.*, 1977, pp. 459–465 (Eng.).

CALCIUM RECEPTOR ANTAGONIST

This application is a 371 of PCT/JP01/06903 filed Aug. 10, 2001

TECHNICAL FIELD

The present invention relates to a compound having a calcium-sensing receptor (CaSR, hereinafter to be simply referred to as a calcium receptor) antagonistic action, a pharmaceutical composition containing the compound, particularly a calcium receptor antagonist and a therapeutic agent of osteoporosis, and to an intermediate compound useful for synthesizing the compound.

BACKGROUND ART

Calcium receptors sense extracellular $Ca^{2+}$ concentration and increase intracellular $Ca^{2+}$, thereby suppressing the production of parathyroid hormone (PTH) involved in the control of $Ca^{2+}$ metabolism and bone metabolism.

The serum calcium concentration of healthy mammal is strictly maintained at about 9–10 mg/100 ml (ca. 2.5 mM), which is referred to as calcium homeostasis of living organisms. When this value falls to not more than 50%, tetania occurs, and when it increases by 50%, consciousness is clouded, both cases threatening the lives. For maintaining calcium homeostasis, duodenum acts as a $Ca^{2+}$ uptake organ, bone acts as a $Ca^{2+}$ storage organ, and kidney acts as a $Ca^{2+}$ excretory organ. These $Ca^{2+}$ kinetics are controlled by various hormones generally referred to as "calcium controlling hormone". Representative hormone includes active vitamin D [$1_\alpha$, $25(OH)_2D_3$], PTH, calcitonin, Parathyroid Hormone-Related Protein (PTH-related Protein (PTHrP)) and the like.

Bone plays an important role not only as a supporting framework and motor organ of the body, but also as a storage organ of $Ca^{2+}$, which is its constituent component. To fulfill such functions, bone tissues repeat formation thereof (osteogenesis) and absorption thereof (bone resorption) throughout the entire life. For osteogenesis, osteoblast derived from mesenchymal cell plays a major role, and for bone resorption, osteoclast derived from hematopoietic cell plays a major role. Osteogenesis is a mechanism including osteoid formation by bone organic matrix (bone matrix proteins such as type I collagen and the like) produced by osteoblast present on the osteogenesis surface, and subsequent calcification. Bone resorption is a mechanism including adhesion of osteoclast to the bone surface, intracellular absorption of $Ca^{2+}$ via acid secretion and ion transport, and excretion of absorbed $Ca^{2+}$ to the bone marrow side, thereby releasing $Ca^{2+}$ into blood. The deficient part of the bone absorbed by osteoclast is repaired by osteogenesis by osteoblast. This series of phenomena are called remodeling of bone, and by the remodeling, old bones are replaced by new bones, thus maintaining the strength of the entire bone while maintaining calcium homeostasis.

PTH is a hormone that plays a key role in maintaining the calcium homeostasis. When blood $Ca^{2+}$ concentration decreases, secretion of PTH from the parathyroid gland is promoted immediately, which, in the bone, acts on osteoblast (activation of osteoclast by osteoblast, production of bone organic matrix decomposition enzyme and the like) to promote osteoclastic bone resorption, whereby $Ca^{2+}$ is transferred from the bone into the blood. In kidney, PTH promotes resorption of $Ca^{2+}$ in the distal convulted tubule, and activates 25(OH) vitamin $D_3$ in the proximal tubule, thereby promoting the production of active vitamin $D_3$ [$1_\alpha$, $25(OH)_2D_3$] having a function of promoting resorption of $Ca^{2+}$ from the intestine. It also suppresses resorption of phosphorus As mentioned above, PTH directly or indirectly increases blood $Ca^{2+}$ concentration.

When blood $Ca^{2+}$ concentration increases, calcium receptor senses it, immediately suppresses secretion of PTH from the parathyroid gland to decrease the amount of $Ca^{2+}$ to be supplied into the blood [Brown, E. M., Homeostatic mechanisms regulating extracellular and intracellular calcium metabolism, in the parathyroids, p.19, (1994), Raven press, New York]. Secretion of PTH is also suppressed by active vitamin D [$1_\alpha$, $25(OH)_2D_3$].

Because PTH is a hormone assuming an important role in controlling $Ca^{2+}$ metabolism and bone metabolism, attempts have been made to apply PTH to the treatment of osteoporosis. In 1982, Tam et al. found that sustained administration of bovine PTH (1-84) to thyroid/parathyroid gland enucleated rat results in promotion of both osteogenesis and bone resorption of femoral cancellous bone, leading to a decrease in net bone mass, but subcutaneous intermittent administration thereof does not result in promotion of bone resorption but in promotion of osteogenesis alone, leading to an increase in the bone mass [Endocrinology, 110, 506–512 (1982)]. Furthermore, Uzawa et al. compared the actions of sustained administration and intermittent administration of PTH with regard to epiphysial long bone and metaphysial cancellous bone of young rat. As a result, they clarified that sustained-administration of PTH results in remarkable increase in bone mass in metaphysial cancellous bone highly susceptible to the effect of enchondral ossification, though associated with abnormal findings such as hyperplasia of epiphysial plate cartilage, fibrous ostitis and the like, and in marked promotion of bone resorption and decrease in bone mass accompanied by rarefaction of cortical bone, in epiphysial cancellous bone where the effect is small [Bone, 16, 477–484 (1995)]. In addition, it has been reported that intermittent administration of PTH results in significant increases in bone mass and bone trabecula in both epiphysial and metaphysial cancellous bones without increase in osteoclast or decrease of cortical bone.

Moreover, Scutt et al. have reported that, in chicken calvaria derived osteoblast, a short time (10–20 min) treatment with PTH promotes cell growth as compared to a long time (18 hr) treatment [Calcif. Tissue Int., 55, 208–215 (1994)]. This suggests that some of the actions of PTH on osteoblast are temporary and that expression of the action by the treatment for an extremely short time may be related to the fact that sustained administration and intermittent administration of PTH in vivo show different actions on bone tissues.

Ishizuya et al. further clarified through investigation of the action of PTH on differentiation of osteoblast using an in vitro experiment system that the action of PTH varies depending on the treatment time. They have reported that sustained action of PTH on osteoblast derived from rat calvaria resulted in strong inhibition of differentiation of osteoblast and nearly complete inhibition of osteogenesis in vitro, but repeated PTH action for the first 6 hr of 48 hr as one cycle resulted in significant promotion of differentiation of osteoblast and promotion of osteogenesis in vitro.

PTH is considered to not only prevent decrease in bone mass of osteoporosis model, but also has a bone mass recovery effect even on an animal already suffering from marked decrease in bone mass. Wronski et al. intermittently administered human PTH (1-34) to 90-day-old SD rat at 4 weeks post-ovariectomy and showing an obvious decrease in cancellous bone, for 15 weeks from 4 weeks postovariectomy. As a result, promotion of osteogenesis and inhibition of bone resorption were observed during the period of from week 5 to week 10 after the start of the administration, showing increased bone mass of about twice the bone mass of sham operation group [Endocrinology, 132, 823–831 (1993)]. They have also reported that, in this experiment, estrogen and bisphosphonate prevented decrease in bone mass caused by ovariectomy but did not show increase in bone mass, unlike PTH. They detailedly analyzed the cortical bone of this experiment system and found images showing promoted osteogenesis and bone mass increase on the periost side and endosteum side by intermittent administration of human PTH (1-34), based on which they have clarified that the increase in cancellous bone due to PTH did not accompany decrease in cortical bone [Bone, 15, 51–58 (1994)].

Furthermore, Mosekilde et al. have reported that intermittent administration of human PTH (1-34) or human PTH (1-84) causes not only an increase in bone mass but also a dose-dependent increase in compression strength and bending strength, which are indices of bone substance, of cancellous bone [Endocrinology, 129, 421–428 (1991)] and cortical bone [J. Bone Miner. Res., 8, 1097–1101 (1993)] of rat vertebral bone. As discussed above, since PTH shows an obvious bone mass increasing action in experimental animals, various investigations are ongoing as regards the restrictive conditions expected in actual clinical applications. Mizoguchi studied whether or not a pharmacological effect is observed by intermittent administration of PTH, even when PTH in blood, which is considered to be one of the factors responsible for osteoporosis, has significantly increased, and concluded that the bone mass increased as usual [Journal of Japanese Society of Bone Morphometry, vol. 5, pp. 33–39 (1995)]. Takao et al. have studied the frequency of PTH administration and reported that administration of once a week for 12 weeks to healthy rat scarcely promoted bone absorption but dose-dependently increased the bone mass [Japanese Journal of Bone Metabolism, vol. 12 (Suppl.), p. S343 (1994)], suggesting possible effectiveness of clinically useful low frequency administration. The foregoing achievements suggest the possibility of PTH for making a potent and promising therapeutic drug for the treatment of postmenopausal osteoporosis or postovariectomy osteoporosis, which increases bone mass and decreases bone fracture rate.

These results clearly indicate that intermittent administration of PTH would enable treatment of osteoporosis. On the other hand, PTH problematically requires injection as an administration route, which is painful for many patients. However, an orally administrable pharmaceutical agent that can intermittently increase PTH concentration in blood is greatly expected to become a therapeutic drug of osteoporosis, which is based on a new action mechanism different from that of the above-mentioned PTH and conventional calcitonin.

Calcium receptor is a G protein coupled receptor, which is cloned as a molecule essential for controlling PTH secretion, and which penetrates cell membrane 7 times. Human calcium receptor consists of 1078 amino acids, and shows 93% amino acid homology with bovine calcium receptor. Human calcium receptor consists of a large N terminal extracellular region consisting of 612 amino acids, a cell membrane penetration region consisting of 250 amino acids and a C terminal intracellular region consisting of 216 amino acids.

Expression of calcium receptor has been found in parathyroid gland, kidney, thyroid C cell, brain and the like, as well as in bone (bone marrow cells).

When calcium receptor is bound with a ligand such as $Ca^{2+}$ and the like, it activates phospholipase C in conjugation with G protein, causes production of inositol triphosphate and increase in intracellular $Ca^{2+}$ concentration, and as a result, suppresses secretion of PTH [Nature, 366, 575–580 (1993)].

As mentioned above, a pharmaceutical agent that inhibits activation of calcium receptor, or a pharmaceutical agent that antagonizes calcium receptor, removes suppression of PTH secretion in parathyroid gland cells, and promotes secretion of PTH. If the antagonistic action can increase blood PTH concentration discontinuously and intermittently, its antagonist is expected to show the same effect as provided by intermittent administration of PTH, and a pharmaceutical agent extremely effective for the treatment of osteoporosis is considered to be provided.

As a CaSR antagonist, international publication WO99/51569 describes a compound of the following formula

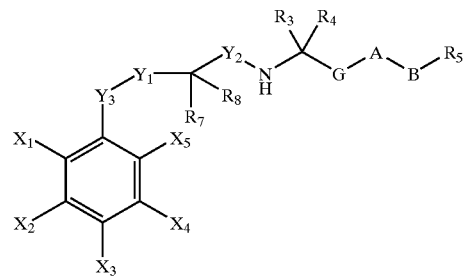

wherein
$Y_1$ is a covalent bond, alkylene or alkenylene of up to 4 carbon atoms, unsubstituted or substituted by $C_{1-4}$ alkyl, or O;
$Y_2$ is methylene, unsubstituted or substituted by $C_{1-4}$ alkyl or haloalkyl;
$Y_3$ is a covalent bond or O, S, N—$R^{IV}$ or $C_{1-4}$ alkylene-O, $C_{1-4}$ alkylene-S, $C_{1-4}$ alkylene-N—$R^{IV}$;
$R_3$ and $R_4$ are, independently, methyl or ethyl, or, together, form cyclopropyl;
$R_5$ is aryl or fused aryl, dihydro or tetrahydro fused aryl, unsubstituted or substituted with any substituents being selected from the group consisting of OH, halogen, $C_{1-4}$ alkyl, $C_{1-4}$ alkoxy, $C_{3-6}$ cycloalkyl, $OSO_2R^{IV}$, CN, $NO_2$, $OCF_3$, $CF_3$, $CH_2CF_3$, $(CH_2)_nCO_2R^{IV}$, and O—$(CH_2)_nCO_2R^{IV}$, wherein n is an integer from 0 to 3 and $R^{IV}$ is selected from the group consisting of H, $C_{1-4}$ alkyl, and $C_{3-6}$ cycloalkyl;
or $R_5$ is heteroaryl or fused heteroaryl; wherein the heteroring contains N, O or S, and is aromatic, dihydro or tetrahydro, unsubstituted or substituted with any substituents being selected from the group consisting of OH, $OCH_3$, $CH(CH_3)_2$, halogen, $C_{1-4}$ alkyl, $C_{1-4}$ alkoxy, $C_{3-6}$ cycloalkyl, $OSO_2R^{IV}$, CN, $NO_2$, $OCF_3$, $CF_3$, $CH_2CF_3$, $(CH_2)_nCO_2H$, $(CH_2)_nCO_2R^{IV}$, and O—$(CH_2)_nCO_2R^{IV}$;
G is a covalent bond, $CHR_6$ or C—$R_6$, wherein $R_6$ is H, OH or O (forming a ketone);
$R_7$ is H, OH, or O—$C_{1-4}$ alkyl;
$R_8$ is H or $C_{1-4}$ alkyl; or $R_7$ and $R_8$ together form a ketone;
A and B are, independently, selected from the group consisting of a bond, $CH_2$, NH, O, S and C=O, provided that A or B is selected from $CH_2$ and NH; or A and B together form a bond; or the A-B moiety is represented by CH=CH or C≡C;
wherein
$X_1$ and $X_5$ are independently selected from the group consisting of H, halogen, CN, $NO_2$, $C_{1-4}$ alkyl, cycloalkyl, $CH_2$-aryl, and $CH_2$-heteroaryl; provided that either $X_1$ or $X_5$ is H;

$X_2$, $X_3$ and $X_4$ are selected from the group consisting of H, halogen, O—$C_{1-4}$ alkyl, O-aryl, O-heteroaryl, $CH_2$-aryl, $CH_2$-heteroaryl, alkyl, C(O)aryl, C(O)heteroaryl CH(OH)aryl, CH(OH)heteroaryl and J-K;

J is a covalent bond, alkylene, O-alkylene or alkenylene of up to 5 carbon atoms, unsubstituted or substituted by a substituent selected from the group consisting of $C_{1-4}$ alkyl, OH, O(forming a ketone), aryl, heteroaryl, and NR'R", wherein R' and R" are independently selected from the group consisting of H, alkyl, aryl, heteroaryl, C(O)alkyl, C(O)aryl, and C(O)heteroaryl;

K is selected from the group consisting of $CO_2R^{IV}$, OH, and CN; and pharmaceutically acceptable salts and complexes thereof.

Particularly, a compound of the formula wherein $Y_3$ is $C_{1-4}$ alkylene-O

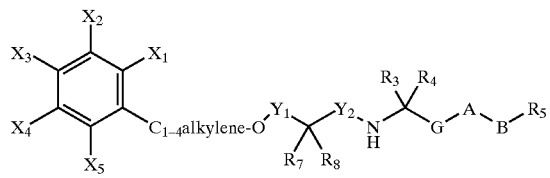

is suggested, though not directly described. In this case, however, "$C_{1-4}$ alkylene" means a straight chain, and the branched chain such as in the present invention is not described or suggested.

In addition, international publication WO99/51241 describes, as a CaSR antagonist, a compound of the following formula

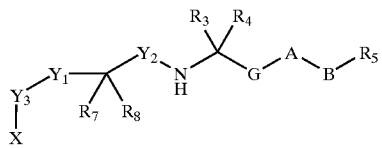

wherein $Y_1$ is a covalent bond, alkylene or alkenylene of up to 4 carbon atoms, unsubstituted or substituted by $C_{1-4}$ alkyl or O;

$Y_2$ is methylene, unsubstituted or substituted by $C_{1-4}$ alkyl or haloalkyl;

$Y_3$ is covalent bond or selected from the group consisting of O, S, N—$R^{IV}$, $C_{1-4}$ alkylene-O, $C_{1-4}$ alkylene-S, and $C_{1-4}$ alkylene-N—$R^{IV}$;

$R^{IV}$ is selected from the group consisting of H, $C_{1-4}$ alkyl, and $C_{3-6}$ cycloalkyl;

$R_3$ and $R_4$ are, independently, methyl or ethyl, or, together, form cyclopropyl;

$R_5$ is heteroaryl or fused heteroaryl; wherein the hetero-ring contains N, O or S, and is aromatic, dihydro or tetrahydro, unsubstituted or substituted with any substituents being selected from the group consisting of OH, $OCH_3$, $CH(CH_3)_2$, halogen, $C_{1-4}$ alkyl, $C_{1-4}$ alkoxy, $C_{3-6}$ cycloalkyl, $OSO_2R^{IV}$, CN, $NO_2$, $OCF_3$, $CF_3$, $CH_2CF_3$, $(CH_2)_nCO_2H$, $(CH_2)_nCO_2R^{IV}$, and O—$(CH_2)_nCO_2R^{IV}$;

n is an integer of from 0 to 3;

G is a covalent bond, $CHR_6$ or C—$R_6$, wherein $R_6$ is H, OH or O (forming a ketone);

$R_7$ is H, OH, or O—$C_{1-4}$ alkyl;

$R_8$ is H or $C_{1-4}$ alkyl; or $R_7$ and $R_8$ together form a ketone;

A and B are, independently, selected from the group consisting of a bond, $CH_2$, NH, O, S and C=O, provided that either A or B is selected from $CH_2$ and NH; or A and B together form a bond;

or A-B moiety is represented by CH=CH or C≡C;

X is selected from sub formulas (Ia) to (Ie) hereinbelow:

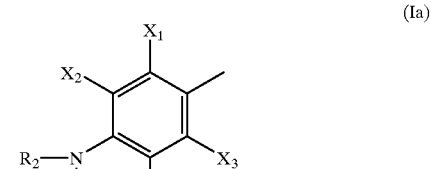

(Ia)

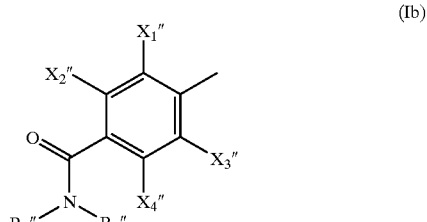

(Ib)

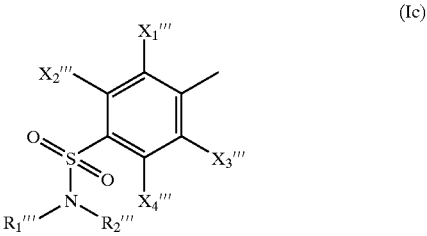

(Ic)

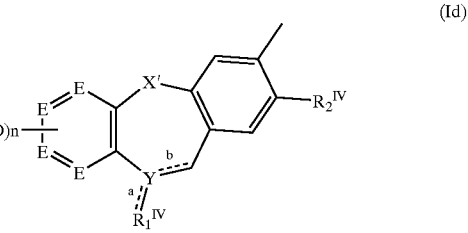

(Id)

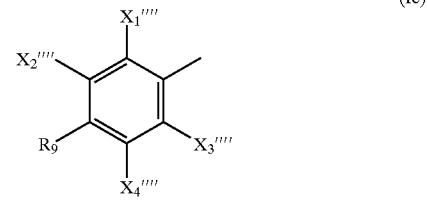

(Ie)

wherein

W is selected from the group consisting of $R_1$, $SO_2R_1$, $C(O)R_1$, $SO_2NR_1R_1'$, $C(O)NR_1R_1'$, $C(O)OR_1$, and $SO_3R_1'$, wherein $R_1$ and $R_1'$ are independently selected from the group consisting of hydrogen, $C_{1-4}$ alkyl, $C_{3-6}$ cycloalkyl, $C_{2-5}$ alkenyl, $C_{2-5}$ alkynyl, heterocycloalkyl, aryl and aryl $C_{1-4}$ alkyl; or $R_1$ and $R_1'$ together form a 3 to 7 membered optionally substituted heterocyclic ring; wherein any substituents are selected from the group consisting of CN, aryl, $CO_2R$, $CO_2NHR$, OH, OR, $NH_2$, halo, $CF_3$, $OCF_3$ and $NO_2$; wherein R represents $C_{1-4}$ alkyl, or $C_{3-6}$ cycloalkyl;

$X_1$ is selected from the group consisting of CN, $NO_2$, Cl, F, Br, I, H, R', OR', $CF_3$, $OCF_3$ and $OSO_2R'$, wherein R' represents $C_{1-4}$ alkyl, or $C_{3-6}$ cycloalkyl;

$X_2$, $X_3$ and $X_4$ are, independently, selected from the group consisting of CN, $NO_2$, Cl, F, Br, I, H, R", OR", $CF_3$, $OCF_3$ and $OSO_2R"$, provided that either $X_1$ or $X_3$ is H, wherein R" is $C_{1-4}$ alkyl or haloalkyl; or $X_1$ and $X_2$ together form an aryl or heteroaryl ring, substituted or unsubstituted; wherein the heteroatom is selected from N, S and O; and any substituents are selected from the group consisting of halo, $C_{1-4}$ alkyl,
$OCF_3$, $CF_3$, OMe, CN, $OSO_2R'$ and $NO_2$; or $X_3$ and $X_4$ independently represent $C(O)R_1$; and $R_2$ is selected from the group consisting of hydrogen, $C_{1-4}$ alkyl, $C_{3-6}$ cycloalkyl, $C_{2-5}$ alkenyl, $C_{2-5}$ alkynyl, heterocycloalkyl, aryl and aryl-$C_{1-4}$ alkyl;

$X_1"$ is selected from the group consisting of CN, $NO_2$, Cl, F, Br, I, H, R, OR, $CF_3$, $OCF_3$ and $OSO_2R$, wherein R represents $C_{1-4}$ alkyl, or $C_{3-6}$ cycloalkyl;

$X_2"$, $X_3"$ and $X_4"$ are, independently, selected from the group consisting of CN, $NO_2$, CO, F, Br, I, H, R', OR', $CF_3$, $OCF_3$ and $OSO_2R'$, provided that either $X_1"$ or $X_3"$ is H, wherein R' is $C_{1-4}$ alkyl or haloalkyl; or $X_1"$ and $X_2"$ together form an aryl or heteroaryl ring, substituted or unsubstituted, wherein the heteroatom is selected from N, S and O and any substituents are selected from the group consisting of halo, $C_{1-4}$ alkyl, $OCF_3$, $CF_3$, OMe, CN, $OSO_2$—$C_{1-4}$ alkyl, $OSO_2$—$C_{3-6}$ cycloalkyl and $NO_2$;

or $X_3"$ and $X_4"$ independently represent $C(O)R_1$; and $R_1"$ and $R_2"$ are, independently, selected from the group consisting of hydrogen, $C_{1-4}$ alkyl, $C_{3-6}$ cycloalkyl, $C_{2-5}$ alkenyl, $C_{2-5}$ alkynyl, heterocycloalkyl and aryl; or $R_1"$ and $R_2"$ together form a 3 to 7 membered optionally substituted heterocyclic ring; wherein any substituents are selected from the group consisting of CN, aryl, $CO_2R"$, $CO_2NHR"$, OH, OR", $NH_2$, halo, $CF_3$, $OCF_3$ and $NO_2$;
wherein R" represents $C_{1-4}$ alkyl, or $C_{3-6}$ cycloalkyl;

$X_1"'$ is selected from the group consisting of CN, $NO_2$, Cl, F, Br, I, H, R, OR, $CF_3$, $OCF_3$ and $OSO_2R$, wherein R represents $C_{1-4}$ alkyl, or $C_{3-6}$ cycloalkyl;

$X_2"'$, $X_3"'$ and $X_4"'$ are, independently, selected from the group consisting of CN, $NO_2$, Cl, F, Br, I, H, R', OR', $CF_3$, $OCF_3$ and $OSO_2R'$, provided that either $X_1"'$ or $X_3"'$ is H, wherein R' is $C_{1-4}$ alkyl or haloalkyl;

or $X_1"'$ and $X_2"'$ together form an aryl or heteroaryl ring, substituted or unsubstituted; wherein the heteroatom is selected from N, S and O and the substituents are selected from the group consisting of halo, $C_{1-4}$ alkyl $OCF_3$, $CF_3$, OMe, CN, $OSO_2$—$C_{1-4}$ alkyl, $OSO_2$—$C_{3-6}$ cycloalkyl and $NO_2$;

or $X_3"'$ and $X_4"'$ independently represent $C(O)R_1$;

$R_1"'$ and $R_2"'$ are, independently, selected from the group consisting of hydrogen, $C_{1-4}$ alkyl, $C_{3-6}$ cycloalkyl, $C_{2-5}$ alkenyl, $C_{2-5}$ alkynyl, heterocycloalkyl and aryl; or $R_1"'$ and $R_2"'$ together form a 3 to 7 membered optionally substituted heterocyclic ring; wherein any substituents are selected from the group consisting of CN, aryl, $CO_2R"$, $CO_2NHR"$, OH, OR", $NH_2$, halo, $CF_3$, $OCF_3$ and $NO_2$; wherein R" represents $C_{1-4}$ alkyl, or $C_{3-6}$ cycloalkyl;

D is selected from the group consisting of H, CN, $NO_2$, Cl, F, Br, I, R, OR, SR, $CF_3$, $OCF_3$ and $OSO_2R$, wherein R represents $C_{1-4}$ alkyl, $C_{3-6}$ cycloalkyl, or $C_{1-10}$ aryl or heteroaryl wherein the heteroatom is selected from N, S and O and substituents are selected from the group consisting of halo, $C_{1-4}$ alkyl, $OCF_3$, $CF_3$, OMe, CN, $OSO_2$—$C_{1-4}$ alkyl, $OSO_2$—$C_{3-6}$ cycloalkyl and $NO_2$;

n is the integer of 1 or 2;

each E is independently C or N, provided that less than two E moieties is N; further provided that when n is 2, each E is C;

a and b are optionally present bonds;

$R_1^{IV}$ is selected from the group consisting of $(CH_2)_nCO_2R'$, $(CH_2)_nCO_2H$, $(CH_2)_nCONR'_2$, $(CH_2)_nCH_2OR'$, OR', SR', CN, $NO_2$, Cl, F, BR, I, H, $CF_3$, $OCF_3$, $OSO_2R'$, R' and H; wherein R' is $C_{1-4}$ alkyl, or $C_{3-6}$ cycloalkyl;

or $R_1^{IV}$ is O, forming a ketone such that $YR_1^{IV}$ represents —C=O;

$R_2^{IV}$ is selected from the group consisting of hydrogen, CN, $NO_2$, Cl, F, Br, I, H, R", OR", $CF_3$, $OCF_3$, and $OSO_2R"$; wherein R" represents $C_{1-4}$ alkyl, or $C_{3-6}$ cycloalkyl.

Y is selected from the group consisting of C, CH, O, N and S;

provided that when Y is S, $R_1^{IV}$ is O or not present; further provided that when Y is O, $R_1^{IV}$ is not present;

X' is $CH_2$, NH, O and S.

$R_9$ is O-alkyl, O—$CH_2$-aryl, and O-aryl;

$X_1""$ is selected from the group consisting of CN, $NO_2$, Cl, F, Br, I, H, R, OR, $CF_3$, $OCF_3$ and $OSO_2R$, wherein R represents $C_{1-4}$ alkyl, or $C_{3-6}$ cycloalkyl;

$X_2""$, $X_3""$, and $X_4""$ are, independently, selected from the group consisting of CN, $NO_2$, Cl, F, Br, I, H, R', OR', $CF_3$, $OCF_3$ and $OSO_2R'$, provided that either $X""_1$ or $X"'_3$ is H, wherein R' is $C_{1-4}$ alkyl or haloalkyl;

or $X_1""$ and $X_2""$ together form an aryl or heteroaryl ring, substituted or unsubstituted; wherein the heteroatom is selected from N, S and O and the substituents are selected from the group consisting of halo, $C_{1-4}$ alkyl, $OCF_3$, $CF_3$, OMe, CN, $OSO_2$—$C_{1-4}$ alkyl, $OSO_2$—$C_{3-6}$ cycloalkyl and $NO_2$;

or $X_3""$ and $X_4""$ independently represent $C(O)R_1$:

and pharmaceutically acceptable salts and complex thereof.

Again, a compound of the formula wherein $Y_3$ is $C_{1-4}$ alkylene-O

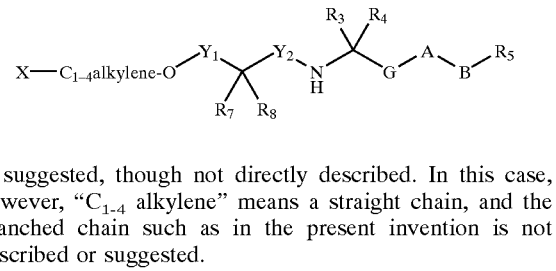

is suggested, though not directly described. In this case, however, "$C_{1-4}$ alkylene" means a straight chain, and the branched chain such as in the present invention is not described or suggested.

International publication WO98/45255 (EP-A-973730) also describes a compound of the following formula as a CaSR antagonist

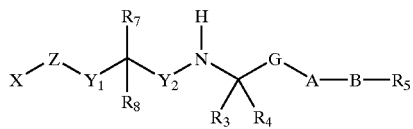

wherein $Y_1$ is a covalent bond, alkylene or alkenylene of up to 4 carbon atoms, unsubstituted or substituted by $C_{1-4}$ alkyl;

$Y_2$ is methylene, unsubstituted or substituted by $C_{1-4}$ alkyl or $CF_3$;

Z is selected from the group consisting of a covalent bond, O, S, NH, N—$C_{1-4}$ alkyl, $O(CH_2)_n$, $(CH_2)_nO$, NR'"C=O and C=ONR'", where R'" is $C_{1-4}$ alkyl and n is an integer from 1 to 3, $R_3$ and $R_4$ are, independently, methyl or ethyl, or, together, form cyclopropyl;

$R_5$ is phenyl or naphthyl, unsubstituted or substituted with one or more substituents selected from the group consisting of OH, $C_{1-4}$ alkyl $CH(CH_3)_2$, halo, halo $C_{1-4}$ alkyl, $C_{1-4}$ alkoxy, $C_{3-6}$ cycloalkyl, $OSO_2R^{IV}$, CN, $NO_2$, $OCF_3$, $CF_3$ and $CH_2CF_3$, wherein $R^{IV}$ represents $C_{1-4}$ alkyl or $C_{3-6}$ cycloalkyl;

G is a covalent bond or C—R$_6$ wherein R$_6$ is H, OH or O (forming a carbonyl moiety);
R$_7$ is H, OH, or O—C$_{1-4}$ alkyl;
R$_8$ is H or C$_{1-4}$ alkyl; or R$_7$ and R$_8$ together form a carbonyl moiety;
the A-B moiety is represented by CH$_2$CH$_2$, a covalent bond, —CH=CH— or —C≡C—; and
X is selected from the group consisting of sub formulae (Ia), (Ib), (Ic), (Id) and (Ie) hereinbelow:

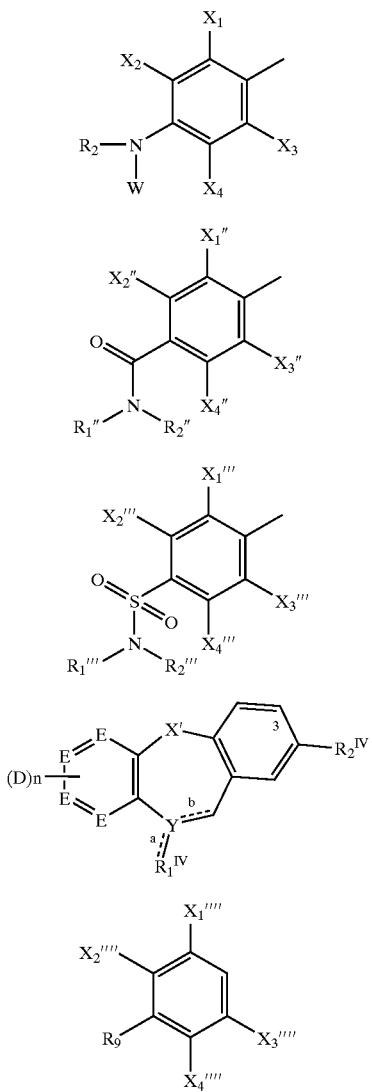

wherein
in sub formula (Ia):
W is selected from the group consisting of R$_1$, SO$_2$R$_1$, C(O)R$_1$, SO$_2$NR$_1$R$_1$', C(O)NR$_1$R$_1$' and C(O)OR$_1$SO$_3$R$_1$', wherein R$_1$ and R$_1$' are independently selected from the group consisting of hydrogen, C$_{1-4}$ alkyl, C$_{3-6}$ cycloalkyl, C$_{2-5}$ alkenyl, C$_{2-5}$ alkynyl, heterocycloalkyl aryl and aryl C$_{1-4}$ alkyl; or R$_1$ and R$_1$' together form a 3- to 7-membered optionally substituted heterocyclic ring; wherein any substituents are selected from the group consisting of CN, aryl, CO$_2$R, CO$_2$NHR, OH, OR, NH$_2$, halo, CF$_3$, OCF$_3$ and NO$_2$; wherein R represents C$_{1-4}$ alkyl, or C$_{3-6}$ cycloalkyl;
X$_1$ is selected from the group consisting of CN, NO$_2$, Cl, F, Br, I, H, R', OR', CF$_3$, OCF$_3$ and OSO$_2$R', wherein R' represents C$_{1-4}$ alkyl, or C$_{3-6}$ cycloalkyl;

X$_2$, X$_3$ and X$_4$ are, independently, selected from the group consisting of CN, NO$_2$, Cl, F, Br, I, H, R", OR", CF$_3$, OCF$_3$ and OSO$_2$R", wherein R" is C$_{1-4}$ alkyl or haloalkyl; or X$_1$ and X$_2$ together form an aryl or heteroaryl ring, substituted or unsubstituted; wherein the heteroatom is selected from N, S and O; and any substituents are selected from the group consisting of halo, C$_{1-4}$ alkyl, OCF$_3$, CF$_3$, OMe, CN, OSO$_2$R' and NO$_2$; or X$_3$ and X$_4$ independently represent C(O)R$_1$;
provided that when there are multiple halo substitutions in the haloalkyl, halo represents F; also provide that either X$_1$ or X$_3$ is hydrogen; and
R$_2$ is selected from the group consisting of hydrogen, C$_{1-4}$ alkyl, C$_{3-6}$ cycloalkyl, C$_{2-5}$ alkenyl, C$_{2-5}$ alkynyl, heterocycloalkyl aryl and aryl-C$_{1-4}$ alkyl;
in sub formula (Ib):
X$_1$" is selected from the group consisting of CN, NO$_2$, Cl, F, Br, I, H, R, OR, CF$_3$, OCF$_3$ and OSO$_2$R, wherein R represents C$_{1-4}$ alkyl, or C$_{3-6}$ cycloalkyl;
X$_2$", X$_3$" and X$_4$" are, independently, selected from the group consisting of CN, NO$_2$, Cl, F, Br, I, H, R', OR', CF$_3$, OCF$_3$ and OSO$_2$R', wherein R' is C$_{1-4}$ alkyl or haloalkyl; provided that when there are multiple halo substitutions in the haloalkyl, halo represents F, or X$_1$" and X$_2$" together form an aryl or heteroaryl ring, substituted or unsubstituted; wherein the heteroatom is selected form N, S and O and any substituents are selected from the group consisting of halo, C$_{1-4}$ alkyl, OCF$_3$, CF$_3$, OMe, CN, OSO$_2$—C$_{1-4}$ alkyl, OSO$_2$—C$_{3-6}$ cycloalkyl and NO$_2$;
or X$_3$" and X$_4$" independently represent C(O)R$_1$;
provided that either X$_1$" or X$_3$" is hydrogen; and
R$_1$" and R$_2$" are, independently, selected from the group consisting of hydrogen, C$_{1-4}$ alkyl, C$_{3-6}$ cycloalkyl, C$_{2-5}$ alkenyl, C$_{2-5}$ alkynyl, heterocycloalkyl and aryl; or R$_1$" and R$_2$" together form a 3 to 7 membered optionally substituted heterocyclic ring; optionally containing an additional heteroatom selected from O, S and N; wherein any substituents are selected from the group consisting of CN, aryl, CO$_2$R", CO$_2$NHR", OH, OR", NH$_2$, halo, CF$_3$, OCF$_3$ and NO$_2$; wherein R" represents C$_{1-4}$ alkyl, or C$_{3-6}$ cycloalkyl;
in sub formula (Ic):
X$_1$'" is selected from the group consisting of CN, NO$_2$, Cl, F, Br, I, H, R, OR, CF$_3$, OCF$_3$ and OSO$_2$R, wherein R represents C$_{1-4}$ alkyl, or C$_{3-6}$ cycloalkyl;
X$_2$'", X$_3$'" and X$_4$'" are, independently, selected from the group consisting of CN, NO$_2$, Cl, F, Br, I, H, R', OR', CF$_3$, OCF$_3$ and OSO$_2$R', wherein R' is C$_{1-4}$ alkyl or haloalkyl; provided that when there are multiple halo substitutions in the haloalkyl, halo represents F; or X$_1$'" and X$_2$'" together form an aryl or heteroaryl ring, substituted or unsubstituted; wherein the heteroatom is selected from N, S and O and the substituents are selected from the group consisting of halo, C$_{1-4}$ alkyl, OCF$_3$, CF$_3$, OMe, CN, OSO$_2$—C$_{1-4}$ alkyl, OSO$_2$—C$_{3-6}$ cycloalkyl and NO$_2$; or
X$_3$'" and X$_4$'" independently represent C(O)R$_1$;
provided that either X$_1$'" or X$_3$'" represents H; and
R$_1$'" and R$_2$'" are, independently, selected from the group consisting of hydrogen, C$_{1-4}$ alkyl, C$_{3-6}$ cycloalkyl, C$_{2-5}$ alkenyl, C$_{2-5}$ alkynyl, heterocycloalkyl and aryl; or R$_1$'" and R$_2$'" together form a 3 to 7 membered optionally substituted heterocyclic ring optionally containing an additional heteroatom selected from O, S and N; wherein the substituents are selected from the group consisting of CN, aryl, CO$_2$R", CO$_2$NHR", OH, OR", NH$_2$, halo, CF$_3$, OCF$_3$ and NO$_2$; wherein R" represents C$_{1-4}$ alkyl, or C$_{3-6}$ cycloalkyl;

in sub formula (Id):
D is selected from the group consisting of CN, $NO_2$, Cl, F, Br, I, R, OR, SR, $CF_3$, $OCF_3$ and $OSO_2R$, wherein R represents $C_{1-4}$ alkyl, $C_{3-6}$ cycloalkyl, or $C_{1-10}$ aryl or heteroaryl wherein the heteroatom is selected from N, S and O and substituents are selected from the group consisting of halo, $C_{1-4}$ alkyl, $OCF_3$, $CF_3$, OMe, CN, $OSO_2$—$C_{1-4}$ alkyl, $OSO_2$—$C_{3-6}$ cycloalkyl and $NO_2$;
n is the integer of 1 or 2;
each E is independently C or N, provided that no more than two E moieties are N;
further provided that when n is 2, each E is C;
a and b are optionally present bond;
$R_1^{IV}$ is selected from the group consisting of $(CH_2)_nCO_2R'$, $(CH_2)_nCO_2H$, $(CH_2)_nCONR'_2$, $(CH_2)_nCH_2OR'$, OR', SR', CN, $NO_2$, Cl, F, Br, I, $CF_3$, $OCF_3$, $OSO_2R'$, R' and H; wherein R' is $C_{1-4}$ alkyl, or $C_{3-6}$ cycloalkyl;
or $R_1^{IV}$ is O forming a ketone such that $YR_1^{IV}$ represents —C═O;
$R_2^{IV}$ is selected from the group consisting of hydrogen, CN, $NO_2$, Cl, F, Br, I, H, R", OR", $CF_3$, $OCF_3$, and $OSO_2R$"; wherein R" represents $C_{1-4}$ alkyl, or $C_{3-6}$ cycloalkyl.
Y is selected from C, CH, O, N and S; provided that when Y is S, $R_1^{IV}$ is O; further provided that when Y is O, $R_1^{IV}$ is not present;
X' is $CH_2$, NH, O and S; and
attachment is at the carbon atom marked 3;
in sub formula (Ie):
$X_1''''$ is selected from the group consisting of CN, $NO_2$, Cl, F, Br, I, H, R', OR', $CF_3$, $OCF_3$ and $OSO_2R'$, wherein R' represents $C_{1-4}$ alkyl, or $C_{3-6}$ cycloalkyl;
$X_2''''$, $X_3''''$ and $X_4''''$ are, independently, selected from the group consisting of CN, $NO_2$, Cl, F, Br, I, H, R", OR", $CF_3$, $OCF_3$ and $OSO_2R$", wherein R" is $C_{1-4}$ alkyl or haloalkyl; or $X_1''''$ and $X_2''''$ together form an aryl or heteroaryl ring, substituted or unsubstituted; wherein the heteroatom is selected from N, S and O; and any substituents are selected from the group consisting of halo, $C_{1-4}$ alkyl, $OCF_3$, $CF_3$, OMe, CN, $OSO_2R'$ and $NO_2$; or $X_3''''$ and $X_4''''$ independently represent $C(O)R_1$;
provided that when there are multiple halo substitutions in the haloalkyl, halo represents F; also provided that either $X_1''''$ or $X_3''''$ is hydrogen;
and $R_9$ is O—$CH_2$-alkyl, O—$CH_2$-aryl and O-aryl.

In addition, Japanese Patent Application under PCT laid-open under kohyo No. 2001-501584 (WO97/37967, EP-A-901459, U.S. Pat. No. 6,022,894) also describes a compound of the following formula as a CaSR antagonist.

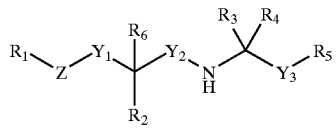

wherein
$R_1$ is selected from the group consisting of aryl, longer-length alk, and cycloalk;
$R_2$ is selected from the group consisting of lower alk, cycloalk, alkoxy, H, OH, ═O, C(O)OH, C(O)O-lower alk, C(O)NH-lower alk, C(O)N(lower alk)$_2$, SH, S-lower alk, $NH_2$, NH-lower alk, and N(lower alk)$_2$;
$R_3$ and $R_4$ is each independently lower alk or together cyclopropyl;
$R_5$ is either an optionally substituted naphthyl having 1–4 substituents independently selected from the group consisting of methyl, ethyl, isopropyl, methoxy, Cl, F, Br, and lower haloalkoxy, or a substituted phenyl having 1–4 substituents with at least one substituent in a meta or para position selected from the group consisting of lower alkyl, methoxy, Cl, F, Br, and lower haloalkoxy, provided that said substituted phenyl may also have 2 or 3 additional substituents;
$R_6$ if present is either hydrogen, lower alkyl or lower alkenyl, wherein $R_6$ is not present if $R_2$ is ═O;
$Y_1$ is either a covalent bond, alkylene or alkenylene;
$Y_2$ is alkylene;
$Y_3$ is alkylene; and
Z is selected from the group consisting of a covalent bond, O, S, NH, N-lower alk, alkylene, alkenylene, and alkynylene, provided that if Z is O, S, NH, or N-lower alk, then $Y_1$ is not a covalent bond; further provided that $Y_1$ and Z may together form a covalent bond;
provided that $R_1$ is not 6-CN-2-pyridyl;
further provided that if $R_5$ is 3,4-dimethoxy-phenyl, then $R_1$ is not $CH_3(CH_2)_5$O-phenyl; 2-cyclopentyl-phenyl; 2-Cl-phenyl; 2-CN-phenyl; 2-(3-furanyl)phenyl; or 4-(1,2-benzisothiazole);
further provided that if $R_5$ is 4-methoxy-phenyl, then $R_1$ is not 2-cyclopentyl-phenyl; 2-$CH_3$-phenyl; 2-benzyl-phenyl; 3-$CH_3$, 4-$CH_3SO_2$-phenyl; 4-(1,2-benzisothiazole);
further provided that if $R_5$ is 4-Cl-phenyl, then $R_1$ is not 2-$CH_3$-phenyl; 5-iso-propyl-phenyl; 2-$CH_3$-phenyl; 4-$CH_3$-phenyl; phenyl; 2-Cl-phenyl; 4-Cl-phenyl; 2-methoxy; 4-$CH_3$CHCH-phenyl; 3,4$CH_3$-phenyl; 2,4$CH_3$-phenyl; 2,3$CH_3$-phenyl; 2-iso-propyl; 5-$CH_3$-phenyl; pyridyl; 1-imidazole; or 4-(1,2-benzisothiazole); and
further provided that if $R_5$ is 3,5-dimethyl, or 4-methoxy-phenyl, then $R_1$ is not 4-$CH_3$, 6-CN-2-pyridyl; or thiophenecarboxamide; and pharmaceutical acceptable salts and complexes thereof; wherein said compound has an $IC_{50} \leq 10$ $\mu$M using the Calcium Receptor Inhibitor Assay.

Maxine Gowen et al. examined the effect of a compound having a CaSR antagonistic action and called NPS-2143

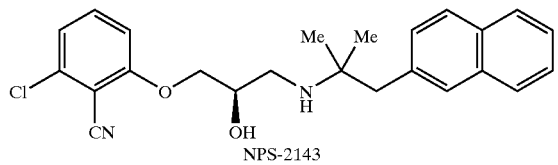

NPS-2143 on osteogenesis by orally administering NPS-2143 to OVX rat and measuring the concentration in blood and bone density, and reported the results [J. Clin. Invest., 105, 1595–1604 (2000)].

According to this publication, NPS-2143 significantly promotes release of PTH, but has no direct effect on osteoblast and osteoclast in vitro, as a result of which no bone increase or decrease was found. One of the reasons was considered to be the too long half-life of NPS-2143 in blood. When rat PTH (1-34) was administered to OVX rat at a dose of 5 $\mu$g/kg, the PTH concentration in blood shows a peak at about 175 pg/ml in 30 min, and restores its original level in 2 hr. When NPS-2143 was administered at a dose of 100 $\mu$mol/kg, PTH concentration kept increasing even after the PTH concentration in blood reached about 115 pg/ml in 30 min, and the concentration was about 140 pg/ml even after 4 hr [see J. Clin. Invest., 105, 1595–1604 (2000), p. 1598, FIG. 3].

At this time, the concentration in blood of NPS-2143 itself remained above 100 ng/ml even at 8 hr after administration and it was only after 24 hr when the concentration became not more than 10 ng/ml and could not be detected.

The reference of the above-mentioned Maxine Gowen et al. suggests that a calcium receptor antagonist having a too long half-life in blood brings about the same results as in sustained administration of PTH and teaches that an increase in the bone mass cannot be expected.

The present invention aims at providing a compound having a calcium receptor antagonistic action. The present invention also aims at providing a pharmaceutical composition comprising said compound, which is effective as an agent for the treatment of a disease showing abnormal calcium homeostasis, namely, osteoporosis, hypoparathyreosis, osteosarcoma, periodontal disease, bone fracture, steoarthrosis, chronic rheumatoid arthritis, Paget's disease, humoral hypercalcemia, autosomal dominant hypocalcemia and the like, particularly as a therapeutic agent for osteoporosis, which is capable of oral administration and intermittent administration. Moreover, the present invention aims at providing a synthetic intermediate for a compound having a calcium receptor antagonistic action.

DISCLOSURE OF THE INVENTION

The present inventors have conducted intensive studies in an attempt to solve the above-mentioned problems and as a result, found that a compound of the following formula [I] has a superior calcium receptor antagonistic action and can be administered orally and intermittently, which resulted in the completion of the present invention. All the conventionally known calcium receptor antagonists increase PTH concentration in blood in a sustained manner and a sufficient osteogenesis promoting action cannot be expected. In contrast, the compound of the following formula is surprisingly capable of increasing the PTH concentration in blood intermittently in a non-sustained manner, and is expected to be put into practical use as a superior therapeutic agent for osteoporosis.

The compound represented by the following formula of the present invention is characterized by its structure wherein carbon atom adjacent to oxygen atom has $R^1$ and $R^2$ as substituents, i.e.,

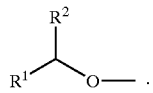

As is clear from the Experimental Example below, the compound of the present invention having the structure

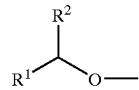

has not only a superior calcium receptor antagonistic action, but a temporary non-sustained PTH secretion promoting action, as compared to conventional compounds having the structure

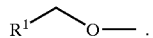

Accordingly, it is considered that, by administration of the compound of the present invention, an effect similar to that obtained by intermittent administration of PTH is obtained, which is extremely effective for the treatment of osteoporosis.

Accordingly, the present invention relates to a compound represented by the following formula, a calcium receptor antagonist and a therapeutic agent for osteoporosis, which contains the compound as an active ingredient, and an intermediate compound useful for the synthesis of the compound. More particularly, the present invention provides the following (1) to (21)

(1) A compound of the formula [I]

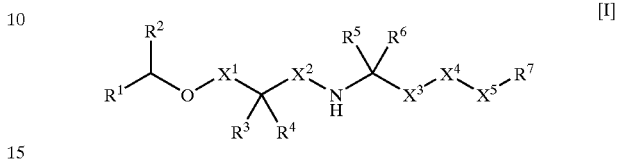

wherein
$R^1$ is aryl group or heteroaryl group wherein said aryl group and heteroaryl group are optionally substituted by 1 to 3 substituents selected from halogen atom, $C_{1-6}$ alkyl group, halo($C_{1-6}$)alkyl group, hydroxy($C_{1-6}$)alkyl group, $C_{1-6}$ alkoxy($C_{1-6}$)alkyl group, hydroxyl group, $C_{1-6}$ alkoxy group, halo($C_{1-6}$)alkoxy group, mercapto group, $C_{1-6}$ alkylthio group, $C_{1-6}$ alkylsulfanyl group, $C_{1-6}$ alkylsulfonyl group, aminosulfonyl group, $C_{1-6}$ alkylsulfamoyl group, di($C_{1-6}$)alkylsulfamoyl group, carboxy group, ($C_{1-6}$ alkoxy)carbonyl group, $C_{1-7}$ acyl group, carbamoyl group, ($C_{1-6}$ alkyl)carbamoyl group, di($C_{1-6}$ alkyl) carbamoyl group, cyano group, nitro group, amino group, $C_{1-6}$ alkylamino group, di($C_{1-6}$)alkylamino group, $C_{1-7}$ acylamino group, $C_{1-3}$ alkylenedioxy group,

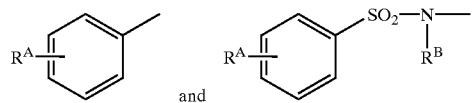

wherein $R^A$ is ($C_{1-6}$ alkoxy)carbonyl group or carboxy group, and $R^B$ is hydrogen atom or $C_{1-6}$ alkyl group;

$R^2$ is $C_{1-6}$ alkyl group
wherein said $C_{1-6}$ alkyl group is optionally substituted by 1 to 3 substituents selected from halogen atom, hydroxyl group, $C_{1-6}$ alkoxy group, carboxy group, amino group, $C_{1-6}$ alkylamino group, di($C_{1-6}$) alkylamino group and oxo group, $C_{3-7}$ cycloalkyl group, $C_{2-6}$ alkenyl group, $C_{2-6}$ alkynyl group, aralkyl group, carboxy group, ($C_{1-6}$ alkoxy)carbonyl group or cyano group;

$R^3$ is hydrogen atom, $C_{1-6}$ alkyl group, hydroxyl group, $C_{1-6}$ alkoxy group, mercapto group, $C_{1-6}$ alkylthio group, carboxy group, ($C_{1-6}$ alkoxy)carbonyl group, ($C_{1-6}$ alkyl) carbamoyl group, di($C_{1-6}$ alkyl)carbamoyl group, amino group, $C_{1-6}$ alkylamino group or di($C_{1-6}$)alkylamino group;

$R^4$ is hydrogen atom, $C_{1-6}$ alkyl group or $C_{2-6}$ alkenyl group, or $R^3$ and $R^4$ in combination show oxo group;

$R^5$ and $R^6$ are the same or different and each is $C_{1-6}$ alkyl group or $R^5$ and $R^6$ in combination show cyclopropyl group together with the carbon atom they bind to;

$R^7$ is aryl group or heteroaryl group wherein said aryl group and heteroaryl group are optionally substituted by 1 to 3 substituents selected from halogen atom, $C_{1-6}$ alkyl group, halo($C_{1-6}$)alkyl group, hydroxy($C_{1-6}$)alkyl group, $C_{3-7}$ cycloalkyl group, hydroxyl group, $C_{1-6}$ alkoxy group, halo($C_{1-6}$)alkoxy group, carboxy group, ($C_{1-6}$ alkoxy) carbonyl group, nitro group, cyano group, $C_{1-6}$ alkylsulfonyloxy group, carbamoyl group and $C_{1-3}$ alkylenedioxy group;

$X^1$ is a single bond, $C_{1-6}$ alkylene group or $C_{2-6}$ alkynylene group wherein said $C_{1-6}$ alkylene group and $C_{2-6}$ alkynylene group are optionally substituted by $C_{1-6}$ alkyl group or oxo group;

$X^2$ is $C_{1-6}$ alkylene group wherein said $C_{1-6}$ alkylene group is optionally substituted by $C_{1-6}$ alkyl group or halo($C_{1-6}$)alkyl group;

$X^3$ is a single bond or $C_{1-6}$ alkylene group wherein said $C_{1-6}$ alkylene group is optionally substituted by hydroxyl group or oxo group;

$X^4$ and $X^5$ in combination show a single bond, methylene group, —NH—, oxygen atom, sulfur atom, —C(=O)—, —CH$_2$NH—, —CH$_2$O—, —CH$_2$S—, —CH$_2$CO—, —NHCH$_2$—, —OCH$_2$—, —SCH$_2$—, —COCH$_2$—, —CH=CH— or —C≡C— (hereinafter sometimes to be referred to as compound [I]), a salt thereof, a solvate thereof or a prodrug thereof.

(2) A compound of the formula [I']

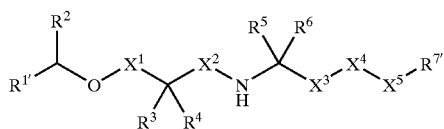

[I']

wherein $R^{1'}$ is aryl group or heteroaryl group wherein said aryl group and heteroaryl group are optionally substituted by 1 to 3 substituents selected from halogen atom, $C_{1-6}$ alkyl group, halo($C_{1-6}$)alkyl group, hydroxy($C_{1-6}$)alkyl group, $C_{1-6}$ alkoxy($C_{1-6}$)alkyl group, hydroxyl group, $C_{1-6}$ alkoxy group, halo($C_{1-6}$)alkoxy group, mercapto group, $C_{1-6}$ alkylthio group, $C_{1-6}$ alkylsulfanyl group, $C_{1-6}$ alkylsulfonyl group, aminosulfonyl group, $C_{1-6}$ alkylsulfamoyl group, di($C_{1-6}$)alkylsulfamoyl group, carboxy group, ($C_{1-6}$ alkoxy)carbonyl group, $C_{1-7}$ acyl group, carbamoyl group, ($C_{1-6}$ alkyl)carbamoyl group, di($C_{1-6}$ alkyl)carbamoyl group, cyano group, nitro group, amino group, $C_{1-6}$ alkylamino group, di($C_{1-6}$)alkylamino group and $C_{1-7}$ acylamino group;

$R^{7'}$ is aryl group or heteroaryl group wherein said aryl group and heteroaryl group are optionally substituted by 1 to 3 substituents selected from halogen atom, $C_{1-6}$ alkyl group, halo($C_{1-6}$)alkyl group, $C_{3-6}$ cycloalkyl group, hydroxyl group, $C_{1-6}$ alkoxy group, halo($C_{1-6}$)alkoxy group, carboxy group, ($C_{1-6}$ alkoxy)carbonyl group, nitro group, cyano group and $C_{1-6}$ alkylsulfonyloxy group; and $R^2$, $R^3$, $R^4$, $R^5$, $R^6$, $X^1$, $X^2$, $X^3$, $X^4$ and $X^5$ are same as defined above in (1) (hereinafter sometimes to be referred to as compound [I']) respectively, a salt thereof, a solvate thereof or a prodrug thereof.

(3) A compound of the formula [I"]

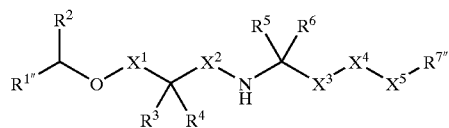

[I"]

wherein $R^{1''}$ is aryl group or heteroaryl group wherein said aryl group and heteroaryl group are optionally substituted by 1 to 3 substituents selected from $C_{1-3}$ alkylenedioxy group,

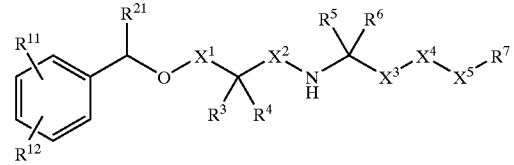

and wherein $R^A$ is ($C_{1-6}$ alkoxy)carbonyl group or carboxy group and $R^B$ is hydrogen atom or $C_{1-6}$ alkyl group;

$R^{7''}$ is aryl group or heteroaryl group wherein said aryl group and heteroaryl group are optionally substituted by 1 to 3 substituents selected from hydroxy $C_{1-6}$ alkyl group, carbamoyl group and $C_{1-3}$ alkylenedioxy group; and $R^2$, $R^3$, $R^4$, $R^5$, $R^6$, $X^1$, $X^2$, $X^3$, $X^4$ and $X^5$ are same as defined above (1) (hereinafter sometimes to be referred to as compound [I"]) respectively, a salt thereof, a solvate thereof or a prodrug thereof.

(4) A compound of the formula [I-2]

[I-2]

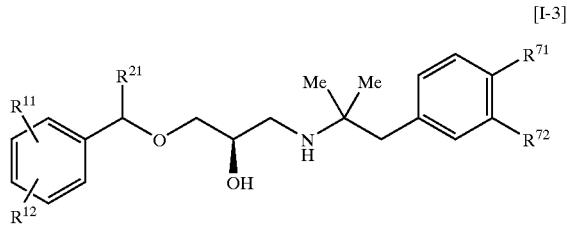

wherein $R^{11}$ and $R^{12}$ are the same or different and each is hydrogen atom, halogen atom, $C_{1-4}$ alkyl group, hydroxy($C_{1-6}$)alkyl group, $C_{1-6}$ alkoxy($C_{1-6}$)alkyl group, hydroxyl group, $C_{1-4}$ alkoxy group, cyano group or nitro group, or $R^{11}$ and $R^{12}$ in combination show $C_{1-3}$ alkylenedioxy group;

$R^{21}$ is $C_{1-4}$ alkyl group
wherein said alkyl group is optionally substituted by $C_{1-4}$ alkoxy group,
$C_{3-5}$ cycloalkyl group, $C_{2-4}$ alkenyl group, or aralkyl group; and $R^3$, $R^4$, $R^5$, $R^6$, $R^7$, $X^1$, $X^2$, $X^3$, $X^4$ and $X^5$ are same as defined above (1)(hereinafter sometimes to be referred to as compound [I-2]) respectively, a salt thereof, a solvate thereof or a prodrug thereof.

(5) The compound of the above-mentioned (4), which is represented by the formula [I-3]

[I-3]

wherein $R^{71}$ and $R^{72}$ are the same or different and each is hydrogen atom, $C_{1-4}$ alkyl group or $C_{1-4}$ alkoxy group, or in combination show —CH=CH—CH=CH— or $C_{1-3}$ alkylenedioxy group, and $R^{11}$, $R^{12}$ and $R^{21}$ are same as defined in the above-mentioned (4) (hereinafter sometimes to be referred to as compound [I-3]) respectively, a salt thereof, a solvate thereof or a prodrug thereof.

(6) The compound of the above-mentioned (5) wherein $R^{11}$ and $R^{12}$ are the same or different and each is hydrogen atom, chlorine atom, methyl group, hydroxymethyl group, hydroxyl group, methoxy group, cyano group or nitro group, or $R^{11}$ and $R^{12}$ in combination show methylenedioxy group, and $R^{21}$ is optionally branched $C_{1-4}$ alkyl group or $C_{3-5}$ cycloalkyl group, a salt thereof, a solvate thereof or a prodrug thereof.

(7) The compound of the above-mentioned (6), wherein $R^{21}$ is methyl group, ethyl group, cyclopropyl group or cyclobutyl group, a salt thereof, a solvate thereof or a prodrug thereof.

(8) The compound of the above-mentioned (7), wherein $R^{11}$ is hydrogen atom, $R^{12}$ is methyl group, methoxy group or hydroxymethyl group, or $R^{11}$ and $R^{12}$ in combination show methylenedioxy group, and $R^{21}$ is methyl group or cyclopropyl group, a salt thereof, a solvate thereof or a prodrug thereof.

(9) The compound of the above-mentioned (8), wherein $R^{21}$ is cyclopropyl group, a salt thereof, a solvate thereof or a prodrug thereof.

(10) The compound of the above-mentioned (9), wherein $R^{71}$ and $R^{72}$ in combination show —CH=CH—CH=CH—, a salt thereof, a solvate thereof or a prodrug thereof.

(11) The compound of the above-mentioned (9), wherein $R^{71}$ and $R^{72}$ are groups selected from $C_{1-4}$ alkyl group and $C_{1-4}$ alkoxy group, a salt thereof, a solvate thereof or a prodrug thereof.

(12) The compound of the above-mentioned (1), which is selected from (2R)-1-[1,1-dimethyl-2-(naphthalen-2-yl)ethylamino]-3-[(cyclopropyl)(2-methoxyphenyl)methoxy]propan-2-ol, (2R)-1-[1,1-dimethyl-2-(naphthalen-2-yl)ethylamino]-3-[(cyclopropyl)(2-methylphenyl)methoxy]propan-2-ol, (2R)-1-[1,1-dimethyl-2-(naphthalen-2-yl)ethylamino]-3-[(cyclopropyl)(phenyl)methoxy]propan-2-ol, (2R)-1-[1,1-dimethyl-2-(naphthalen-2-yl)ethylamino]-3-[1-(2-methoxyphenyl)ethoxy]propan-2-ol, (2R)-1-[1,1-dimethyl-2-(naphthalen-2-yl)ethylamino]-3-[1-(2-methylphenyl)ethoxy]propan-2-ol, (2R)-1-[1,1-dimethyl-2-(naphthalen-2-yl)ethylamino]-3-[1-(2-methoxyphenyl)propoxy]propan-2-ol, (2R)-1-[1,1-dimethyl-2-(naphthalen-2-yl)ethylamino]-3-[1-(2-cyanophenyl)ethoxy]propan-2-ol, (2R)-1-[1,1-dimethyl-2-(naphthalen-2-yl)ethylamino]-3-[1-(3-methoxyphenyl)ethoxy]propan-2-ol and (2R)-1-[1,1-dimethyl-2-(naphthalen-2-yl)ethylamino]-3-[1-(3-methylphenyl)ethoxy]propan-2-ol, a salt thereof, a solvate thereof or a prodrug thereof.

(13) (2R)-1-[1,1-Dimethyl-2-(naphthalen-2-yl)ethylamino]-3-[(cyclopropyl)(2-hydroxymethylphenyl)methoxy]propan-2-ol, a salt thereof, a solvate thereof or a prodrug thereof.

(14) A pharmaceutical composition comprising the compound of any of the above-mentioned (1) to (13), a salt thereof, a solvate thereof or a prodrug thereof as an active ingredient.

(15) A calcium receptor antagonist comprising the compound of any of the above-mentioned (1) to (13), a salt thereof, a solvate thereof or a prodrug thereof as an active ingredient.

(16) A therapeutic agent for osteoporosis comprising the compound of any of the above-mentioned (1) to (13), a salt thereof, a solvate thereof or a prodrug thereof as an active ingredient.

(17) A compound of the formula [II]

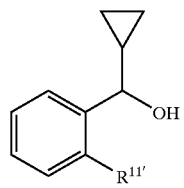

wherein $R^{11'}$ is halogen atom, $C_{1-4}$ alkyl group, hydroxy($C_{1-6}$)alkyl group, $C_{1-6}$ alkoxy($C_{1-6}$)alkyl group, hydroxyl group, $C_{1-4}$ alkoxy group, tert-butyldimethylsilyloxymethyl group, cyano group or nitro group (hereinafter sometimes to be referred to as compound [II]), a salt thereof or a solvate thereof.

(18) The compound of the above-mentioned (17), wherein, in the formula [II], $R^{11'}$ is $C_{1-4}$ alkyl group, hydroxy($C_{1-6}$)alkyl group or $C_{1-4}$ alkoxy group, a salt thereof or a solvate thereof.

(19) A compound of the formula [III]

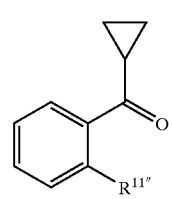

wherein $R^{11''}$ is halogen atom, hydroxy($C_{1-6}$)alkyl group, $C_{1-6}$ alkoxy($C_{1-6}$)alkyl group, hydroxyl group, $C_{1-4}$ alkoxy group, tert-butyldimethylsilyloxymethyl group, cyano group or nitro group (hereinafter sometimes to be referred to as compound [III]), a salt thereof or a solvate thereof.

(20) The compound of the above-mentioned (19), wherein, in the formula [III], $R^{11''}$ is $C_{1-4}$ alkoxy group, a salt thereof or a solvate thereof.

(21) A compound of the formula [IV]

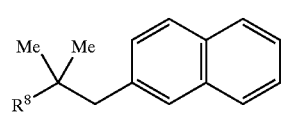

wherein $R^8$ is carboxy group, nitro group, tert-butoxycarbonylamino group or benzyloxycarbonylamino group (hereinafter sometimes to be referred to as compound [IV]), a salt thereof or a solvate thereof.

EMBODIMENT OF THE INVENTION

Figure 1:
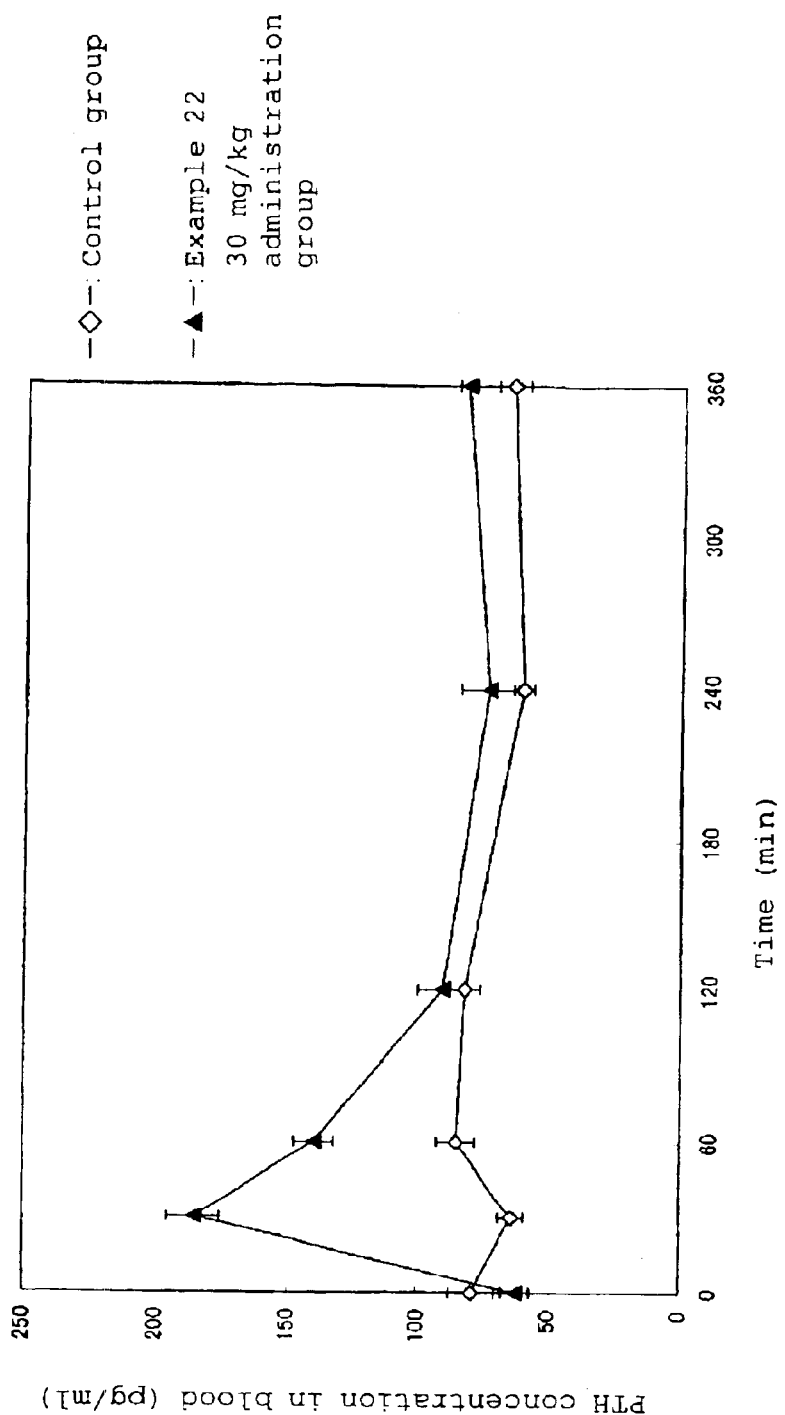
FIG. 1 shows the time-course changes of serum PTH concentration when 30 mg/kg of a compound of Example 22 was administered to rat.

The terms used in the present specification are defined in the following.

The "aryl group" is aromatic hydrocarbon group having 6 to 12 carbon atoms, which may be partly saturated. Examples thereof include phenyl group, biphenyl group, indenyl group, naphthyl and the like. Preferred are phenyl group and naphthyl group, and particularly preferred is phenyl group. These aryl groups are optionally substituted by the substituents to be mentioned later. The position of the bond of these aryl groups and the position of the substituent when substituted are not particularly limited as long as they are chemically acceptable.

The "heteroaryl group" shows a 5-membered to 6-membered unsaturated ring containing 1 to 3 heteroatoms in the ring, which is selected from nitrogen atom, oxygen atom and sulfur atom, including a fused ring with a benzene ring or other hetero ring. Examples of these heteroaryl groups include pyrrolyl group, furyl group, thienyl group, imidazolyl group, oxazolyl group, thiazolyl group, pyrazolyl group, isooxazolyl group, isothiazolyl group, oxadiazolyl group, triazolyl group, indolyl group, benzofuryl group, benzothienyl group, benzimidazolyl group, benzoxazolyl group, benzothiazolyl group, pyridyl group, pyrimidinyl group, quinolyl group, isoquinolyl group and the like. Preferred are benzofuryl group, benzothienyl group, benzimidazolyl group, benzoxazolyl group, benzothiazolyl group, pyridyl group and quinolyl group. These heteroaryl groups may be substituted by the substituents to be mentioned later. The position of the bond of these heteroaryl groups and the position of the substituent when substituted are not particularly limited as long as they are chemically acceptable.

The "halogen atom" is fluorine atom, chlorine atom, bromine atom or iodine atom, preferably fluorine atom and chlorine atom, and particularly preferably chlorine atom.

The "$C_{1-6}$ alkyl group" is linear or branched chain alkyl group having 1 to 6, preferably 1 to 4, carbon atoms, and is exemplified by methyl group, ethyl group, propyl group, isopropyl group, butyl group, isobutyl group, tert-butyl group, pentyl group, isopentyl group, tert-pentyl group, hexyl group and the like, with preference given to $C_{1-4}$ alkyl group selected from methyl group, ethyl group, propyl group, isopropyl group, butyl group, isobutyl group and tert-butyl group.

The "halo($C_{1-6}$)alkyl group" is haloalkyl group wherein the aforementioned "$C_{1-6}$ alkyl group" is substituted by one or more halogen atoms. The position of the substituent is not particularly limited as long as it is chemically acceptable. Examples of "halo($C_{1-6}$)alkyl group" include fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, 2-fluoroethyl group, 2,2-difluoroethyl group, 2,2,2-trifluoroethyl group, 2-chloroethyl group, 2,2-dichloroethyl group, 2,2,2-trichloroethyl group, 2-bromoethyl group, 2,2-dibromoethyl group, 2,2,2-tribromoethyl group, 3-chloropropyl group, 4-chlorobutyl group and the like, with preference given to halo($C_{1-2}$)alkyl group such as trifluoromethyl group and 2,2,2-trichloroethyl group.

The "hydroxy($C_{1-6}$)alkyl group" is hydroxyalkyl group wherein the aforementioned "$C_{1-6}$ alkyl group" is substituted by hydroxyl group. The position of the substituent is not particularly limited as long as it is chemically acceptable. Examples of "hydroxy($C_{1-6}$)alkyl group" include hydroxymethyl group, 1-hydroxyethyl group, 2-hydroxyethyl group, 1-hydroxypropyl group, 2-hydroxypropyl group, 3-hydroxypropyl group, 2-hydroxy-1-methylethyl group, 1-hydroxybutyl group, 2-hydroxybutyl group, 3-hydroxybutyl group, 4-hydroxybutyl group, 3-hydroxy-2-methylpropyl group, 2-hydroxy-1,1-dimethylethyl group, 5-hydroxypentyl group, 6-hydroxyhexyl group and the like, with preference given to hydroxy $C_{1-4}$ alkyl group selected from hydroxymethyl group, 2-hydroxyethyl group, 3-hydroxypropyl group and 4-hydroxybutyl group.

The "$C_{1-6}$ alkoxy group" is linear or branched chain alkoxy group having 1 to 6, preferably 1 to 4, carbon atoms. Examples thereof include methoxy group, ethoxy group, propoxy group, isopropoxy group, butoxy group, tert-butoxy group, pentyloxy group, tert-pentyloxy group, hexyloxy group and the like, with preference given to $C_{1-4}$ alkoxy group selected from methoxy group, ethoxy group, propoxy group, isopropoxy group, butoxy group and tert-butoxy group.

The "$C_{1-6}$ alkoxy($C_{1-6}$)alkyl group" is alkoxyalkyl group herein the aforementioned "$C_{1-6}$ alkyl group" is substituted by the aforementioned "$C_{1-6}$ alkoxy group". The position of the substituent is not particularly limited as long as it is chemically acceptable. Examples of "$C_{1-6}$ alkoxy($C_{1-6}$)alkyl group" include methoxymethyl group, ethoxymethyl group, propoxymethyl group, butoxymethyl group, pentyloxymethyl group, hexyloxymethyl group, 1-methoxyethyl group, 1-ethoxyethyl group, 2-methoxyethyl group, 2-ethoxyethyl group, 1-methoxypropyl group, 1-ethoxypropyl group, 2-methoxypropyl group, 2-ethoxypropyl group, 3-methoxypropyl group, 3-ethoxypropyl group, 2-methoxy-1-methylethyl group, 1-methoxybutyl group, 1-ethoxybutyl group, 2-methoxybutyl group, 2-ethoxybutyl group, 3-methoxybutyl group, 3-ethoxybutyl group, 4-methoxybutyl group, 4-ethoxybutyl group, 3-methoxy-2-methylpropyl group, 2-methoxy-1,1-dimethylethyl group, 2-ethoxy-1,1-dimethylethyl group, 5-methoxypentyl group, 6-methoxyhexyl group and the like, with preference given to $C_{1-4}$ alkoxy($C_{1-4}$)alkyl group selected from methoxymethyl group, ethoxymethyl group, propoxymethyl group, butoxymethyl group, 2-methoxyethyl group, 3-methoxypropyl group and 4-methoxybutyl group.

The "halo($C_{1-6}$)alkoxy group" is haloalkoxy group wherein the aforementioned "$C_{1-6}$ alkoxy group" is substituted by one or more halogen atoms. The position of the substituent is not particularly limited as long as it is chemically acceptable. Examples of "halo($C_{1-6}$)alkoxy group" include fluoromethoxy group, difluoromethoxy group, trifluoromethoxy group, chloromethoxy group, dichloromethoxy group, trichloromethoxy group, bromomethoxy group,-dibromomethoxy group, tribromomethoxy group, iodomethoxy group, diiodomethoxy group, triiodomethoxy group, 2-fluoroethoxy group, 2,2-difluoroethoxy group, 2,2,2-trifluoroethoxy group, 2-chloroethoxy group, 2,2-dichloroethoxy group, 2,2,2-trichloroethoxy group, 2-bromoethoxy group, 2,2-dibromoethoxy group, 2,2,2-tribromoethoxy group, 3-chloropropoxy group, 4-chlorobutoxy group and the like, with preference given to halo($C_{1-2}$)alkoxy group such as trifluoromethoxy group and 2,2,2-trichloroethoxy group.

The "$C_{1-6}$ alkylthio group" is a linear or branched chain alkylthio group having 1 to 6, preferably 1 to 4, carbon atoms. Examples thereof include methylthio group; ethylthio group, propylthio group, isopropylthio group, butylthio group, tert-butylthio group, pentylthio group, tert-pentylthio group, hexylthio group and the like, with preference given to $C_{1-4}$ alkylthio group selected from methylthio group, ethylthio group, propylthio group, isopropylthio group, butylthio group and tert-butylthio group.

The "$C_{1-6}$ alkylsulfanyl group" is linear or branched chain alkylsulfanyl group having 1 to 6 carbon atoms. Examples thereof include methylsulfanyl group, ethylsulfanyl group, propylsulfanyl group, isopropylsulfanyl group, butylsulfanyl group, tert-butylsulfanyl group, pentylsulfanyl group, tert-pentylsulfanyl group, hexylsulfanyl group and the like, with preference given to methylsulfanyl group, ethylsulfanyl group, propylsulfanyl group, isopropylsulfanyl group, butylsulfanyl group and tert-butylsulfanyl group, all of which having 1 to 4 carbon atoms.

The "$C_{1-6}$ alkylsulfonyl group" is linear or branched chain alkylsulfonyl group having 1 to 6 carbon atoms. Examples thereof include methylsulfonyl group, ethylsulfonyl group, propylsulfonyl group, isopropylsulfonyl group, butylsulfonyl group, tert-butylsulfonyl group, pentylsulfonyl group, tert-pentylsulfonyl group, hexylsulfonyl group and the like, with preference given to methylsulfonyl group, ethylsulfonyl group, propylsulfonyl group, isopropylsulfonyl group, butylsulfonyl group and tert-butylsulfonyl group, all of which having 1 to 4 carbon atoms.

The "$C_{1-6}$ alkylsulfamoyl group" is sulfamoyl group monosubstituted by the aforementioned "$C_{1-6}$ alkyl group". Examples thereof include methylsulfamoyl group, ethylsulfamoyl group, propylsulfamoyl group, isopropylsulfamoyl group, butylsulfamoyl group, tert-butylsulfamoyl group, pentylsulfamoyl group, tert-pentylsulfamoyl group, hexylsulfamoyl group and the like, with preference given to methylsulfamoyl group, ethylsulfamoyl group, propylsulfamoyl group, isopropylsulfamoyl group, butylsulfamoyl group and tert-butylsulfamoyl group, all of which having 1 to 4 carbon atoms.

The "di($C_{1-6}$)alkylsulfamoyl group" is sulfamoyl group di-substituted by the aforementioned "$C_{1-6}$ alkyl group". Examples thereof include dimethylsulfamoyl group, diethylsulfamoyl group, dipropylsulfamoyl group, diisopropylsulfamoyl group, dibutylsulfamoyl group, diisobutylsulfamoyl group, di-tert-butylsulfamoyl group, dipentylsulfamoyl group, ethylmethylsulfamoyl group, methylpropylsulfamoyl group, butylmethylsulfamoyl group, ethylpropylsulfamoyl group, ethylbutylsulfamoyl group and the like, with preference given to dimethylsulfamoyl group, diethylsulfamoyl group and dipropylsulfamoyl group.

The "($C_{1-6}$ alkoxy)carbonyl group" is alkoxycarbonyl group wherein the $C_{1-6}$ alkoxy moiety is exemplified by the aforementioned "$C_{1-6}$ alkoxy group". Examples thereof include methoxycarbonyl group, ethoxycarbonyl group, propoxycarbonyl group, isopropoxycarbonyl group, butoxycarbonyl group, isobutoxycarbonyl group, tert-butoxycarbonyl group, pentyloxycarbonyl group, hexyloxycarbonyl group and the like, with preference given to ($C_{1-4}$ alkoxy)carbonyl group selected from methoxycarbonyl group, ethoxycarbonyl group, propoxycarbonyl group, isopropoxycarbonyl group, butoxycarbonyl group and tert-butoxycarbonyl group.

The "$C_{1-7}$ acyl group" is alkanoyl group or aroyl group having 1 to 7 carbon atoms. Examples thereof include formyl group, acetyl group, propionyl group, butyryl group, pivaloyl group, benzoyl group and the like, with preference given to formyl group, acetyl group, pivaloyl group and benzoyl group.

The "($C_{1-6}$ alkyl)carbamoyl group" is alkylcarbamoyl group wherein the carbamoyl group is substituted by $C_{1-6}$ alkyl group exemplified for the aforementioned "$C_{1-6}$ alkyl group". Examples thereof include methylcarbamoyl group, ethylcarbamoyl group, propylcarbamoyl group, isopropylcarbamoyl group, butylcarbamoyl group, tert-butylcarbamoyl group, pentylcarbamoyl group, tert-pentylcarbamoyl group, hexylcarbamoyl group and the like, with preference given to ($C_{1-4}$ alkyl)carbamoyl group selected from methylcarbamoyl group, ethylcarbamoyl group, propylcarbamoyl group, isopropylcarbamoyl group, butylcarbamoyl group and tert-butylcarbamoyl group.

The "di($C_{1-6}$ alkyl)carbamoyl group" is dialkylcarbamoyl group wherein the carbamoyl group is disubstituted by the aforementioned "$C_{1-6}$ alkyl group", and the kind of the alkyl groups may be different. Examples thereof include dimethylcarbamoyl group, diethylcarbamoyl group, dipropylcarbamoyl group, diisopropylcarbamoyl group, dibutylcarbamoyl group, di-tert-butylcarbamoyl group, dipentylcarbamoyl group, di-tert-pentylcarbamoyl group, dihexylcarbamoyl group, methylethylcarbamoyl group, methylpropylcarbamoyl group, methylbutylcarbamoyl group, ethylpropylcarbamoyl group, ethylbutylcarbamoyl group and the like, with preference given to di($C_{1-4}$ alkyl)carbamoyl group selected from dimethylcarbamoyl group, diethylcarbamoyl group, dipropylcarbamoyl group, dibutylcarbamoyl group and di-tert-butylcarbamoyl group.

The "$C_{1-6}$ alkylamino group" is alkylamino group wherein the amino group is substituted by the aforementioned "$C_{1-6}$ alkyl group". Examples thereof include methylamino group, ethylamino group, propylamino group, isopropylamino group, butylamino group, isobutylamino group, tert-butylamino group, pentylamino group, isopentylamino group, tert-pentylamino group, hexylamino group and the like, with preference given to $C_{1-4}$ alkylamino group selected from methylamino group, ethylamino group, propylamino group, isopropylamino group, butylamino group, isobutylamino group and tert-butylamino group.

The "di $C_{1-6}$ alkylamino group" is dialkylamino group wherein the amino group is disubstituted by the aforementioned "$C_{1-6}$ alkyl group", and the kind of the alkyl groups may be different. Examples thereof include dimethylamino group, ethylmethylamino group, diethylamino group, methylpropylamino group, ethylpropylamino group, dipropylamino group, diisopropylamino group, dibutylamino group, diisobutylamino group, di-tert-butylamino group, dipentylamino group, diisopentylamino group, di-tert-pentylamino group, dihexylamino group and the like, with preference given to di($C_{1-4}$)alkylamino group selected from dimethylamino group, diethylamino group, dipropylamino group, diisopropylamino group, dibutylamino group, diisobutylamino group and di-tert-butylamino group.

The "$C_{1-7}$ acylamino group" is amino group substituted by the aforementioned "$C_{1-7}$ acyl group". Examples thereof include alkanoylamino group such as formylamino group, acetylamino group, propionylamino group, butyrylamino group, pivaloylamino group and the like; and aroylamino group wherein aryl group optionally has 1 to 3 substituents, such as benzoylamino group and the like, with preference given to formylamino group, acetylamino group, pivaloylamino group and benzoylamino group.

The "$C_{3-7}$ cycloalkyl group" is cyclic alkyl group having 3 to 7, preferably 3 to 6, carbon atoms. Examples thereof include cyclopropyl group, cyclobutyl group, cyclopentyl group, cyclohexyl group, cycloheptyl group and the like. Preferred are $C_{3-5}$ cycloalkyl group such as cyclopropyl group, cyclobutyl group, cyclopentyl group and the like, more preferred are cyclopropyl group and cyclobutyl group, and particularly preferred is cyclopropyl group.

The "$C_{2-6}$ alkenyl group" is alkenyl group having 2 to 6 carbon atoms. Examples thereof include vinyl group, 1-propenyl group, allyl group, 1-butenyl group, 2-butenyl group, 3-butenyl group, 1-pentenyl group, 2-pentenyl group, 3-pentenyl group, 4-pentenyl group, 5-hexenyl group and the like, with preference given to $C_{2-4}$ alkenyl group such as vinyl group, allyl group and the like.

The "$C_{2-6}$ alkynyl group" is alkynyl group having 2 to 6, preferably 2 to 4, carbon atoms. Examples thereof include ethynyl group, 1-propynyl group, 2-propynyl group, 1-butynyl group, 2-butynyl group, 3-butynyl group, 1-pentynyl group, 2-pentynyl group, 3-pentynyl group, 4-pentynyl group, 5-hexynyl group and the like, with preference given to $C_{2-4}$ alkynyl group selected from ethynyl group, 1-propynyl group and 2-propynyl group.

The "aralkyl group" is arylalkyl group wherein the aforementioned "$C_{1-6}$ alkyl group" is substituted by the aforementioned "aryl group". The position of the substituent is not particularly limited as long as it is chemically acceptable. Examples of "aralkyl group" include benzyl group, phenylethyl group, 3-phenylpropyl group, 4-phenylbutyl group, 5-phenylpentyl group, 6-phenylhexyl group, 1-naphthylmethyl group, 2-naphthylmethyl group and the like, with preference given to phenyl($C_{1-2}$)alkyl group wherein the "aryl" moiety is phenyl and the "alkyl" moiety is methyl or ethyl, such as benzyl group and phenylethyl group.

The "$C_{1-6}$ alkylsulfonyloxy group" is alkylsulfonyloxy group wherein the $C_{1-6}$ alkyl moiety is the aforementioned "$C_{1-6}$ alkyl group". Examples thereof include methylsulfonyloxy group, ethylsulfonyloxy group, propylsulfonyloxy group, isopropylsulfonyloxy group, butylsulfonyloxy group, isobutylsulfonyloxy group, tert-butylsulfonyloxy group, pentylsulfonyloxy group, isopentylsulfonyloxy group, tert-pentylsulfonyloxy group and hexylsulfonyloxy group, with preference given to $C_{1-4}$ alkylsulfonyloxy group selected from methylsulfonyloxy group, ethylsulfonyloxy group, propylsulfonyloxy group, isopropylsulfonyloxy group, butylsulfonyloxy group, isobutylsulfonyloxy group and tert-butylsulfonyloxy group.

The "$C_{1-3}$ alkylenedioxy group" is methylenedioxy group, ethylenedioxy group or propylenedioxy group, preferably methylenedioxy group or ethylenedioxy group, and particularly preferably methylenedioxy group.

The "$C_{1-6}$ alkylene group" is alkylene group having 1 to 6 carbon atoms. Examples thereof include methylene group, ethylene group, propylene group, butylene group, pentylene group, hexylene group and the like, with preference given to $C_{1-4}$ alkylene group selected from methylene group, ethylene group and propylene group.

The "$C_{2-6}$ alkynylene group" is alkynylene group having 2 to 6, preferably 2 or 3, carbon atoms. Examples thereof include vinylene group, 1-propenylene group, 2-propenylene group, 1-butenylene group, 2-butenylene group, 3-butenylene group, 1-pentenylene group, 2-pentenylene group, 3-pentenylene group, 4-pentenylene group, 1-hexenylene group, 2-hexenylene group, 3-hexenylene group, 4-hexenylene group, 5-hexenylene group and the like, with preference given to $C_{2-3}$ alkynylene group selected from vinylene group, 1-propenylene group and 2-propenylene group.

The aryl group and heteroaryl group of the present invention are optionally substituted by 1 to 3 substituents selected from halogen atom, $C_{1-6}$ alkyl group, halo($C_{1-6}$) alkyl group, hydroxy($C_{1-6}$)alkyl group, $C_{1-6}$ alkoxy($C_{1-6}$) alkyl group, hydroxyl group, $C_{1-6}$ alkoxy group, halo($C_{1-6}$) alkoxy group, mercapto group, $C_{1-6}$ alkylthio group, $C_{1-6}$ alkylsulfanyl group, $C_{1-6}$ alkylsulfonyl group, aminosulfonyl group, $C_{1-6}$ alkylsulfamoyl group, di($C_{1-6}$) alkylsulfamoyl group, carboxy group, ($C_{1-6}$ alkoxy)carbonyl group, $C_{1-7}$ acyl group, carbamoyl group, ($C_{1-6}$ alkyl)carbamoyl group, di($C_{1-6}$ alkyl)carbamoyl group, cyano group, nitro group, amino group, $C_{1-6}$ alkylamino group, di($C_{1-6}$)alkylamino group, $C_{1-7}$ acylamino group, $C_{1-3}$ alkylenedioxy group,

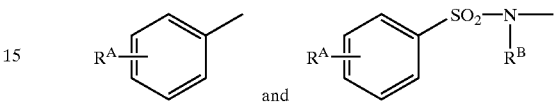

and wherein $R^A$ is ($C_{1-6}$ alkoxy)carbonyl group or carboxy group, and $R^B$ is hydrogen atom or $C_{1-6}$ alkyl group.

The "salt" of the compound of the present invention is exemplified by, but not limited to, inorganic acid addition salts such as hydrochloride, hydrobromide, sulfate, phosphate, nitrate and the like; organic acid addition salts such as acetate, propionate, succinate, glycolate, lactate, malate, oxalate, tartrate, citrate, maleate, fumarate, methanesulfonate, benzenesulfonate, p-toluenesulfonate, ascorbate and the like; amino acid addition salts such as aspartate, glutamate and the like. Preferable salts are hydrochloride and fumarate, particularly preferably fumarate.

The present invention encompasses solvates, wherein a "solvate" of the compound means that the compound of the present invention is bonded to a solvent molecule such as water, alcohol and the like via a comparatively weak bond due to van der Waals force, electrostatic interaction, hydrogen bond, charge transfer bond, coordinate bond and the like in a solid such as crystal, amorphous and the like or a solution. In some cases, a solvent may be taken in a solid as exemplified by hydrate, alcoholate and the like. Preferable solvate is hydrate.

A "prodrug" of the compound means a derivative of the compound of the present invention, which has a chemically or metabolically decomposable group, and shows pharmaceutical activity upon hydrolysis, solvolysis or decomposition under physiological conditions.

The compounds of the formula [I], [I-2] and [I-3] of the present invention may be present as various isomers such as optical isomer, stereoisomer, geometric isomer, tautomer and the like. The present invention encompasses all these isomers and mixtures thereof.

In the compound of the formula [I] of the present invention, $R^1$ is preferably aryl group, more preferably phenyl group or naphthyl group and particularly preferably phenyl group. When $R^1$ is aryl group, the substituent is preferably halogen atom, $C_{1-4}$ alkyl group, hydroxy($C_{1-6}$) alkyl group, $C_{1-6}$ alkoxy($C_{1-6}$)alkyl group, hydroxyl group, $C_{1-4}$ alkoxy group, cyano group, nitro group or $C_{1-3}$ alkylenedioxy group, more preferably chlorine atom, methyl group, hydroxymethyl group, methoxy group, cyano group, nitro group, hydroxyl group or methylenedioxy group, particularly preferably methyl group, hydroxymethyl group, methoxy group or methylenedioxy group.

When $R^1$ is heteroaryl group, $R^1$ is preferably selected from thienyl group, furyl group, pyridyl group and thiazolyl group, and the substituent when $R^1$ is heteroaryl group is preferably $C_{1-6}$ alkyl group or halogen atom, particularly preferably methyl group or bromine atom.

$R^2$ is preferably optionally substituted and optionally branched $C_{1-4}$ alkyl group, $C_{3-5}$ cycloalkyl group, $C_{2-4}$ alkenyl group or aralkyl group, and the substituent of $C_{1-4}$ alkyl group is preferably $C_{1-4}$ alkoxy group. $R^2$ is more preferably methyl group, ethyl group, cyclopropyl group or cyclobutyl group, most preferably methyl group or cyclopropyl group, and particularly preferably cyclopropyl group.

$R^3$ is preferably hydroxyl group, and $R^4$ is preferably hydrogen atom. $R^5$ and $R^6$ are each preferably methyl group. $R^7$ is preferably aryl group, more preferably phenyl group or naphthyl group. The substituent of $R^7$ is preferably $C_{1-6}$ alkyl group, $C_{1-6}$ alkoxy group, hydroxyl group or $C_{1-3}$ alkylenedioxy group, more preferably $C_{1-4}$ alkyl group, $C_{1-4}$ alkoxy group or $C_{1-3}$ alkylenedioxy group, most preferably $C_{1-4}$ alkyl group or $C_{1-4}$ alkoxy group, particularly preferably methyl group or methoxy group. $R^7$ is preferably naphthyl group, 4-methoxy-3-methylphenyl group or 3,4-methylenedioxyphenyl group, and particularly preferably naphthyl group or 4-methoxy-3-methylphenyl group. $X^1$ is preferably $C_{1-6}$ alkylene group, particularly preferably methylene group. $X^2$ is preferably methylene group. $X^3$ is preferably methylene group. $X^4$ and $X^5$ are each preferably a single bond.

$R^{11}$ is preferably hydrogen atom, halogen atom, $C_{1-4}$ alkyl group, hydroxy($C_{1-6}$)alkyl group, $C_{1-6}$ alkoxy($C_{1-6}$)alkyl group, hydroxyl group, $C_{1-4}$ alkoxy group, cyano group or nitro group, more preferably hydrogen atom, chlorine atom, methyl group, hydroxymethyl group, methoxy group, cyano group, hydroxyl group or nitro group, particularly preferably hydrogen atom.

$R^{12}$ is preferably hydrogen atom, halogen atom, $C_{1-4}$ alkyl group, hydroxy($C_{1-6}$)alkyl group, $C_{1-6}$ alkoxy($C_{1-6}$)alkyl group, hydroxyl group, $C_{1-4}$ alkoxy group, cyano group or nitro group, more preferably chlorine atom, methyl group, hydroxymethyl group, methoxy group, cyano group, hydroxyl group or nitro group, particularly preferably methyl group, hydroxymethyl group or methoxy group.

$R^{21}$ is preferably methyl group, ethyl group, cyclopropyl group or cyclobutyl group, more preferably methyl group or cyclopropyl group, particularly preferably cyclopropyl group.

The configuration of

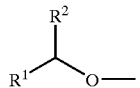

is preferably

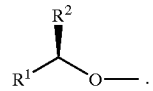

A preferable embodiment of the compound [I] of the present invention is compound [I-2], and more preferably compound [I-3].

Specific examples of the preferable compounds of the present invention are given in the following:

(2R)-1-[1,1-dimethyl-2-(naphthalen-2-yl)ethylamino]-3-[(cyclopropyl)(2-methoxyphenyl)methoxy]propan-2-ol, (2R)-1-[1,1-dimethyl-2-(naphthalen-2-yl)ethylamino]-3-[(cyclopropyl)(2-methylphenyl)methoxy]propan-2-ol, (2R)-1-[1,1-dimethyl-2-(naphthalen-2-yl)ethylamino]-3-[(cyclopropyl)(phenyl)methoxy]propan-2-ol, (2R)-1-[1,1-dimethyl-2-(naphthalen-2-yl)ethylamino]-3-[1-(2-methoxyphenyl)ethoxy]propan-2-ol, (2R)-1-[1,1-dimethyl-2-(naphthalen-2-yl),ethylamino]-3-[1-(2-methylphenyl)ethoxy]propan-2-ol, (2R)-1-[1,1-dimethyl-2-(naphthalen-2-yl)ethylamino]-3-[1 (2-methoxyphenyl)propoxy]propan-2-ol, (2R)-1-[1,1-dimethyl-2-(naphthalen-2-yl)ethylamino]-3-[1-(2-cyanophenyl)ethoxy]propan-2-ol, (2R)-1-[1,1-dimethyl-2-(naphthalen-2-yl)ethylamino]-3-[1-(3-methoxyphenyl)ethoxy]propan-2-ol, and (2R)-1-[1,1-dimethyl-2-(naphthalen-2-yl)ethylamino]-3-[1-(3-methylphenyl)ethoxy]propan-2-ol; and (2R)-1-[1,1-dimethyl-2-(naphthalen-2-yl)ethylamino]-3-[(cyclopropyl)(2-hydroxymethylphenyl)methoxy]propan-2-ol.

When the compound of the present invention is used as a pharmaceutical product, its form is the compound itself (free form), a salt of the compound, a solvate of the compound or a prodrug of the compound, which is preferably a free form, a salt of the compound or a solvate of the compound, particularly preferably a salt of the compound.

Now the production method of the compound of the formula [I] of the present invention is explained in detail. It is needless to say that the present invention is not limited to these production methods. When constructing the compound of the present invention, the construction can be started from the moiety easily produced. When a reactive functional group is involved in each step, it may be protected or deprotected as appropriate. For easy progress of the reaction, a reagent other than the exemplified reagent can be used as appropriate.

Any compound obtained in each step can be isolated and purified by a conventional method, and in some cases, the next step is performed without isolation or purification.

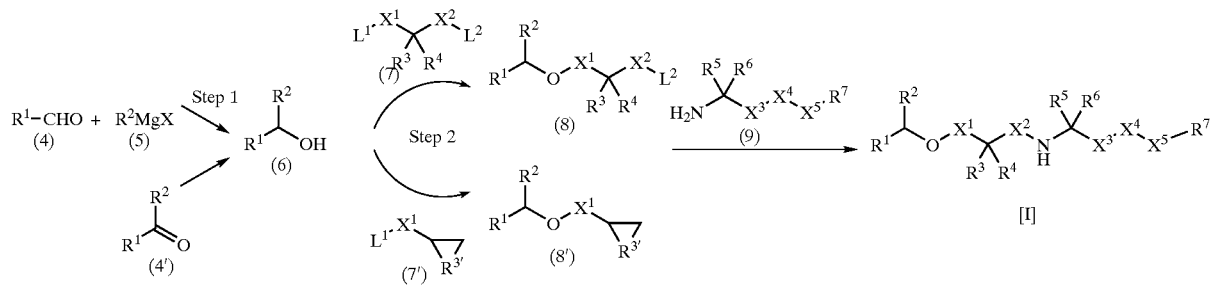

wherein X is halogen atom, $L^1$ and $L^2$ are each a leaving group, such as halogen atom and sulfonyloxy group (e.g., 3-nitrobenzenesulfonyloxy group, p-toluenesulfonyloxy group, benzenesulfonyloxy group, p-bromobenzenesulfonyloxy group, methanesulfonyloxy group, trifluoromethanesulfonyloxy group and the like), $R^{3'}$ is oxygen atom or sulfur atom, and other symbols are as defined above.

Step 1

By reacting aldehyde compound (4) with Grignard reagent (5) in diethyl ether, tetrahydrofuran, 1,4-dioxane and the like or a mixed solvent thereof at a temperature of from −80° C. to room temperature, compound (6) can be obtained. The Grignard reagent can be prepared by a known-method.

Alternatively, ketone compound (4') is reduced with a reducing agent such as lithium aluminum hydride, sodium borohydride, lithium borohydride and the like in diethyl ether, tetrahydrofuran, 1,4-dioxane, isopropanol and the like or a mixed solvent thereof at a temperature of from −10° C. to room temperature to give compound (6). In this case, asymmetric reduction using an asymmetric reducing agent such as B-chlorodiisopinocampheylborane and the like, or asymmetric hydrogenation using a ruthenium complex such as dichloro[(S)-(−)-2,2'-bis(diphenylphosphino)-1,1'-binaphthyl]ruthenium (II) and the like can be also conducted.

Step 2

By reacting the compound (6) to be obtained in Step 1 with compound (7) in N,N-dimethylformamide, dimethyl sulfoxide, tetrahydrofuran and the like or a mixed solvent thereof in the presence of a base such as sodium hydride, sodium hydroxide, potassium hydroxide, sodium carbonate, potassium carbonate, sodium hydrogencarbonate, potassium hydrogencarbonate, triethylamine, N,N-diisopropylethylamine, N-methylmorpholine, pyridine, 4-dimethylaminopyridine and the like at a temperature of from 0° C. to room temperature, compound (8) can be obtained. In this case, $L^1$ is a leaving group having greater reactivity than does $L^2$.

When a compound wherein $R^3$ is hydroxyl group or mercapto group, $R^4$ is hydrogen atom and $X^2$ is methylene group is desired, compound (7') is used instead of compound (7). In this case, alkylammonium hydrogensulfate such as tetrabutylammonium hydrogensulfate and the like can be added.

Upon determination of the reagent and leaving group to be used, a stereoselective reaction can be carried out.

Step 3

By reacting compound (8) to be obtained in Step 2 with compound (9) in N,N-dimethylformamide, dimethyl sulfoxide, tetrahydrofuran and the like or a mixed solvent thereof in the presence of a base such as sodium hydride, sodium hydroxide, potassium hydroxide, sodium carbonate, potassium carbonate and the like at a temperature of from 0° C. to room temperature, a compound of the formula [I] can be obtained.

In addition, by reacting compound (8') with compound (9) in methanol, ethanol, n-propanol, isopropanol, tetrahydrofuran, 1,4-dioxane, acetonitrile, toluene and the like or a mixed solvent thereof at room temperature to refluxing temperature, a compound of the formula [I] wherein $R^3$ is hydroxyl group or mercapto group, $R^4$ is hydrogen atom, and $X^2$ is methylene group can be obtained. In this case, alkali perchlorate such as lithium perchlorate and the like is preferably added.

When an acid addition salt of compound of the formula [I] is desired, a known method can be used. For example, compound of the formula [I] is dissolved in water, methanol, ethanol, n-propanol, isopropanol, diethyl ether, tetrahydrofuran, 1,4-dioxane, ethyl acetate, dichloromethane, 1,2-dichloroethane, chloroform and the like or a mixed solvent of these, the above-mentioned solvent, in which a desired acid has been dissolved, is added and the precipitated crystals are collected by filtration, or the solution is concentrated under reduced pressure.

When the acid addition salt of the compound of the formula [I] is converted to a free form, the acid addition salt of the compound of the formula [I] is subjected to partitioning between two phases of an aqueous solution of a base such as sodium hydrogencarbonate, potassium hydrogencarbonate, sodium carbonate, potassium carbonate, sodium hydroxide, potassium hydroxide, lithium hydroxide and the like and a solvent such as ethyl acetate, dichloromethane, 1,2-dichloroethane, chloroform, methyl ethyl ketone, toluene and the like to give a free form of the compound of the formula [I].

The compound (4') can be prepared by the following method.

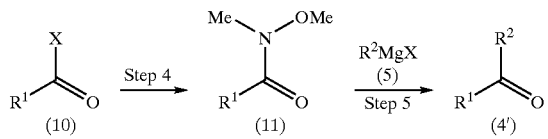

wherein each symbol is as defined above.

Step 4

By reacting compound (10) with N,O-dimethylhydroxylamine or a salt thereof in a solvent such as dichloromethane, chloroform, 1,2-dichloroethane, tetrahydrofuran, 1,4-dioxane and the like in the presence of a base such as triethylamine, N,N-diisopropylethylamine and the like, compound (11) can be obtained.

Step 5

By reacting compound (11) to be obtained in Step 4 with Grignard reagent (5) in diethyl ether, tetrahydrofuran, 1,4-dioxane and the like or a mixed solvent thereof at a temperature of from −80° C. to room temperature, compound (4') can be obtained.

The compound (9) can be prepared by the following method.

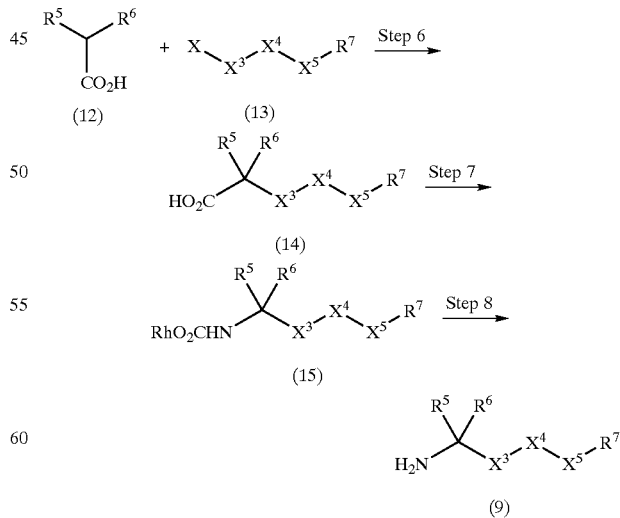

wherein Rh is carboxy-protecting group such as benzyl group, tert-butyl group and the like and other symbol is as defined above.

Step 6

By reacting compound (12) with compound (13) in a solvent such as tetrahydrofuran, n-hexane and the like in the presence of a base such as n-butyllithium and the like and hexamethylphosphoramide, compound (14) can be obtained.

Step 7

In this step, compound (14) to be obtained in Step 6 is subjected to Curtius rearrangement to give compound (15). The compound (14) is reacted with alkyl halocarbonate such as ethyl chlorocarbonate and the like in water, acetone, methyl ethyl ketone and the like or a mixed solvent thereof in the presence of a base such as triethylamine, N,N-diisopropylethylamine and the like. Then, sodium azide is reacted, and the obtained compound is subjected to rearrangement under heating and reacted with alcohol represented by Rh—OH to give compound (15).

Step 8

In this step, —CO$_2$Rh of compound (15) obtained in Step 7 is deprotected by a method generally employed for removing this protecting group. For example, when Rh is benzyl group, compound (15) is subjected to hydrogenation using a catalyst such as palladium carbon, palladium black, palladium hydroxide on carbon, Raney-nickel and the like in a solvent such as methanol, ethanol, n-propanol, isopropanol, tetrahydrofuran, 1,4-dioxane and the like to give compound (9). When, for example, Rh is tert-butyl group, a reaction using an acid such as hydrogen chloride, sulfuric acid, hydrogen bromide and the like in water, methanol, ethanol, n-propanol, isopropanol, tetrahydrofuran, 1,4-dioxane, acetic acid and the like or a mixed solvent thereof gives compound (9).

When, of the compounds (9), compound (9') wherein —X$^3$—X$^4$—X$^5$— is methylene is desired, the following method can be employed.

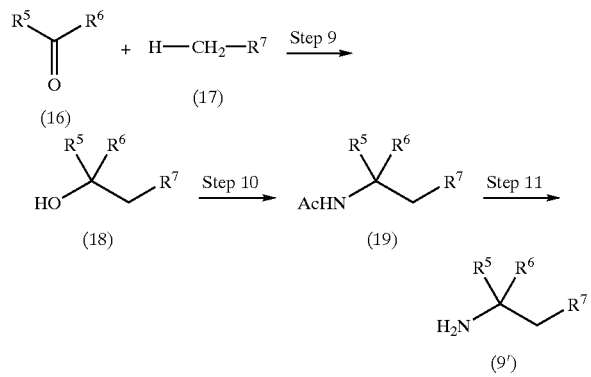

wherein each symbol is as defined above.

Step 9

By reacting compound (17) with compound (16) in a solvent such as tetrahydrofuran, n-hexane and the like in the presence of a base such as n-butyllithium and the like, compound (18) can be obtained.

Step 10

By reacting compound (18) to be obtained in Step 9 in acetonitrile and acetic acid by adding sulfuric acid, compound (19) is obtained.

Step 11

By reacting compound (19) to be obtained in Step 10 in water, methanol, ethanol, n-propanol, isopropanol, tetrahydrofuran, 1,4-dioxane, acetic acid and the like or a mixed solvent thereof using an acid such as hydrogen chloride, sulfuric acid, hydrogen bromide and the like under heating, compound (9') is obtained.

The compound (9') can be also obtained by reacting compound (19) in a solvent such as water, methanol, ethanol, n-propanol, isopropanol, tetrahydrofuran, 1,4-dioxane, ethylene glycol and the like using a base such as sodium hydroxide, potassium hydroxide, lithium hydroxide and the like under heating.

The compound (9') can be also obtained by the following method.

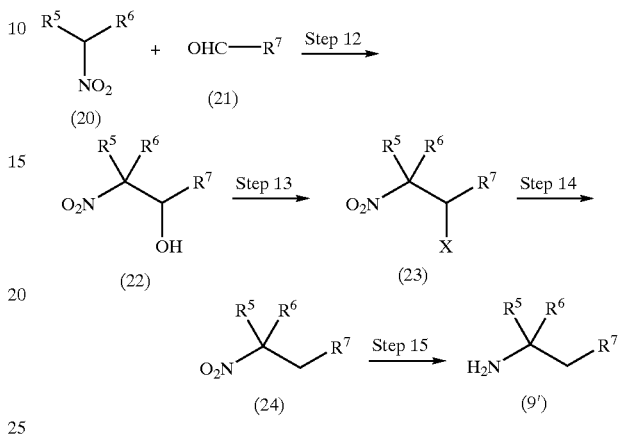

wherein each symbol is as defined above.

Step 12

By reacting compound (21) with compound (20) in a solvent such as tetrahydrofuran, N,N-dimethylformamide, dimethyl sulfoxide and the like, in the presence of tetraalkylammonium halide such as tetrabutylammonium fluoride and the like and trialkylhalosilane such as tert-butyldimethylchlorosilane and the like, compound (22) can be obtained.

Step 13

By subjecting compound (22) to be obtained in Step 12 to halogenation using a halogenating agent such as thionyl chloride, oxalyl chloride and the like, compound (23) can be obtained. In this reaction, the halogenating agent itself to be used may be used as a solvent, or a solvent such as dichloromethane, chloroform, 1,2-dichloroethane, tetrahydrofuran, 1,4-dioxane and the like may be used.

Step 14

By subjecting compound (23) to be obtained in Step 13 to hydrogenation in a solvent such as methanol, ethanol, n-propanol, isopropanol, tetrahydrofuran, 1,4-dioxane, ethyl acetate and the like in the presence of a catalyst such as palladium carbon, palladium black, palladium hydroxide on carbon and the like, compound (24) can be obtained. In this reaction, pressurization to some extent is preferable.

Step 15

By subjecting compound (24) to be obtained in Step 14 to hydrogenation using a catalyst such as Raney-nickel and the like in a solvent such as methanol, ethanol, n-propanol, isopropanol, tetrahydrofuran, 1,4-dioxane and the like, compound (9') can be obtained. In this reaction, pressurization to some extent is preferable.

The intermediate compounds shown in the above-mentioned production method are useful as an intermediate for compound [I]. Of these intermediate compounds, the following compound is a novel compound:

(A) compound [II] consisting of part of compound (6) and compound obtained by Step 2 of Example 57 below, a salt thereof and a solvate thereof (R$^{11'}$ is preferably C$_{1-4}$ alkyl group, hydroxy(C$_{1-6}$)alkyl group or C$_{1-4}$ alkoxy group), (B) compound [III] consisting of part of compound (4') and compound obtained by Step 2 of Example 58 below, a salt thereof and a solvate thereof ($R^{11}$" is preferably $C_{1-4}$ alkoxy group), (C) compound [IV] consisting of compound (14), compound (15) and compound (24) (in the formulas (14), (15) and (24), $R^5$ and $R^6$ are methyl group, and —$X^3$—$X^4$—$X^5$— $R^7$ group is 2-naphthylmethyl group), a salt thereof and a solvate thereof.

The thus-obtained compound of the formula [I] of the present invention has a superior calcium receptor antagonistic action. When the compound of the present invention is to be used as a therapeutic agent of osteoporosis, hypoparathyreosis, osteosarcoma, periodontal disease, bone fracture, steoarthrosis, chronic rheumatoid arthritis, Paget's disease, humoral hypercalcemia, autosomal dominant hypocalcemia and the like, it is generally administered systemically or topically, and orally or parenterally.

While the dose varies depending on age, body weight, condition, treatment effect, administration method, treatment period and the like, it is generally 0.01 mg to 10 g for an adult per day, which is given once or in several portions a day by oral or parenteral administration.

When the compound of the present invention is prepared into a solid composition for oral administration, a dosage form of tablet, pill, powder, granule and the like can be employed. In such a solid composition, one or more active ingredient is admixed with at least one inert diluent, dispersing agent, absorbent and the like, such as lactose, mannitol, glucose, hydroxypropyl cellulose, crystalline cellulose, starch, polyvinyl hydrin, magnesium aluminometasilicate, anhydrous silicic acid powder and the like. The composition may contain an additive other than diluent according to a conventional method.

For preparation of tablets or pills, gastric or enteric film of sucrose, gelatin, hydroxypropyl cellulose, hydroxymethylcellulose phthalate and the like may be applied or two or more layers may be formed. In addition, they may be prepared into capsules of gelatin or ethylcellulose.

For preparation of liquid composition for oral administration, a dosage form such as pharmaceutically acceptable emulsifier, solubilizer, suspension, syrup, elixir and the like can be employed. The diluent to be used is, for example, purified water, ethanol, vegetable oil, emulsifier and the like. This composition may contain diluent and an adjuvant other than the diluent, such as wetting agent, suspending agent, sweetener, flavor, perfume, preservative and the like.

For preparation of parenteral injection, sterile aqueous or nonaqueous solvent, solubilizer, suspending agent or emulsifier is used. Examples of the aqueous solvent, solubilizer and suspending agent include distilled water for injection, physiological saline, cyclodextrin and derivatives thereof, organic amines such as triethanolamine, diethanolamine, monoethanolamine, triethylamine and the like, inorganic alkali solution and the like.

When a water-soluble solvent is to be prepared, for example, propylene glycol, polyethylene glycol, vegetable oil such as olive oil, alcohol such as ethanol, and the like may be used. As the solubilizer, for example, surfactant (forming a mixed micelle) such as polyoxyethylene hydrogenated castor oil, sucrose esters of fatty acid and the like, lecithin or hydrogenated lecithin (forming a liposome) and the like can be used. In addition, an emulsion preparation consisting of a water insoluble solvent such as vegetable oil and the like, and lecithin, polyoxyethylene hydrogenated castor oil, polyoxyethylene polyoxypropylene glycol and the like may be formed.

As other compositions for parenteral administration, an external liquid, liniment such as ointment, suppository, pessary and the like, containing one or more active ingredients and prepared by a method known per se may be formulated.

EXAMPLES

The compound of the formula [I] of the present invention and its production methods are explained in detail by referring to the following Examples, which are not to be construed as limitative.

Example 1

(2R)-1-[1,1-Dimethyl-2-(naphthalen-2-yl)ethylamino]-3-[(cyclopropyl)(2-methoxyphenyl)methoxy]propan-2-ol.

Step 1

(Cyclopropyl) (2-methoxyphenyl)methanol.

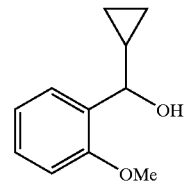

Magnesium (10.7 g)was suspended in tetrahydrofuran (80 ml), and to the suspension was added iodine (5 mg). Bromocyclopropane (32.0 ml) was added dropwise thereto over 1.5 hr and the mixture was heated under ref lux for 1.5 hr. Thereto was added tetrahydrofuran to give a 1M cyclopropylmagnesium bromide-tetrahydrofuran solution. Subsequently, o-anisaldehyde (8.17 g) was dissolved in tetrahydrofuran (150 ml), the 1M cyclopropylmagnesium bromide-tetrahydrofuran solution (90 ml) was added dropwise thereto over 50 min under ice-cooling, and the mixture was stirred at room temperature for 12 hr. The reaction mixture was ice-cooled, a saturated aqueous ammonium chloride solution (9 ml) was added, and the reaction mixture was stirred at room temperature for 30 min. The organic layer was dried over magnesium sulfate and concentrated under reduced pressure. The obtained residue was purified by silica gel column chromatography (n-hexane:ethyl acetate=9:1) to give the title compound (6.13 g).

$^1$H-NMR(300 MHz, δppm, DMSO-$d_6$) 7.41(1H,d,J=7.8 Hz), 7.19(1H,dt,J=1.6, 7.7 Hz), 6.92(2H,t,J=7.2 Hz), 4.88 (1H,d,J=4.8 Hz), 4.55(1H,t,J=5.5 Hz), 3.76(3H,s), 1.09–1.00(1H,m), 0.33–0.25(4H,m). MS(ESI,m/z) 161(M+ H—$H_2O$)$^+$.

Step 2

(R)-2-[(Cyclopropyl)(2-methoxyphenyl)methoxymethyl] oxirane

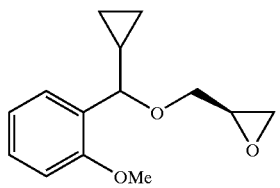

(Cyclopropyl)(2-methoxyphenyl)methanol (3.57 g) obtained in Step 1 was dissolved in N,N-dimethylformamide (50 ml), sodium hydride (960 mg, 60% oil) was added and the mixture was stirred for 3 min. To the resulting mixture was added (R)-glycidyl 3-nitrobenzenesulfonate (6.22 g) and the mixture was stirred at room temperature for 12 hr. The reaction mixture was poured into water and extracted with diethyl ether. The organic layer was washed successively with water and saturated brine, dried over sodium sulfate, and concentrated under reduced pressure. The obtained residue was purified by silica gel column chromatography (n-hexane:ethyl acetate=88:12) to give the title compound (1.10 g).

Step 3
2-Methyl-1-(naphthalen-2-yl)-2-nitropropanol

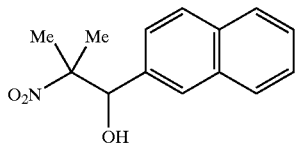

To tetrabutylammonium fluoride 3 hydrate (2.41 g) was added tetrahydrofuran (20 ml) and the mixture was ice-cooled. To the mixture were added 2-nitropropane (2.7 ml), 2-naphthaldehyde (3.12 g) and triethylamine (2.8 ml) under an argon atmosphere. To the mixture was added a solution of tert-butyldimethylchlorosilane (4.51 g) in tetrahydrofuran (20 ml). The resulting mixture was stirred for 40 min while allowing to warm to room temperature from ice-cooling. After removing insoluble matter by filtration, the filtrate was poured into a solution (500 ml) of diethyl ether-n-hexane=1:3 and the mixture was washed twice with water (40 ml). The organic layer was dried over anhydrous sodium sulfate and concentrated under reduced pressure. The obtained residue was subjected to crystallization from n-hexane to give the title compound (3.78 g).

Step 4
2-(1-Chloro-2-methyl-2-nitropropyl)naphthalene

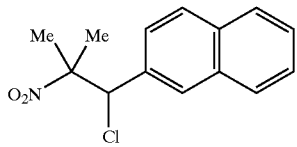

To 2-methyl-1-(naphthalen-2-yl)-2-nitropropanol (1.23 g) obtained in Step 3 was added thionyl chloride (3.1 ml), and the resulting mixture was heated under reflux for 1 hr, and stirred at room temperature for 12 hr. The reaction mixture was concentrated under reduced pressure and the residue thus obtained was poured into water and extracted with ethyl acetate. The organic layer was washed successively with water and saturated aqueous sodium hydrogencarbonate solution, dried over anhydrous sodium sulfate, and concentrated under reduced pressure. The obtained residue was purified by silica gel column chromatography (n-hexane:ethyl acetate=93:7). Recrystallization from a solution of n-hexane:ethyl acetate=4:1, yielded title compound (776 mg).

Step 5
2-(2-Methyl-2-nitropropyl)naphthalene

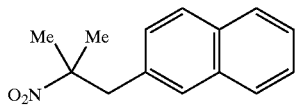

2-(1-Chloro-2-methyl-2-nitropropyl)naphthalene (200 mg) obtained in Step 4 was dissolved in methanol (5 ml) and ethyl acetate (5 ml) and to the solution was added 10% palladium carbon (20 mg). A hydrogenation reaction was performed at pressure of 3 atm for 2 hr. After filtration of the reaction mixture using Celite, the title compound (139 mg) was obtained by purification using silica gel column chromatography (n-hexane:ethyl acetate=95:5).

$^1$H-NMR(300 MHz, δppm, CDCl$_3$) 7.85–7.76(3H,m), 7.58(1H,s), 7.50–7.44(2H,m), 7.22(1H,dd,J=1.7, 8.4 Hz), 3.37(2H,s), 1.69(6H,s). MS(APCI,m/z) 183(M+H—NO$_2$)$^+$.

Step 6
[2-Methyl-1-(naphthalen-2-yl)propan-2-yl]amine

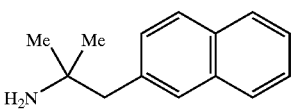

Raney nickel W2 (200 mg) was suspended in ethanol (10 ml), to the suspension was added 2-(2-methyl-2-nitropropyl) naphthalene (134 mg) obtained in Step 5, and hydrogenation was performed at a pressure of 3.5 atom for 12 hr.

The reaction mixture was filtered through Celite and concentrated under reduced pressure. The obtained residue was subjected to crystallization from ethyl acetate to give the title compound (70 mg).

Step 7
2-Methyl-1-(naphthalen-2-yl)-2-propanol

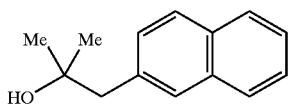

2-Methylnaphthalene (7.11 g) was dissolved in tetrahydrofuran (100 ml) and the solution was cooled to −69° C. To the solution was added dropwise a 1.6M n-butyllithium-tetrahydrofuran solution (34 ml), and then a solution of acetone (4.41 ml) in tetrahydrofuran (4.41 ml). The reaction mixture was stirred for 12 hr while allowing to warm to room temperature. To the reaction mixture was added dropwise saturated ammonium chloride solution (6 ml), and the resulting mixture was poured into water (200 ml) and extracted with diethyl ether. The organic layer was washed with water, dried over anhydrous sodium sulfate, and concentrated under reduced pressure. The obtained residue was purified by silica gel column chromatography (n-hexane:ethyl acetate=85:15) to give the title compound (3.80 g).

Step 8
N-[2-Methyl-1-(naphthalen-2-yl)propan-2-yl]acetamide

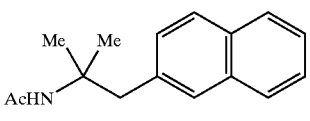

To 2-methyl-1-(naphthalen-2-yl)-2-propanol (500 mg) obtained in Step 7 were added acetonitrile (0.5 ml) and acetic acid (0.5 ml) in this order. After ice-cooling the mixture, sulfuric acid (0.5 ml) was added dropwise. The mixture was stirred under ice-cooling for 20 min and poured into a 1N aqueous sodium hydroxide solution, and the mixture was extracted with diethyl ether. The organic layer was washed with water, dried over sodium sulfate, and concentrated under reduced pressure. The obtained residue was subjected to recrystallization from ethyl acetate-n-hexane to give the title compound (303 mg).

Step 9
[2-Methyl-1-(naphthalen-2-yl)propan-2-yl]amine

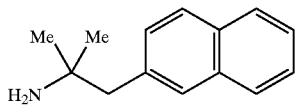

To N-[2-methyl-1-(naphthalen-2-yl)propan-2-yl] acetamide (26 mg) obtained in Step 8 was added 6N hydrochloric acid (2 ml) and the mixture was heated under reflux for 5 hr. The reaction mixture was poured into water, made basic with a 4N aqueous sodium hydroxide solution, and extracted with diethyl ether. The organic layer was washed with water, dried over potassium carbonate and concentrated under reduced pressure to give the title compound (19 mg).

Step 10
2,2-Dimethyl-3-(naphthalen-2-yl)propionic acid

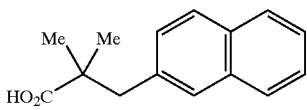

A solution of diisopropylamine (576 ml) in tetrahydrofuran (3.5 L) was cooled to −68° C., and a 2.6M n-butyllithium-n-hexane solution (1.5 L) was slowly added under an argon atmosphere. After addition of a solution of isobutyric acid (181 ml) in hexamethylphosphoramide (340 ml), the reaction mixture was stirred at room temperature for 30 min. After ice-cooling the mixture, a solution of 2-bromomethylnaphthalene (392 g) in tetrahydrofuran (1 L) was added dropwise, and the obtained solution was stirred at room temperature for 1 day. The reaction mixture was ice-cooled, 6N hydrochloric acid (665 ml) was added thereto, and the organic layer was separated from the aqueous layer. The separated organic layer was concentrated under reduced pressure to yield a residue. On the other hand, ethyl acetate and water were added to the aqueous layer and the organic layer was separated from the aqueous layer. The organic layer and the aforementioned residue were combined and washed three times with water. The organic layer was extracted with a solution of sodium hydroxide (80 g) in water (600 ml), and then extracted three times with a 4N aqueous sodium hydroxide solution (200 ml). The aqueous layer was washed with ethyl acetate, acidified with conc. hydrochloric acid, and extracted with ethyl acetate. The ethyl acetate layer was washed with aqueous sodium chloride solution, dried over anhydrous sodium sulfate, and concentrated under reduced pressure to give the title compound (177.5 g).
$^1$H-NMR(300 MHz, δppm, DMSO-d$_6$) 7.88–7.80(3H,m), 7.66(1H,s), 7.51–7.44(2H,m), 7.33(1H,dd,J=8.4, 1.6 Hz), 2.96(2H,s), 1.13(6H,s). MS(FAB,m/z) 228(M)$^+$.

Step 11
N-[2-Methyl-1-(naphthalen-2-yl)propan-2-yl]-benzyloxycarboxamide

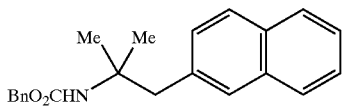

2,2-Dimethyl-3-(naphthalen-2-yl)propionic acid (205.4 g) obtained in Step 10 was dissolved in water (173 ml), triethylamine (131 ml) and acetone (800 ml), and a solution of ethyl chlorocarbonate (101.5 ml) in acetone (400 ml) was added under ice-cooling. A solution of sodium azide (73.1 g) in water (400 ml) was added dropwise, and the reaction mixture was stirred at room temperature for 2 hr. To the reaction mixture were added water (1.5 L) and toluene (1.2 L), and the organic layer was separated from the aqueous layer. The organic layer was washed twice with water and three times with saturated brine, and dried over anhydrous sodium sulfate. After the drying agent was filtered off, the filtrate was heated to 100° C. over 4 hr under an argon atmosphere, and stirred at 100° C. for 1 hr. The reaction mixture was concentrated under reduced pressure and benzyl alcohol (500 ml) was added. The mixture was stirred at 105° C. for 1 day. The reaction mixture was concentrated under reduced pressure, and ethyl acetate and n-hexane were added to the obtained residue. The solution was treated with activated carbon and concentrated under reduced pressure, and the obtained residue was purified by silica gel column chromatography (n-hexane:ethyl acetate=20:1) to give the title compound (240.5 g).
$^1$H-NMR(300 MHz, δppm, CDCl$_3$) 8.83–7.78(1H,m), 7.71–7.66(2H,m), 7.45–7.36(7H,m), 7.22(1H,dd,J=1.6, 8.4 Hz), 5.13(2H,s), 4.54(1H,br s), 3.15(2H,s), 1.34(6H,s). MS(FAB,m/z) 334(M+H)$^+$.

Step 12
[2-Methyl-1-(naphthalen-2-yl)propan-2-yl]amine

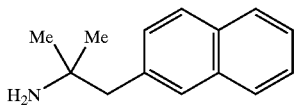

Palladium hydroxide on carbon (19.7 g) was suspended in methanol (500 ml), to the suspension was added a solution of N-[2-methyl-1-(naphthalen-2-yl)propan-2-yl]-benzyloxycarboxamide (237.6 g) obtained in Step 11 in methanol (2 L), and a hydrogenation reaction was performed at room temperature overnight. After filtration of the reaction mixture, the filtrate was concentrated under reduced pressure. To the obtained residue was added ethyl acetate, and to the solution was added conc. hydrochloric acid (70 ml) to give crystals. The obtained crystals were suspended in water, and after an addition of 4N aqueous sodium hydroxide solution (350 ml), the mixture was extracted with ethyl acetate. The ethyl acetate layer was dried over anhydrous sodium sulfate and concentrated under reduced pressure to give crystals of the title compound (138 g).

Step 13
(2R)-1-[1,1-Dimethyl-2-(naphthalen-2-yl)ethylamino]-3-[(cyclopropyl)(2-methoxyphenyl)methoxy]propan-2-ol

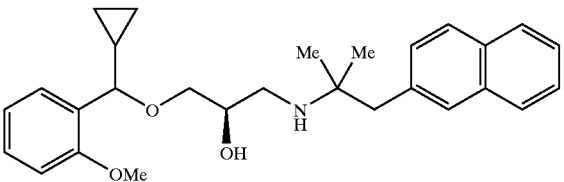

(R)-2-[(Cyclopropyl)(2-methoxyphenyl) methoxymethyl]-oxirane (703 mg) obtained in Step 2 was dissolved in ethanol (12 ml). To the solution was added [2-methyl-1-(naphthalen-2-yl)propan-2-yl]amine (120 ml) obtained either in Step 6, 9 or 12, and the reaction mixture was stirred at 60° C. for 20 hr. The reaction mixture was concentrated under reduced pressure, and the obtained residue was purified by silica gel column chromatography (chloroform:methanol=97:3) to give the title compound (954 mg).

1H-NMR(300 MHz, δppm, DMSO-d$_6$) 7.90–7.70(3H,m), 7.67(1H,s), 7.50–7.20(5H,m) 7.00–6.90(2H,m), 4.62(1H,br s), 4.29(1H,d,J=7.0 Hz), 3.77(3H,s), 3.70–3.50(1H,m), 3.30–3.10(2H,m), 2.80–2.50(4H,m), 1.50–0.85(8H,m), 0.50–0.20(4H,m). MS(APCI,m/z) 433(M+H)$^+$.

Example 2

(2R)-1-[1,1-Dimethyl-2-(naphthalen-2-yl)ethylamino]-3-[(cyclopropyl)(2-methylphenyl)methoxy]propan-2-ol Step 1

(Cyclopropyl)(2-methylphenyl)methanol

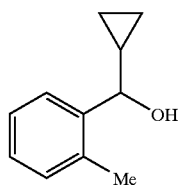

Employing the same procedure described in Step 1 of Example 1, the title compound (5.36 g) was obtained using o-tolualdehyde (4.81 g) instead of o-anisaldehyde.

$^1$H-NMR(300 MHz, δppm, DMSO-d$_6$) 7.43(1H,d, J=7.2 Hz), 7.18–7.10(3H,m), 4.95(1H,d,J=4.8 Hz), 4.36(1H,dd,J=4.4, 6.5 Hz), 2.31(3H,s), 1.20–1.07(1H,m), 0.47–0.20(4H,m). MS(APCI,m/z) 145(M+H—H$_2$O)$^+$.

Step 2

(R)-2-[(Cyclopropyl)(2-methylpheny)methoxymethyl]oxirane

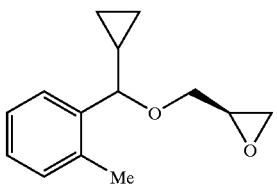

Employing the same procedure described in Step 2 of Example 1, the title compound (1.53 g) was obtained from (cyclopropyl)(2-methylpheny)methanol (3.25 g) obtained in Step 1.

Step 3

(2R)-1-[1,1-Dimethyl-2-(naphthalen-2-yl)ethylamino]-3-[(cyclopropyl)(2-methylpheny)methoxy]propan-2-ol

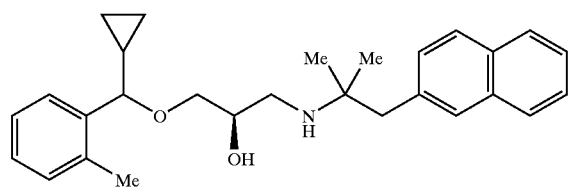

Employing the same procedure described in Step 13 of Example 1, the title compound (849 mg) was obtained from (R)-2-[(cyclopropyl)(2-methylphenyl)methoxymethyl]oxirane (655 mg) obtained in Step 2.

$^1$H-NMR(300 MHz, δppm, DMSO-d$_6$) 7.90–7.70(3H,m), 7.67(1H,s), 7.50–7.25(4H,m) 7.20–7.10(3H,m), 4.65(1H,br s), 4.06(1H,d,J=7.4 Hz), 3.70–3.50(1H,m), 3.30–3.10(2H, m), 2.80–2.50(4H,m), 2.31(3H,s), 1.50–0.80(8H,m), 0.60–0.10(4H,m). MS(APCI,m/z) 417(M+H)$^+$.

Example 3

(2R)-1-[1,1-Dimethyl-2-(naphthalen-2-yl)ethylamino]-3-[(cyclopropyl)(phenyl)methoxy]propan-2-ol Step 1

(R)-2-[(Cyclopropyl)(phenyl)methoxymethyl]oxirane

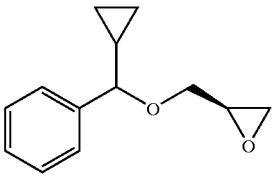

In the same manner as in Step 2 of Example 1, the title compound (296 mg) was obtained from u-cyclopropylbenzyl alcohol (740 mg).

Step 2

(2R)-1-[1,1-Dimethyl-2-(naphthalen-2-yl)ethylamino]-3-[(cyclopropyl)(phenyl)methoxy]propan-2-ol

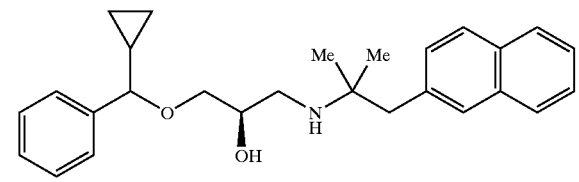

In the same manner as in Step 13 of Example 1, the title compound (334 mg) was obtained from (R)-2-[(cyclopropyl)(phenyl)methoxymethyl]oxirane (204 mg) obtained in Step 1.

$^1$H-NMR(300 MHz, δppm, DMSO-d$_6$) 7.90–7.70(3H,m), 7.67(1H,s), 7.50–7.20(8H,m) 4.65(1H,br s), 3.80–3.50(2H, m), 3.30–3.10(2H,m), 2.80–2.50(4H,m), 1.50–0.80(8H,m), 0.60–0.10(4H,m). MS(APCI,m/z) 403(M+H)$^+$.

Example 4

(2R)-1-[1,1-Dimethyl-2-(naphthalen-2-yl)ethylamino]-3-[1-(2-methoxyphenyl)ethoxy]propan-2-ol Step 1

1-(2-Methoxyphenyl)ethanol

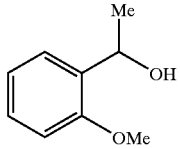

Lithium aluminum hydride (1.52 g) was suspended in tetrahydrofuran (100 ml), 2'-methoxyacetophenone (2.76 ml) was added under ice-cooling, and the mixture was stirred for 30 min. To the reaction mixture were successively added water (1.5 ml), 15% aqueous sodium hydroxide solution (1.5 ml) and water (4.5 ml). The organic layer was dried over magnesium sulfate and concentrated under reduced pressure to give the title compound (3.05 g).

Step 2

(R)-2-[1-(2-Methoxyphenyl)ethoxymethyl]oxirane

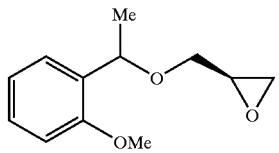

In the same manner as in Step 2 of Example 1, the title compound (123 mg) was obtained from 1-(2-methoxyphenyl)ethanol (837 mg) obtained in Step 1.

Step 3

(2R)-1-[1,1-Dimethyl-2-(naphthalen-2-yl)ethylamino]-3-[1-(2-methoxyphenyl)ethoxy]propan-2-ol

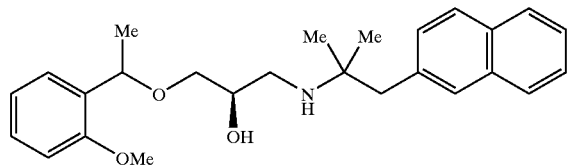

In the same manner as in Step 13 of Example 1, the title compound (148 mg) was obtained from (R)-2-[1-(2-methoxyphenyl)ethoxymethyl]oxirane(115 mg) obtained in Step 2.

$^1$H-NMR(300 MHz, δppm, DMSO-$d_6$) 7.85–7.70(3H,m), 7.61(1H,s), 7.50–7.20(5H,m), 7.00–6.80(2H,m), 4.88(1H,q, J=6.4 Hz), 3.85–3.75(4H,m), 3.45–3.35(2H,m), 2.85–2.60 (4H,m), 1.40–1.37(3H,m), 1.10–1.08(6H,m). MS(APCI,m/z) 408(M+H)$^+$.

(2R)-1-[1,1-Dimethyl-2-(naphthalen-2-yl)ethylamino]-3-[1-(2-methoxyphenyl)ethoxy]propan-2-ol hydrochloride

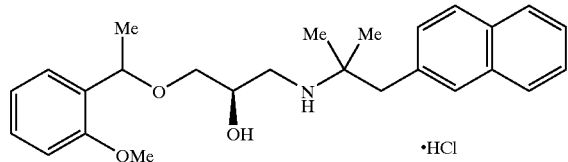

(2R)-1-[1,1-Dimethyl-2-(naphthalen-2-yl)ethylamino]-3-[1-(2-methoxyphenyl)ethoxy]propan-2-ol (141 mg) obtained in Example 4 was dissolved in diethyl ether (5 ml), and 4N hydrogen chloride-ethyl acetate solution was added. The reaction mixture was concentrated under reduced pressure and diethyl ether (5 ml) was added. The mixture was concentrated under reduced pressure to give the title compound (154 mg).

$^1$H-NMR(300 MHz, δppm, DMSO-$d_6$) 8.91(1H,br s), 8.54(1H,br s), 7.95–7.86(3H,m), 7.67(1H,s), 7.55–7.45(2H, m), 7.40–7.20(3H,m), 7.02–6.93(2H,m), 5.66–5.61(1H,m), 4.90–4.80(1H,m), 4.05–3.95(1H,m), 3.80(3H,s), 3.40–3.10 (5H,m), 3.05–2.85(1H,m), 1.32(3H,d,J=6.4 Hz), 1.09(6H,s). MS(APCI,m/z) 408(M+H—HCl)$^+$.

Example 6

(2R)-1-[1,1-Dimethyl-2-(naphthalen-2-yl)ethylamino]-3-[1-(2-methylphenyl)ethoxy]propan-2-ol Step 1

1-(2-Methylphenyl)ethanol

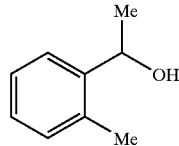

In the same manner as in Step 1 of Example 4, the title compound (755 mg) was obtained from 2'-methylacetophenone (2.68 g).

Step 2

(R)-2-[1-(2-Methylphenyl)ethoxymethyl]oxirane

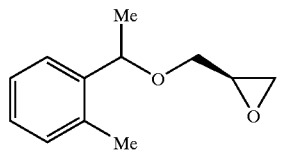

In the same manner as in Step 2 of Example 1, the title compound (123 mg) was obtained from 1-(2-methylphenyl)ethanol (749 mg) obtained in Step 1.

Step 3

(2R)-1-[1,1-Dimethyl-2-(naphthalen-2-yl)ethylamino]-3-[1-(2-methylphenyl)ethoxy]propan-2-ol

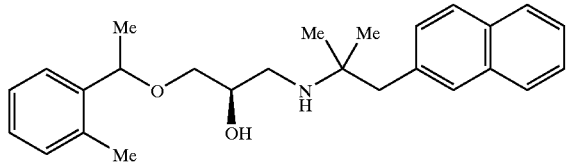

In the same manner as in Step 13 of Example 1, the title compound (345 mg) was obtained from (R)-2-[1-(2-methylphenyl)ethoxymethyl]oxirane (192 mg) obtained in Step 2.

$^1$H-NMR(300 MHz, δppm, CDCl$_3$) 7.85–7.70(3H,m), 7.60(1H,s), 7.50–7.10(7H,m), 4.75–4.65(1H,m), 3.80–3.70 (1H,m), 3.40–3.30(2H,m), 2.90–2.60(4H,m), 2.31(3H,s), 1.39(3H,d,J=6.4 Hz), 1.10–1.07(6H,m). MS(APCI,m/z) 392 (M+H)$^+$.

Example 7

(2R)-1-[1,1-Dimethyl-2-(naphthalen-2-yl)ethylamino]-3-[1-(2-methylphenyl)ethoxy]propan-2-ol hydrochloride

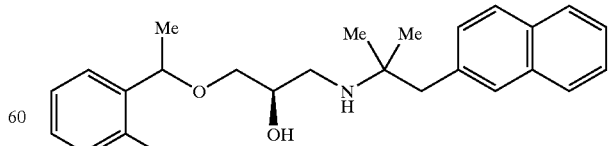

In the same manner as in Example 5, the title compound (337 mg) was obtained from (2R)-1-[1,1-dimethyl-2-(naphthalen-2-yl)ethylamino]-3-[1-(2-methylphenyl)ethoxy]propan-2-ol (339 mg) obtained in Example 6.

¹H-NMR(300 MHz, δppm, DMSO-d₆) 8.97(1H,br s), 8.56(1H,br s), 7.95–7.85(3H,m), 7.77(1H,s), 7.75–7.65(2H, m), 7.40–7.32(2H,m), 7.25–7.12(3H,m), 5.66–5.61(1H,m), 4.73(1H,q,J=6.3 Hz), 4.10–3.95(1H,br s), 3.40–3.10(5H,m), 3.05–2.90(1H,m), 2.31(3H,s), 1.34(3H,d,J=6.6 Hz), 1.27 (3H,s), 1.26(3H,s). MS(APCI,m/z) 392(M+H—HCl)⁺.

Example 8

(2R)-1-[1,1-Dimethyl-2-(naphthalen-2-yl)ethylamino]-3-[1-(2-methoxyphenyl)propoxy]propan-2-ol Step 1

1-(2-Methoxyphenyl)propanol

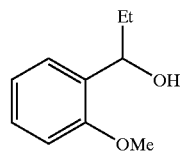

o-Anisaldehyde (2.72 g) was dissolved in tetrahydrofuran (50 ml), and 0.93M magnesium ethylbromide-tetrahydrofuran solution (31.3 ml) was added dropwise under ice-cooling over 10 min. The mixture was stirred at room temperature for 2 hr. The reaction mixture was ice-cooled, and saturated aqueous ammonium chloride solution (40 ml) and water (40 ml) were added and the mixture was extracted with ethyl acetate. The organic layer was washed with saturated brine, dried over magnesium sulfate and concentrated under reduced pressure. The obtained residue was purified by silica gel column chromatography (n-hexane:ethyl acetate=4:1) to give the title compound (3.15 g).

Step 2

(R)-2-[1-(2-Methoxyphenyl)propoxymethyl]oxirane

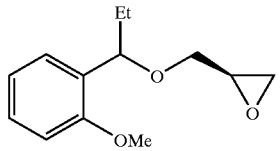

In the same manner as in Step 2 of Example 1, the title compound (264 mg) was obtained from 1-(2-methoxyphenyl)propanol (831 mg) obtained in Step 1.

Step 3

(2R)-1-[1,1-Dimethyl-2-(naphthalen-2-yl)ethylamino]-3-[1-(2-methoxyphenyl)propoxy]propan-2-ol

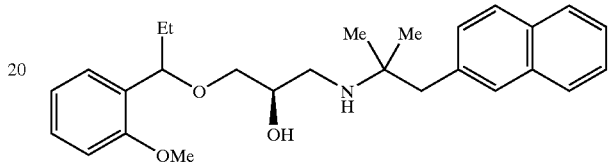

In the same manner as in Step 13 of Example 1, the title compound (403 mg) was obtained from (R)-2-[1-(2-methoxyphenyl)propoxymethyl]oxirane (264 mg) obtained in Step 2.

¹H-NMR(300 MHz, δppm, CDCl₃) 7.85–7.70(3H,m), 7.61(1H,s), 7.50–7.20(5H,m), 7.00–6.90(1H,m), 6.85–6.75 (1H,m), 4.67(1H,t,J=6.3 Hz), 3.85–3.70(4H,m), 3.42–3.27 (2H,m), 2.90–2.65(6H,m), 1.15–1.05(6H,m), 0.91(3H,t,J= 7.4 Hz). MS(APCI,m/z) 422(M+H)⁺.

Example 9–Example 20

In the same manner as in Examples 1–8, the compounds of Example 9–Example 20 were obtained. They are shown in Table 1 and Table 2.

TABLE 1

| | | |
|---|---|---|
| Ex. 9 | 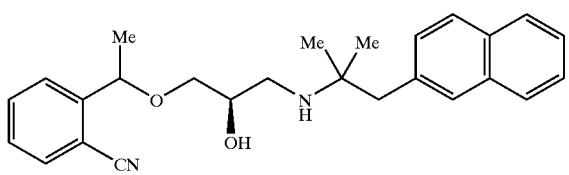 | ¹H-NMR(300 MHz, δ ppm, DMSO-d₆) 7.90–7.30(11H, m), 4.80–4.60(2H, m), 3.75–3.55(1H, m) 3.45–3.25(2H, m), 2.80–2.40(4H, m), 1.45–1.30(3H, m), 1.05–0.90(6H, m). MS(APCI, m/z) 403(M + H)⁺. |
| Ex. 10 | 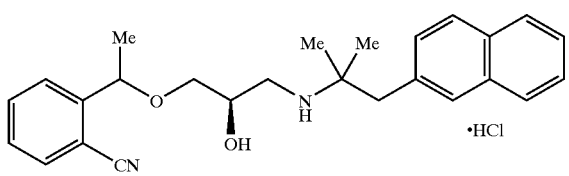 | ¹H-NMR(300 MHz, δ ppm, DMSO-d₆) 9.03 (1H, br s), 8.61(1H, br s), 7.95–7.70(6H, m), 7.65(1H, t, J=6.4 Hz), 7.60–7.40(3H, m), 7.38(1H, d, J=8.4 Hz) 5.75–5.65(1H, m), 4.90–4.70(1H, m), 4.15–3.90(1H, m), 3.50–2.80(6H, m), 1.47(3H, d, J=6.4 Hz), 1.07(6H, s). MS(APCI, m/z) 403(M + H—HCl)⁺. |
| Ex. 11 | 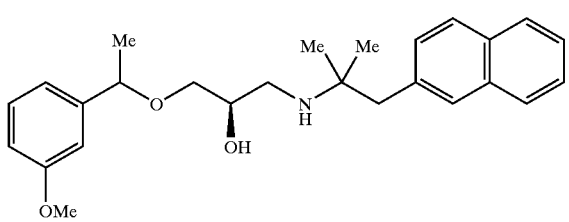 | ¹H-NMR(300 MHz, δ ppm, CDCl₃) 7.85–7.70(3H, m), 7.61(1H, s), 7.50–7.20(5H, m), 7.00–6.80(2H, m), 4.88(1H, q, J=6.4 Hz), 3.85–3.75 (4H, m), 3.45–3.35(2H, m), 2.85–2.60(4H, m), 1.40–1.37(3H, m), 1.10–1.08(6H, m). MS(APCI, m/z) 408(M + H)⁺. |

TABLE 1-continued

| Ex. 12 | 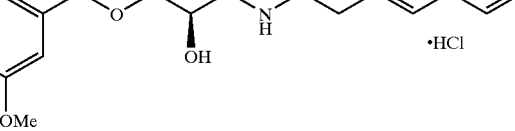 | ¹H-NMR(300 MHz, δ ppm, DMSO-d₆) 8.99 (1H, br s), 8.56(1H, br s), 7.95–7.85(3H, m), 7.76(1H, s), 7.57–7.47(2H, m), 7.42–7.35(1H, m), 7.33–7.23(1H, m), 6.95–6.80(3H, m), 5.61–5.65(1H, m), 4.55–4.42(1H, m), 4.10–3.95(1H, m), 3.76(3H, s), 3.40–3.10(5H, m), 3.00–2.80 (1H, m), 1.37(3H, d, J=6.6 Hz), 1.09(6H, s). MS(APCI, m/z) 408(M + H—HCl)⁺. |
|---|---|---|
| Ex. 13 | 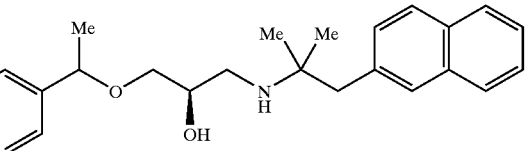 | ¹H-NMR(300 MHz, δ ppm, CDCl₃) 7.85–7.70(3H, m), 7.60(1H, m), 7.50–7.40(2H, m), 7.35–7.15(2H, m), 7.10–7.00(3H, m), 4.45–4.35(1H, m), 3.80–3.70(1H, m), 3.35–3.25(2H, m), 2.85–2.60(4H, m), 2.34(3H, s), 1.43–1.40(3H, m), 1.10–1.07(6H, m). MS(APCI, m/z) 392(M + H)⁺. |
| Ex. 14 | 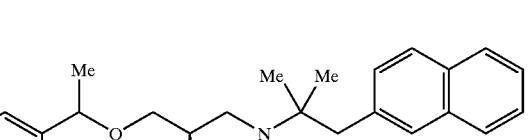 | ¹H-NMR(300 MHz, δ ppm, DMSO-d₆) 9.03 (1H, br s), 8.57(1H, br s), 7.95–7.85(3H, m), 7.76(1H, s), 7.57–7.45(2H, m), 7.41–7.33(1H, m), 7.30–7.20(1H, m), 7.18–7.07(3H, m), 5.65–5.62(1H, m), 4.50–4.40(1H, m), 4.08–3.92(1H, m), 3.40–3.08(5H, m), 3.00–2.80(1H, m), 2.32 (3H, s), 1.36(3H, d, J=6.4 Hz), 1.26(6H, s). MS(APCI, m/z) 392(M + H—HCl) |
| Ex. 15 |  | ¹H-NMR(300 MHz, δ ppm, CDCl₃) 7.85–7.70(3H, m), 7.60(1H, s), 7.50–7.40(2H, m), 7.35–7.20(6H, m), 4.45–4.35(1H, m), 3.80–3.70(1H, m), 3.40–3.25(2H, m), 2.90–2.60(4H, m), 1.43 (3H, d, J=6.5 Hz), 1.10–1.06(6H, m). MS(APCI, m/z) 378(M + H)⁺. |

TABLE 2

| Ex. 16 | 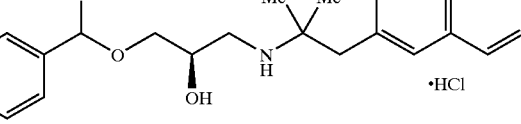 | ¹H-NMR(300 MHz, δ ppm, DMSO-d₆) 8.99 (1H, br s), 8.56(1H, br s), 7.90–7.87(m, 3H), 7.77(1H, s), 7.55–7.48(2H, m), 7.40–7.27(6H, m), 5.63(1H, t, J=5.1 Hz), 4.52–4.48(1H, m), 4.08–3.93(1H, m), 3.40–2.80(6H, m), 1.37(3H, d, J=6.3 Hz), 1.27(3H, s), 1.26(3H, s). MS(APCI, m/z) 378(M + H—HCl)⁺. |
|---|---|---|
| Ex. 17 |  | ¹H-NMR(300 MHz, δ ppm, DMSO-d₆) 8.97 (1H, br s), 8.59(1H, br s), 7.95–7.85(3H, m), 7.77(1H, s), 7.57–7.47(2H, m), 7.45–7.22(3H, m), 7.05–6.95(2H, m), 5.64–5.59(1H, m), 4.66 (1H, t, J=6.0 Hz), 4.10–3.95(1H, m), 3.80(3H, s), 3.35–3.10(5H, m), 3.05–2.85(1H, m), 1.70–1.55 (2H, m), 1.27(6H, s), 0.92–0.82(3H, m). MS(APCI, m/z) 422(M + H–HCl)⁺. |
| Ex. 18 | 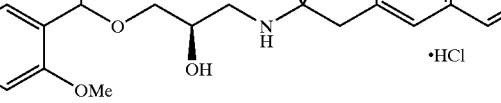 | ¹H-NMR(300 MHz, δ ppm, DMSO-d₆) 9.09 (1H, br s), 8.61(1H, br s), 7.92–7.88(3H, m), 7.78(1H, s), 7.60–7.45(2H, m), 7.40–7.20(6H, m), 5.65–5.55(1H, m), 4.30–4.20(1H, m), 4.15–3.90(1H, m), 3.40–2.80(6H, m), 1.85–1.52(2H, m), 1.27(6H, s), 0.90–0.75(3H, m). MS(APCI, m/z) 392(M + H—HCl)⁺. |

TABLE 2-continued

| Ex. 19 | 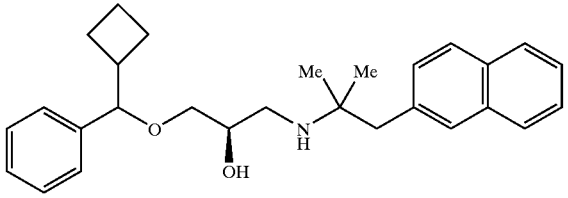 | ¹H-NMR(300 MHz, δ ppm, CDCl₃) 7.85–7.70(3H, m), 7.61(1H, s), 7.50–7.40(2H, m), 7.35–7.20(6H, m), 4.15–4.05(1H, m), 3.80–3.70(1H, m), 3.40–3.20(2H, m), 2.90–2.45(5H, m), 2.10–1.60(6H, m), 1.10–1.00(6H, m). MS(APCI, m/z) 418(M + H)⁺. |
|---|---|---|
| Ex. 20 | 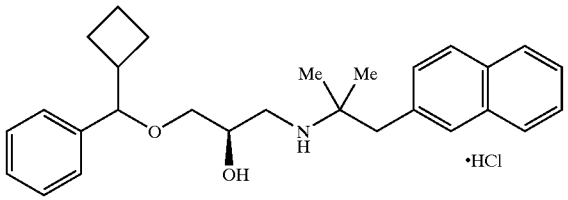 | ¹H-NMR(300 MHz, δ ppm, DMSO-d₆) 8.90 (1H, m), 8.56(1H, m), 7.92–7.80(3H, m), 7.77 (1H, s), 7.55–7.45(2H, m), 7.40–7.22(6H, m), 5.61–5.54(1H, m), 4.26(1H, d, J=8.4 Hz), 4.02 (1H,br s), 3.40–2.80(6H, m), 2.05–1.92(2H, m), 1.83–1.60(5H, m), 1.26(6H, s). MS(APCI, m/z) 418(M + H—HCl)⁺. |

Example 21

(2R)-1-[1,1-Dimethyl-2-(naphthalen-2-yl)ethylamino]-3-[(1R)-1-(2-methoxyphenyl)ethoxy]propan-2-ol Step 1

(R)-1-(2-Methoxyphenyl)ethanol

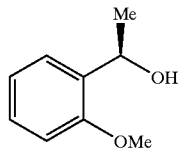

To a solution of (+)-B-chlorodiisopinocampheylborane (10.5 g) in tetrahydrofuran (50 ml) was added dropwise 2'-methoxyacetophenone (10.5 g) at −25° C. The mixture was stirred at −25° C. for 1 hr and concentrated under reduced pressure. To the residue were added diethyl ether (100 ml) and diethanolamine (18.1 g) and the reaction mixture was stirred at room temperature for 2 hr. The precipitated solid was filtered off. The filtrate was concentrated under reduced pressure and purified by distillation under reduced pressure (bp 74–77° C./1 mmHg) to give the title compound (8.00 g).

Step 2

(R)-2-[(1R)-1-(2-Methoxyphenyl)ethoxymethyl]oxirane

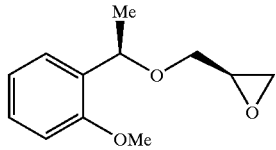

In the same manner as in Step 2 of Example 1, the title compound (930 mg) was obtained from (R)-1-(2-methoxyphenyl)ethanol (1.52 g) obtained in Step 1.

Step 3

(2R)-1-[1,1-Dimethyl-2-(naphthalen-2-yl)ethylamino]-3-[(1R)-1-(2-methoxyphenyl)ethoxy]propan-2-ol

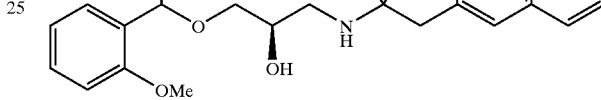

In the same manner as in Step 13 of Example 1, the title compound (770 mg) was obtained from (R)-2-[(1R)-1-(2-methoxyphenyl)ethoxymethyl]oxirane (417 mg) obtained in Step 2.

¹H-NMR(300 MHz, δppm, CDCl₃) 7.85–7.70(3H,m), 7.61(1H,s), 7.50–7.20(5H,m), 7.00–6.80(2H,m), 4.88(1H,q, J=6.5 Hz), 3.85–3.75(4H,m), 3.38(2H,d,J=5.1 Hz), 2.90–2.60(4H,m), 1.38(3H,d,J=6.6 Hz), 1.10(3H,s), 1.07 (3H,s). MS(APCI,m/z) 408(M+H)⁺.

Example 22

(2R)-1-[1,1-Dimethyl-2-(naphthalen-2-yl)ethylamino]-3-[(1R)-1-(2-methoxyphenyl)ethoxy]propan-2-ol hydrochloride

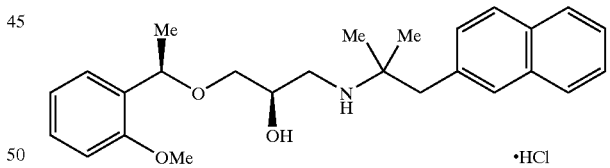

In the same manner as in Example 5, the title compound (810 mg) was obtained from (2R)-1-[1,1-dimethyl-2-(naphthalen-2-yl)ethylamino]-3-[(1R)-1-(2-methoxyphenyl)ethoxy]propan-2-ol obtained in Example 21.

¹H-NMR(300 MHz, δppm, DMSO-d₆) 8.94(1H,br s), 8.56(1H,br s), 7.95–7.85(3H, m), 7.77(1H,s), 7.57–7.45(2H, m), 7.42–7.20(3H,m), 7.05–6.95(2H,m), 5.61(1H,d,J=4.8 Hz), 4.84(1H,q,J=6.3 Hz), 4.10–3.95(1H,m), 3.80(3H,s), 3.40–3.10(5H,m), 3.00–2.85(1H,m), 1.32(3H,d,J=6.3 Hz), 1.26(6H,s). MS(APCI,m/z) 408(M+H—HCl)⁺.

Example 23

(2R)-1-[1,1-Dimethyl-2-(naphthalen-2-yl)ethylamino]-3-[(1R)-(cyclopropyl)(2-methylphenyl)methoxy]propan-2-ol Step 1
N-Methoxy-2, N-dimethylbenzamide

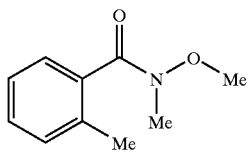

To a solution of o-toluyl chloride (3.09 g) and triethylamine (5.58 ml) in dichloromethane (150 ml) was added N,O-dimethylhydroxylamine hydrochloride (3.90 g) under ice-cooling and the obtained mixture was stirred at room temperature for 12 hr. The reaction mixture was concentrated under reduced pressure, and the residue was diluted with ethyl acetate, washed successively with 1N hydrochloric acid, water, a saturated aqueous sodium hydrogencarbonate solution and saturated brine. The organic layer was dried over anhydrous sodium sulfate and concentrated under reduced pressure to give the title compound (3.58 g).

Step 2
Cyclopropyl 2-methylpheny ketone

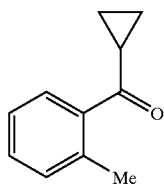

To a solution of N-methoxy-2,N-dimethylbenzamide (3.55 g) obtained in Step 1 in tetrahydrofuran (40 ml) was added dropwise a solution of 1M cyclopropylmagnesium bromide-tetrahydrofuran (29.7 ml) under ice-cooling, and the mixture was stirred at room temperature for 12 hr. To the reaction mixture was added a 4N hydrogen chloride-ethyl acetate solution (10 ml), and the resulting mixture was concentrated under reduced pressure. The residue was diluted with ethyl acetate, washed successively with 1N hydrochloric acid, water, saturated sodium hydrogencarbonate and saturated brine, dried over anhydrous sodium sulfate, and concentrated under reduced pressure. The residue was purified by silica gel column chromatography (ethyl acetate:hexane=1:5) to give the title compound (1.05 g).

Step 3
(R)-(Cyclopropyl)(2-methylphenyl)methanol

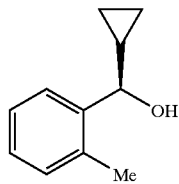

To a suspension of dichloro[(S)-(−)-2,2'-bis(diphenylphosphino)-1,1'-binaphthyl]ruthenium(II) (851 mg), (1S,2S)-(−)-1,2-diphenylethylenediamine (191 mg) and potassium-tert-butoxide (270 mg) in isopropanol (90 ml) was added cyclopropyl 2-methylphenyl ketone (9.61 g) obtained in Step 2, and the mixture was hydrogenated at room temperature and at medium pressure (3.0 kgf/cm²) for 60 hr. The reaction mixture was concentrated under reduced pressure, and the residue was purified by silica gel column chromatography (ethyl acetate:hexane=1:9) to give the title compound (6.92 g).

$^1$H-NMR(300 MHz, δppm, DMSO-$d_6$) 7.43(1H,d,J=6.8 Hz), 7.18–7.09(3H,m), 4.97(1H,d,J=4.6 Hz), 4.36(1H,dd,J=4.6, 6.4 Hz), 2.30(3H,s), 1.17–1.07(1H,m), 0.41–0.24(4H, m). MS(APCI,m/z) 145(M+H—$H_2O$)$^+$.

Step 4
(R)-2-[(1R)-(Cyclopropyl)(2-methylphenyl)methoxymethyl]oxirane

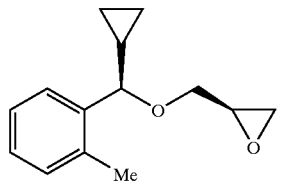

Employing the same procedure described in Step 2 of Example 1, the title compound (1.80 g) was obtained from (R)-(cyclopropyl)(2-methylpheny)methanol (3.24 g) obtained in Step 3.

Step 5
(2R)-1-[1,1-Dimethyl-2-(naphthalen-2-yl)ethylamino]-3-[(1R)-(cyclopropyl)(2-methylphenyl)methoxy]propan-2-ol

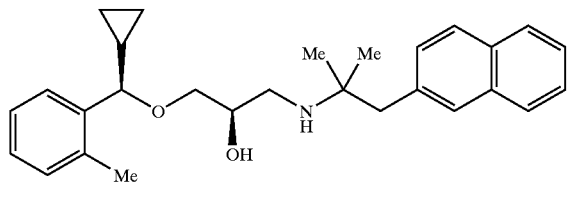

Employing the same procedure described in Step 13 of Example 1, the title compound (1.17 g) was obtained from (R)-2-[(1R)-(cyclopropyl)(2-methylpheny)methoxymethyl]oxirane (655 mg) obtained in Step 4.

$^1$H-NMR(300 MHz, δppm, DMSO-$d_6$) 7.90–7.70(3H,m), 7.66(1H,s), 7.50–7.25(4H,m) 7.20–7.10(3H,m), 4.64(1H,br s), 4.06(1H,d,J=7.4 Hz), 3.70–3.50(1H,m), 3.30–3.10(2H, m), 2.80–2.50(4H,m), 2.31(3H,s), 1.50–0.85(2H,m), 0.60–0.10(4H,m). MS(APCI,m/z) 417(M+H)$^+$.

Example 24

(2R)-1-[1,1-Dimethyl-2-(naphthalen-2-yl)ethylamino]-3-[(1R)-(cyclopropyl)(2-methoxyphenyl)methoxy]propan-2-ol Step 1
2,N-Dimethoxy-N-methylbenzamide

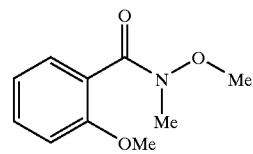

In the same manner as in Step 1 of Example 23, the title compound (3.56 g) was obtained from 2-methoxybenzoyl chloride (3.41 g).

Step 2
Cyclopropyl 2-methoxyphenyl ketone

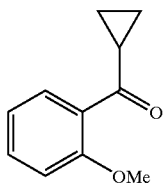

In the same manner as in Step 2 of Example 23, the title compound (2.27 g) was obtained from 2,N-dimethoxy-N-methylbenzamide (3.55 g) obtained in Step 1.

¹H-NMR(300 MHz, δppm, CDCl₃) 7.59(1H,dd,J=7.5, 1.7 Hz), 7.48–7.42(1H,m), 7.02–6.97(2H,m), 3.91(3H,s), 2.77–2.68(1H,m), 1.25–1.20(2H,m), 1.01–0.95(1H,m). MS(ESI,m/z) 177(M+H)⁺.

Step 3
(R)-(Cyclopropyl)(2-methoxyphenyl)methanol

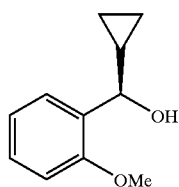

In the same manner as in Step 3 of Example 23, the title compound (3.55 g) was obtained from cyclopropyl 2-methoxyphenyl ketone (3.52 g) obtained in Step 2.

¹H-NMR(300 MHz, δppm, CDCl₃) 7.40(1H,dd,J=1.6, 7.5 Hz), 7.26(1H,dt,J=1.7, 7.8 Hz), 7.00–6.89(2H,m), 4.20(1H, br d,J=8.4 Hz), 3.87(3H,s), 2.83(1H,br s), 1.42–1.30(1H,m), 0.70–0.61(1H,m), 0.57–0.44(2H,m), 0.37–0.27(1H,m). MS(ESI,m/z) 161(M+H—H₂O)⁺.

Step 4
(R)-2-[(1R)-(Cyclopropyl)(2-methoxyphenyl)methoxymethyl]oxirane

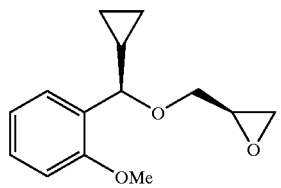

In the same manner as in Step 2 of Example 1, the title compound (840 mg) was obtained from (R)-(cyclopropyl)(2-methoxyphenyl)methanol (1.78 g) obtained in Step 3.

Step 5
(2R)-1-[1,1-Dimethyl-2-(naphthalen-2-yl)ethylamino]-3-[(1R)-(cyclopropyl)(2-methoxyphenyl)methoxy]propan-2-ol

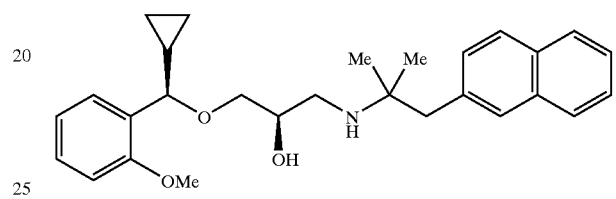

In the same manner as in Step 13 of Example 1, the title compound (970 mg) was obtained from (R)-2-[(1R)-(cyclopropyl)(2-methoxyphenyl)methoxymethyl]oxirane (586 mg) obtained in Step 4.

¹H-NMR(300 MHz, δppm, CDCl₃) 7.83–7.70(3H,m), 7.61(1H,s), 7.50–7.37(3H,m), 7.35–7.20(2H,m), 7.00–6.82 (2H,m), 4.28(1H,d,J=7.8 Hz), 3.83–3.70(4H,m), 3.42–3.30 (2H,m), 2.90–2.60(4H,m), 1.25–1.10(7H,m), 0.60–0.50(1H, m), 0.45–0.30(3H,m). MS(APCI,m/z) 434(M+H)⁺.

Example 25–Example 56

In the same manner as in Examples 1–24, the compounds of Example 25–Example 56 were obtained. They are shown in Table 3–Table 7.

TABLE 3

| Ex. 25 | 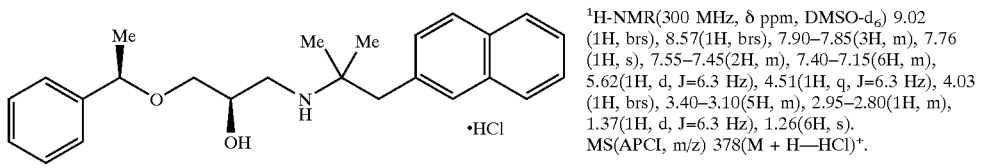 | ¹H-NMR(300 MHz, δ ppm, DMSO-d₆) 9.02 (1H, brs), 8.57(1H, brs), 7.90–7.85(3H, m), 7.76 (1H, s), 7.55–7.45(2H, m), 7.40–7.15(6H, m), 5.62(1H, d, J=6.3 Hz), 4.51(1H, q, J=6.3 Hz), 4.03 (1H, brs), 3.40–3.10(5H, m), 2.95–2.80(1H, m), 1.37(1H, d, J=6.3 Hz), 1.26(6H, s). MS(APCI, m/z) 378(M + H—HCl)⁺. |
|---|---|---|
| Ex. 26 | 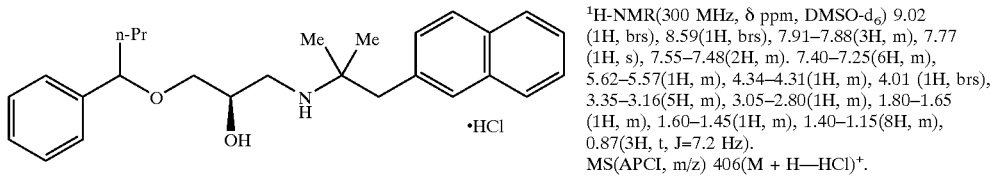 | ¹H-NMR(300 MHz, δ ppm, DMSO-d₆) 9.02 (1H, brs), 8.59(1H, brs), 7.91–7.88(3H, m), 7.77 (1H, s), 7.55–7.48(2H, m). 7.40–7.25(6H, m), 5.62–5.57(1H, m), 4.34–4.31(1H, m), 4.01 (1H, brs), 3.35–3.16(5H, m), 3.05–2.80(1H, m), 1.80–1.65 (1H, m), 1.60–1.45(1H, m), 1.40–1.15(8H, m), 0.87(3H, t, J=7.2 Hz). MS(APCI, m/z) 406(M + H—HCl)⁺. |
| Ex. 27 | 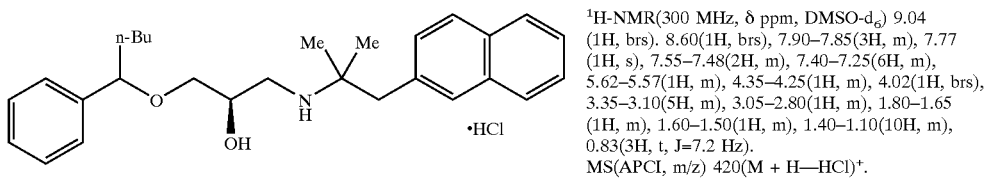 | ¹H-NMR(300 MHz, δ ppm, DMSO-d₆) 9.04 (1H, brs). 8.60(1H, brs), 7.90–7.85(3H, m), 7.77 (1H, s), 7.55–7.48(2H, m), 7.40–7.25(6H, m), 5.62–5.57(1H, m), 4.35–4.25(1H, m), 4.02(1H, brs), 3.35–3.10(5H, m), 3.05–2.80(1H, m), 1.80–1.65 (1H, m), 1.60–1.50(1H, m), 1.40–1.10(10H, m), 0.83(3H, t, J=7.2 Hz). MS(APCI, m/z) 420(M + H—HCl)⁺. |

TABLE 3-continued

| Ex. 28 | [structure: 1-phenyl-1-(but-3-enyloxy) group connected via CH2-CH(OH)-CH2-NH-C(Me)2-CH2-naphthalen-2-yl · HCl] | ¹H-NMR(300 MHz, δ ppm, DMSO-d₆) 8.98 (1H, brs), 8.58(1H, brs), 7.95–7.85(3H, m), 7.77 (1H, s), 7.55–7.45(2H, m), 7.40–7.25(6H, m), 5.85–5.70(1H, m), 5.63–5.58(1H, m), 4.41(1H, t, J=6.6 Hz), 4.01(1H, brs), 3.40–3.10(8H, m), 3.00–2.85(1H, m), 2.45–2.30(1H, m), 1.27(3H, s), 1.26(3H, s). MS(APCI, m/z) 404(M + H–HCl)⁺. |
|---|---|---|
| Ex. 29 | [structure: 1,3-diphenylpropyl ether analog · HCl] | ¹H-NMR(300 MHz, δ ppm, DMSO-d₆) 8.80 (1H, brs), 8.50(1H, brs), 7.95–7.85(3H, m), 7.76 (1H, s), 7.55–7.45(2H, m), 7.40–7.15(11H, m), 5.65–5.59(1H, m), 4.40–4.30(1H, m), 400(1H, brs), 3.35–3.10(7H, m), 2.75–2.60(1H, m), 2.10–2.00 (1H, m), 2.00–1.80(1H, m), 1.27(3H, s), 1.26 (3H, s). MS(APCI, m/z) 468(M + H—HCl)⁺. |
| Ex. 30 | [structure: 1-phenylallyl ether analog · HCl] | ¹H-NMR(300 MHz, δ ppm, DMSO-d₆) 9.00 (1H, brs), 8.58(1H, brs), 7.95–7.85(3H, m), 7.76 (1H, s), 7.55–7.45(2H, m), 7.40–7.25(6H, m), 6.00–5.85(1H, m), 5.67(1H, d, J=3.9 Hz), 5.35–5.18 (2H, m), 4.89(1H, d, J=6.6 Hz), 4.06(1H, brs), 3.55–3.25(5H, m), 3.05–2.90(1H, m), 1.27(6H, s). MS(APCI, m/z) 390(M + H—HCl)⁺. |

TABLE 4

| Ex. 31 | [structure: 2-methoxy-1-phenylethyl ether analog · HCl] | ¹H-NMR(300 MHz, δ ppm, DMSO-d₆) 8.84 (1H, brs), 8.54(1H, brs), 7.95–7.85(3H, m), 7.77 (1H, s), 7.55–7.45(2H, m), 7.40–7.25(6H, m), 5.64–5.59(1H, m), 4.60–4.50(1H, m), 4.02(1H, brs), 3.60–3.10(11H, m), 1.26(6H, s). MS(APCI, m/z) 408(M + H—HCl)⁺. |
|---|---|---|
| Ex. 32 | [structure: cyclopentyl(phenyl)methyl ether analog · HCl] | ¹H-NMR(300 MHz, δ ppm, DMSO-d₆) 8.90 (1H, brs), 8.56(1H, brs), 7.95–7.88(3H, m), 7.77 (1H, s), 7.55–7.45(2H, m), 7.40–7.20(6H, m), 5.57–5.51(1H, m), 4.07–3.90(2H, m), 3.30–3.10(6H, m), 3.05–2.80(1H, m), 2.20–2.05(1H, m), 1.85–1.70(1H, m), 1.65–1.35(4H, m), 1.30–1.05(8H, m). MS(APCI, m/z) 432(M + H—HCl)⁺. |
| Ex. 33 | [structure: 1-(4-chlorophenyl)ethyl ether analog] | ¹H-NMR(300 MHz, δ ppm, CDCl₃) 7.83–7.73 (3H, m), 7.60(1H, s), 7.50–7.40(2H, m), 7.35–7.20 (5H, m), 4.41–4.35(1H, m), 3.80–3.65(1H, m), 3.40–3.25(2H, m), 2.95–2.55(4H, m), 1.39(3H, d, J=6.5 Hz), 1.25–1.10(6H, m). MS(APCI, m/z) 412(M + H)⁺. |
| Ex. 34 | [structure: 1-(2-chlorophenyl)ethyl ether analog · HCl] | ¹H-NMR(300 MHz, δ ppm, DMSO-d₆) 8.93 (1H, brs), 8.55(1H, brs), 7.95–7.85(3H, m), 7.77 (1H, s), 7.60–7.25(5H, m), 5.70–5.65(1H, m), 4.87(1H, q, J=6.6 Hz), 4.03(1H, brs), 3.45–3.10(7H, m), 3.05–2.90(1H, m), 1.38(3H, d, J=6.3 Hz), 1.27(6H, s). MS(APCI, m/z) 412(M + H—HCl)⁺. |

TABLE 4-continued

| Ex. 35 | 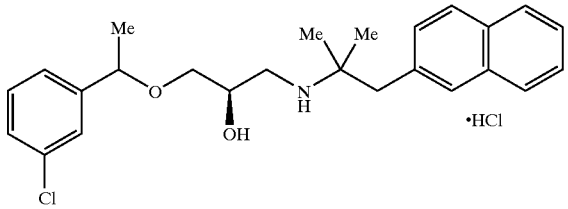 | $^1$H-NMR(300 MHz, δ ppm, DMSO-d$_6$) 9.00 (1H, brs), 8.57(1H, brs), 7.95–7.85(3H, m), 7.77 (1H, s), 7.55–7.25(5H, m), 5.68–5.63(1H, m), 4.54(1H, q, J=6.6 Hz), 4.02(1H, brs), 3.45–3.10(7H, m), 3.05–2.90(1H, m), 1.37(3H, d, J=6.3 Hz), 1.27(6H, s). MS(APCI, m/z) 412(M + H—HCl)$^+$. |
|---|---|---|
| Ex. 36 | 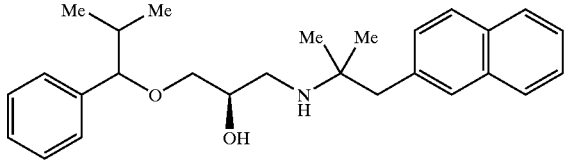 | $^1$H-NMR(300 MHz, δ ppm, CDCl$_3$) 7.85–7.70 (3H, m), 7.61 (1H, s), 7.50–7.40(2H, m), 7.35–7.15(5H, m), 3.85(1H, d, J=7.3 Hz), 3.80–3.70(1H, m), 3.35–3.20(2H, m), 2.90–2.65(4H, m), 2.00–1.85(2H, m), 1.20–1.05(6H, m), 0.99–0.97(3H, m), 0.72–0.69(3H, m). MS(APCI, m/z) 406(M + H)$^+$. |

TABLE 5

| Ex. 37 | 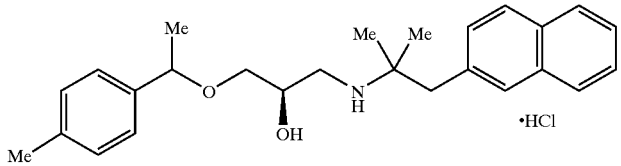 | $^1$H-NMR(300 MHz, δ ppm, DMSO-d$_6$) 8.90 (1H, brs), 8.50(1H, brs), 7.90–7.80(3H, m), 7.76 (1H, s), 7.55–7.45(2H, m), 7.40–7.35(1H, m), 7.25–7.10(4H, m), 5.61(1H, t, J=4.8 Hz), 4.45(1H, q, J=6.2 Hz), 3.97(1H, brs), 3.40–3.10(5H, m), 3.00–2.80(1H, m), 2.29(3H, s), 1.35(3H, d, J=6.4 Hz), 1.26–1.25(6H, m). MS(APCI, m/z) 392(M + H—HCl)$^+$. |
|---|---|---|
| Ex. 38 | 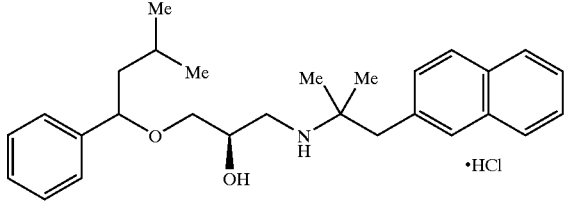 | $^1$H—NMR(300 MHz, δ ppm, DMSO-d$_6$) 8.90 (1H, brs), 8.50(1H, brs), 7.95–7.85(3H, m), 7.76 (1H, s), 7.55–7.45(2H, m), 7.40–7.25(6H, m), 5.62–5.56(1H, m), 4.40–4.30(1H, m), 4.00(1H, brs), 3.40–3.10(5H, m), 3.05–2.80(1H, m), 1.80–1.60 (2H, m), 1.45–1.20(7H, m). 0.90(6H, d, J=6.4 Hz). MS(APCI, m/z) 420(M + H—HCl)$^+$. |
| Ex. 39 | 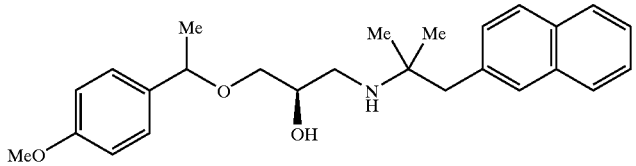 | $^1$H-NMR(300 MHz, δ ppm, CDCl$_3$) 7.85–7.70 (3H, m), 7.76(1H, s), 7.50–7.40(2H, m), 7.30–7.10(3H, m), 6.90–6.80(2H, m), 4.40–4.30(1H, m), 3.80–3.65(4H, m), 3.40–3.25(2H, m), 2.90–2.60 (4H, m), 1.41(3H, d, J=6.5 Hz), 1.10–1.05(6H, m). MS(APCI, m/z) 408(M + H)$^+$. |
| Ex. 40 | 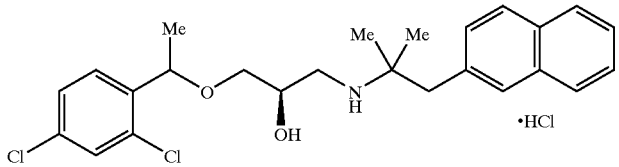 | $^1$H-NMR(300 MHz, δ ppm, DMSO-d$_6$) 8.99 (1H, brs). 8.57(1H, brs), 7.95–7.85(3H, m), 7.76 (1H, s), 7.65–7.45(5H, m), 7.40–7.35(1H, m), 5.75–5.65(1H, m), 4.84(1H, q, J=6.2 Hz), 4.03(1H, br s), 3.40–3.10(5H, m), 3.05–2.85(1H, m), 1.37 (3H, d, J=6.4 Hz), 1.27(6H, s). MS(APCI, m/z) 446(M + H—HCl)$^+$. |
| Ex. 41 | 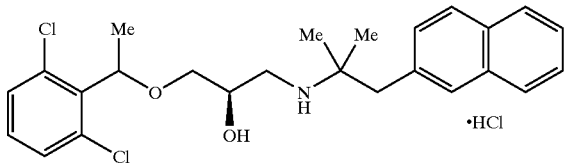 | $^1$H-NMR(300 MHz, δ ppm, DMSO-d$_6$) 8.90 (1H, brs), 8.55(1H, brs), 7.95–7.85(3H, m), 7.76 (1H, s), 7.55–7.45(4H, m), 7.40–7.30(2H, m), 5.70–5.60(1H, m), 5.29(1H, q, J=6.7 Hz), 4.05–3.90 (1H, m), 3.40–2.80(6H, m), 1.25(3H, d, J=5.5 Hz), MS(APCI, m/z) 446(M + H—HCl)$^+$. |

TABLE 5-continued

| Ex. 42 | 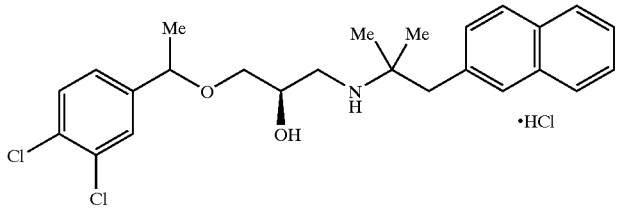 | $^1$H-NMR(300 MHz, δ ppm, DMSO-d$_6$) 8.96 (1H, brs), 8.55(1H, brs), 7.95–7.85(3H, m), 7.76 (1H, s), 7.65–7.60(2H, m), 7.55–7.45(2H, m), 7.40–7.30(2H, m), 5.69–5.65(1H, m), 4.55(1H, q, J32 6.4 Hz), 4.00(1H, brs), 3.45–3.10(5H, m), 3.05–2.85(1H, m). 1.37(3H, d, J=6.4 Hz), 1.26(6H, s). MS(APCI, m/z) 446(M + H—HCl)$^+$. |

TABLE 6

| Ex. 43 | 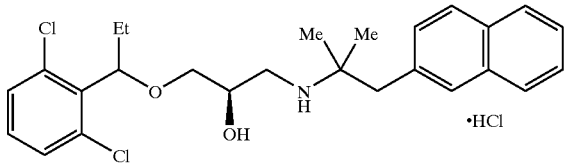 | $^1$H-NMR(300 MHz, δ ppm, DMSO-d$_6$) 8.93 (1H, brs), 8.59(1H, brs), 7.95–7.85(3H, m), 7.77–7.75(1H, m), 7.60–7.30(6H, m), 5.64–5.61(1H, m), 5.07(1H, t, j=8.1 Hz), 4.10–3.95(1H, m), 3.40–3.00(7H, m), 2.90–2.80(1H, m), 2.15–1.80(2H, m), 1.27–1.25(6H, m), 0.95–0.80(3H, m). MS(APCI, m/z) 460(M + H—HCl)$^+$. |
| Ex. 44 | 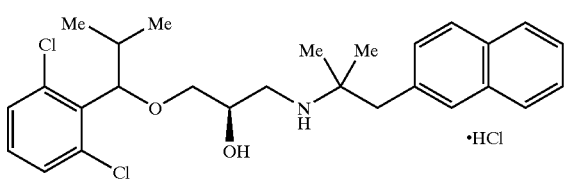 | $^1$H-NMR(300 MHz, δ ppm, DMSO-d$_6$) 8.95 (1H, brs), 8.60(1H, brs), 7.95–7.85(3H, m), 7.75 (1H, s), 7.55–7.45(4H, m), 7.40–7.30(2H, m), 5.62–5.58(1H, m), 4.74–4.70(1H, m), 4.10–3.90(1H, m), 3.40–3.00(6H, m), 2.90–2.80(1H, m), 1.30–1.10(9H, m), 0.67–0.60(3H, m). MS(APCI, m/z) 474(M + H—HCl)$^+$. |
| Ex. 45 | 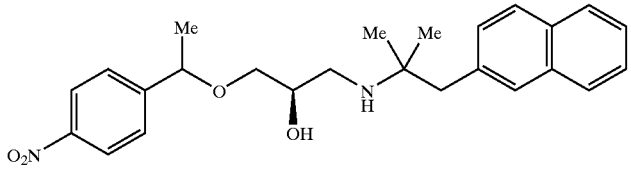 | $^1$H-NMR(300 MHz, δ ppm, CDCl$_3$) 8.20–8.15 (2H, m), 7.85–7.70(3H, m), 7.60(1H, s), 7.50–7.40 (4H, m), 7.35–7.25(1H, m), 4.60–4.50(1H, m), 3.80–3.70(1H, m), 3.45–3.30(2H, m), 2.90–2.75 (3H, m), 2.70–2.60(1H, m), 1.43–1.41(3H, m), 1.12–1.09(6H, m). MS(APCI, m/z) 423(M + H)$^+$. |
| Ex. 46 | 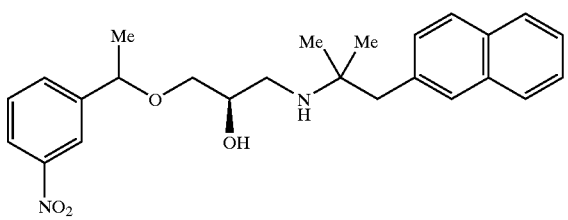 | $^1$H-NMR(300 MHz, δ ppm, CDCl$_3$) 8.20–8.05 (2H, m), 7.80–7.70(3H, m); 7.65–7.55(2H, m), 7.50–7.35(3H, m), 7.35–7.25(1H, m), 4.60–4.45(1H, m), 3.80–3.70(1H, m), 3.50–3.30(2H, m), 2.90–2.60(4H, m), 1.45–1.42(3H, m), 1.12–1.09(6H, m). MS(APCI, m/z) 423(M + H)$^+$. |
| Ex. 47 | 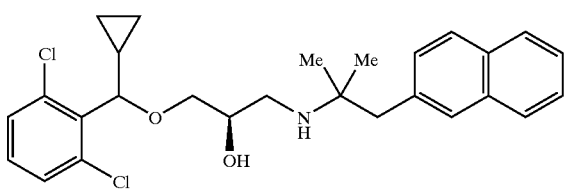 | 7.90–7.70(3H, m), 7.66(1H, d, J=6.8 Hz), 7.50–7.20 (6H, m), 4.65(1H, brs), 4.35(1H, d, J=9.4 Hz), 3.70–3.50(1H, m), 3.40–3.00(2H, m), 2.80–2.40(4H, m), 1.80–0.80(8H, m), 0.80–0.10(4H, m). MS(APCI, m/z) 472(M + H)$^+$. |
| Ex. 48 | 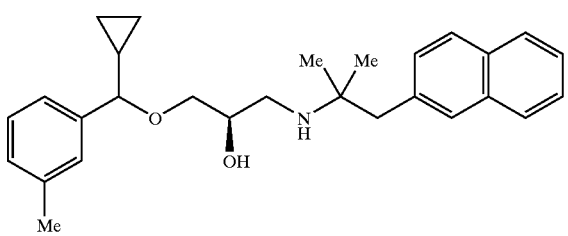 | $^1$H-NMR(300 MHz, δ ppm. DMSO-d$_6$) 7.90–7.70(3H, m), 7.67(1H, s), 7.50–7.30(3H, m), 7.25–7.00(4H, m), 4.64(1H, brs), 3.70–3.50(2H, m), 3.40–3.10(2H, m), 2.80–2.50(4H, m), 2.30(3H, s), 1.50–0.80(8H, m), 0.60–0.10(4H, m). MS(APCI, m/z) 418(M + H)$^+$. |

TABLE 6-continued

| | | |
|---|---|---|
| Ex. 49 | 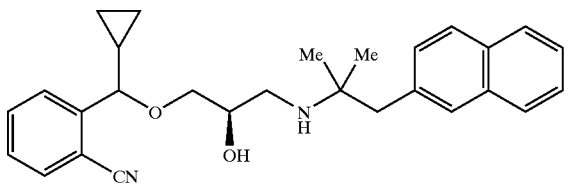 | $^1$H-NMR(300 MHz, δ ppm, DMSO-d$_6$) 7.90–7.30(11H, m), 4.72(1H, brs), 4.10–4.00(1H, m), 3.70–3.55(1H, m), 3.45–3.10(2H, m), 2.80–2.50 (4H, m), 1.50–0.80(8H, m), 0.70–0.20(4H, m). MS(APCI, m/z) 429(M + H)$^+$. |

TABLE 7

| | | |
|---|---|---|
| Ex. 50 | 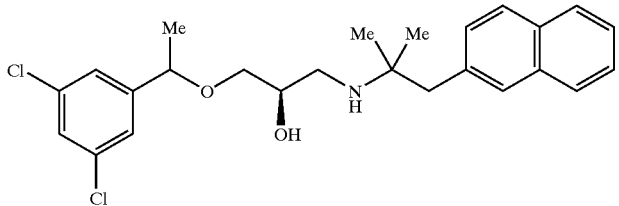 | $^1$H-NMR(300 MHz, δ ppm, CDCl$_3$) 7.85–7.70 (3H, m), 7.61(1H, s), 7.50–7.40(2H, m), 7.35–7.10 (4H, m), 4.40–4.30(1H, m), 3.80–3.70(1H, m), 3.40–3.25(2H, m), 2.90–2.60(4H, m), 1.41–1.37(3H, m), 1.12–1.08(6H, m). MS(APCI, m/z) 446(M + H)$^+$. |
| Ex. 51 | 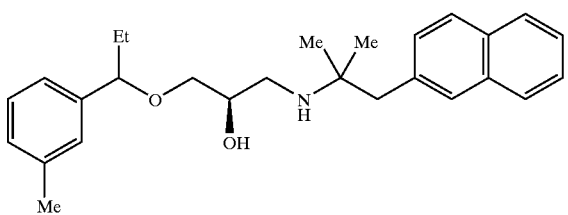 | $^1$H-NMR(300 MHz, δ ppm, CDCl$_3$) 7.85–7.70 (3H, m), 7.60(1H, s), 7.50–7.40(2H, m), 7.35–7.15 (2H, m), 7.10–7.00(3H, m), 4.15–4.05(1H, m), 3.80–3.70(1H, m), 3.45–3.25(2H, m), 2.90–2.60(4H, m), 2.34(3H, s), 1.90–1.60(2H, m), 1.15–1.05 (6H, m), 0.85(3H, t, j=7.4 Hz). MS(APCI, m/z) 406(M + H)$^+$. |
| Ex. 52 | 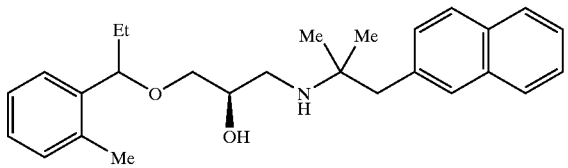 | $^1$H-NMR(300 MHz, δ ppm, CDCl$_3$) 7.85–7.70 (3H, m), 7.60(1H, s), 7.50–7.40(2H, m), 7.35–7.05 (5H, m), 4.50–4.40(1H, m), 3.80–3.70(1H, m), 3.40–3.20(2H, m), 2.90–2.60(4H, m), 2.31(3H, s), 1.80–1.60(2H, m), 1.15–1.05(6H, m), 0.92(3H, t, J=7.2 Hz). MS(APCI, m/z) 406(M + H)$^+$. |
| Ex. 53 | 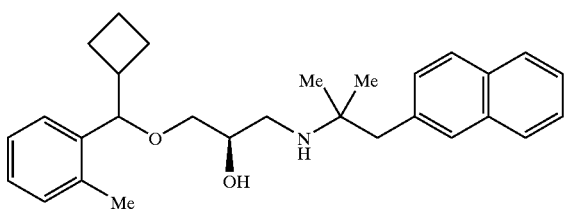 | $^1$H-NMR(300 MHz, δ ppm. DMSO-d$_6$) 7.90–7.64(4H, m), 7.50–7.30(3H, m), 7.25–7.05(4H, m), 4.61(1H, brs), 4.50–4.40(1H, m), 3.75–3.60 (1H, m), 3.17(2H, d, J=5.7 Hz), 2.85–2.45(4H, m), 2.31(3H, s), 1.95–1.50(6H, m), 1.45–0.90(7H, m). MS(APCI, m/z) 432(M + H)$^+$. |
| Ex. 54 | 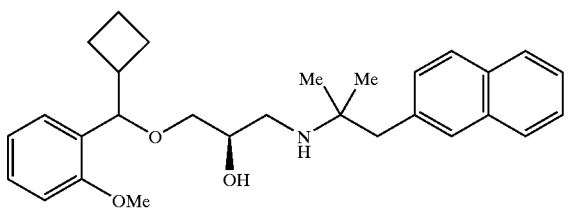 | $^1$H-NMR(300 MHz, δ ppm, DMSO-d$_6$) 7.90–7.70 (3H, m), 7.68(1H, s), 7.50–7.10(5H, m), 7.00–6.80 (2H, m), 4.70–4.50(2H, m), 3.78(3H, s). 3.70–3.50 (1H, m), 2.85–2.50(4H, m), 1.95–1.50(6H, m), 1.45–0.90(7H, m). MS(APCI, m/z) 448(M + H)$^+$. |
| Ex. 55 | 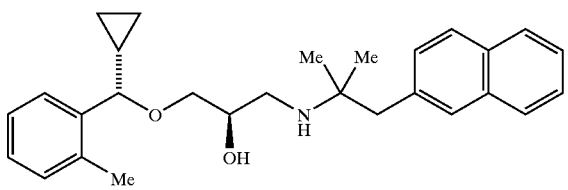 | $^1$H-NMR(300 MHz, δ ppm, DMSO-d$_6$) 7.90–7.70 (3H, m), 7.67(1H, s), 7.50–7.25(4H, m), 7.20–7.10 (3H, m), 4.65(1H, brs), 4.06(1H, d, J=7.4 Hz), 3.70–3.50(1H, m), 3.30–3.10(2H, m), 2.80–2.50 (4H, m), 2.31(3H, s). 1.50–0.80(8H, m), 0.60–0.10 (4H, m). MS(APCI, m/z) 418(M + H)$^+$. |

TABLE 7-continued

| Ex. 56 | 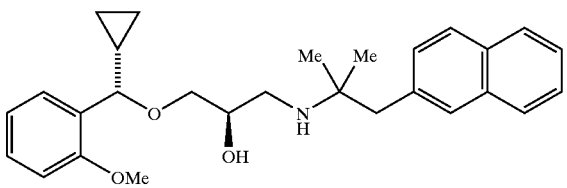 | ¹H-NMR(300 MHZ, δ ppm, CDCl₃) 7.85–7.70 (3H, m), 7.61(1H, s), 7.50–7.40(3H, m), 7.35–7.20 (2H, m), 7.00–6.80(2H, m), 4.27(1H, d, J=7.5 Hz), 3.85–3.75(4H, m), 3.50–3.30(2H, m), 2.85–2.65 (4H, m), 1.25–1.00(7H, m), 0.60–0.50(1H, m), 0.45–0.30(3H, m). MS(APCI, m/z) 434(M + H)⁺. |
|---|---|---|

Example 57

(2R)-1-[1,1-Dimethyl-2-(naphthalen-2-yl)ethylamino]-3-[(cyclopropyl)(2-hydroxymethylphenyl)methoxy]propan-2-ol Step 1

2-Bromo-1-(tert-butyldimethylsilyloxymethyl)benzene

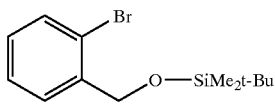

2-Bromobenzyl alcohol (25.0 g) was dissolved in N,N-dimethylformamide (150 ml) and imidazole (20.0 g) and tert-butyldimethylchlorosilane (22.2 g) were added. The reaction mixture was stirred at room temperature for 2 hr. The reaction mixture was poured into 5% aqueous sodium hydrogencarbonate solution and extracted with ethyl acetate. The organic layer was washed successively with 5% aqueous sodium hydrogencarbonate solution, water and saturated brine, dried over anhydrous sodium sulfate, and concentrated under reduced pressure to give the title compound (40.9 g).

Step 2

(Cyclopropyl)[2-(tert-butyldimethylsilyloxymethyl)-phenyl]methanol

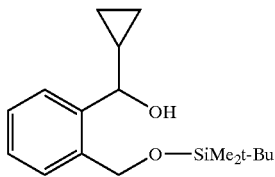

Magnesium (2.20 g) was suspended in tetrahydrofuran (4 ml) and iodine (2 mg) was added. Thereto was added dropwise a solution of 2-bromo-1-(tert-butyldimethylsilyloxymethyl)benzene (24.0 g) obtained in Step 1 in tetrahydrofuran (10 ml) over 30 min and the reaction mixture was heated under reflux for 1 hr. Thereto was added tetrahydrofuran to give 1M 2-(tert-butyldimethylsilyloxymethyl)phenylmagnesium bromide-tetrahydrofuran solution. Then cyclopropanecarboxaldehyde (2.80 g) was dissolved in tetrahydrofuran (120 ml), and 1M 2-(tert-butyldimethylsilyloxymethyl)phenylmagnesium bromide-tetrahydrofuran solution (80 ml) was added dropwise under ice-cooling over 50 min. The reaction mixture was stirred at room temperature for 12 hr. To the reaction mixture was added saturated aqueous ammonium chloride solution (8 ml) under ice-cooling and the reaction mixture was stirred at room temperature for 30 min. The reaction mixture was dried over anhydrous magnesium sulfate and concentrated under reduced pressure. The obtained residue was purified by silica gel column chromatography (n-hexane:ethyl acetate=95:5) to give the title compound (8.20 g).

¹H-NMR(300 MHz, δppm, DMSO-d₆) 7.53–7.34(2H,m), 7.25–7.20(2H,m), 4.91(1H,d,J=4.6 Hz), 4.81(2H,s), 4.31 (1H,dd,J=4.7, 6.5 Hz), 1.20–1.10(1H,m), 0.91(9H,s), 0.47–0.23(4H,m), 0.10(3H,s), 0.08(3H,s). MS(APCI,m/z) 275(M+H—H₂O)⁺.

Step 3

(R)-2-[(Cyclopropyl)[2-(tert-butyldimethylsilyloxymethyl)-phenyl]methoxymethyl]oxirane

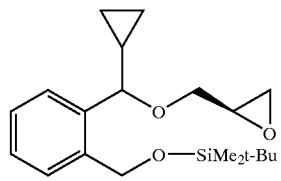

In the same manner as in Step 2 of Example 1, the title compound (1.04 g) was obtained from (cyclopropyl)[2-(tert-butyldimethylsilyloxymethyl)phenyl]methanol (2.11 g) obtained in Step 2.

Step 4

(2R)-1-[1,1-Dimethyl-2-(naphthalen-2-yl)ethylamino]-3-[(cyclopropyl)[2-(tert-butyldimethylsilyloxymethyl)-phenyl]methoxy]propan-2-ol

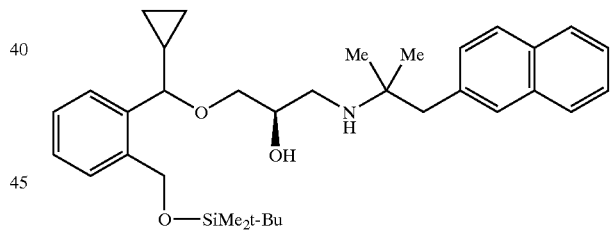

In the same manner as in Step 13 of Example 1, the title compound (345 mg) was obtained from (R)-2-[(cyclopropyl)(2-tert-butyldimethylsilyloxymethylphenyl)methoxymethyl]oxirane (546 mg) obtained in Step 3.

Step 5

(2R)-1-[1,1-Dimethyl-2-(naphthalen-2-yl)ethylamino]-3-[(cyclopropyl)[2-(hydroxymethyl)phenyl]methoxy]propan-2-ol

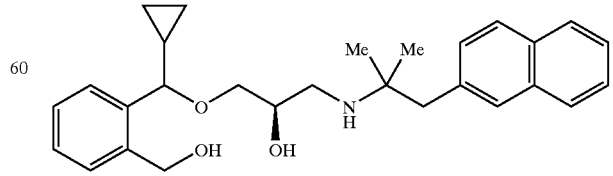

(2R)-1-[1,1-Dimethyl-2-(naphthalen-2-yl)ethylamino]-3-[(cyclopropyl)[2-(tert-butyldimethylsilyloxymethyl)- phenyl]methoxypropan-2-ol (365 mg) obtained in Step 4 was dissolved in tetrahydrofuran (4 ml) and tetrabutylammonium fluoride-1M tetrahydrofuran solution (0.73 ml) was added under ice-cooling. The mixture was stirred at room temperature for 4 hr. To the reaction mixture was added saturated aqueous ammonium chloride solution (1 ml) and poured into water. The mixture was extracted with ethyl acetate and the organic layer was washed successively with water and saturated brine, dried over anhydrous sodium sulfate, and concentrated under reduced pressure. The obtained residue was purified by silica gel column chromatography (ethyl acetate:methanol=98:2) to give the title compound (221 mg).

$^1$H-NMR(300 MHz, δppm, DMSO-$d_6$) 7.90–7.70(3H,m), 7.67(1H,s), 7.50–7.20(7H,m), 5.13(1H,brs), 4.90–4.40(3H,m), 4.20–4.05(1H,m), 3.70–3.50(1H,m), 3.30–3.10(2H,m), 2.80–2.50(4H,m), 1.40–0.85(7H,m), 0.60–0.10(4H,m). MS(APCI,m/z) 434(M+H)$^+$.

Example 58

(2R)-1-[1,1-Dimethyl-2-(naphthalen-2-yl)ethylamino]-3-[(1R)-(cyclopropyl)[2-(hydroxymethyl)phenyl]methoxy]propan-2-ol hemifumarate Step 1

2-tert-Butyldimethylsilyloxymethyl-N-methoxy-N-methylbenzamide

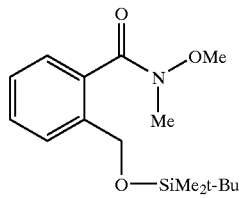

To a solution of phthalide (26.8 g) in methylene chloride (600 ml) were successively added N,O-dimethylhydroxylamine hydrochloride (58.5 g) and aluminum chloride (40.0 g) under ice-cooling, and triethylamine (139 ml) was added dropwise over 40 min. The mixture was stirred at room temperature for 12 hr. The reaction mixture was poured into diluted hydrochloric acid, and the organic layer was washed successively with water and saturated brine, dried over anhydrous magnesium sulfate, and concentrated under reduced pressure to give 2-hydroxymethyl-N-methoxy-N-methylbenzamide. The obtained 2-hydroxymethyl-N-methoxy-N-methylbenzamide was dissolved in N,N-dimethylformamide (300 ml), and imidazole (9.53 g) and tert-butyldimethylchlorosilane (21.1 g) were added. The mixture was stirred at room temperature for 3.5 hr and the reaction mixture was poured into water and extracted with ethyl acetate. The organic layer was washed successively with water and saturated brine, dried over anhydrous sodium sulfate, and concentration under reduced pressure. The obtained residue was purified by silica gel column chromatography (ethyl acetate:hexane=1:3) to give the title compound (42.0 g).

Step 2

(Cyclopropyl)[2-(tert-butyldimethylsilyloxymethyl)phenyl]methanone

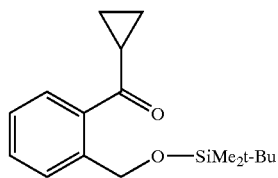

In the same manner as in Step 2 of Example 23, the title compound (18.4 g) was obtained from 2-tert-butyldimethylsilyloxymethyl-N-methoxy-N-methylbenzamide (21.7 g) obtained in Step 1.

$^1$H-NMR(300 MHz, δppm, CDCl$_3$) 7.88(1H,dd,J=1.1, 7.7 Hz), 7.78(1H,d,J=7.3 Hz), 7.53(1H,dt,J=1.2, 7.6 Hz), 7.35 (1H,t,J=7.2 Hz), 4.97(2H,s), 2.57–2.48(1H,m), 1.24–1.20 (2H,m), 1.06–1.01(2H,m), 0.95(9H,s), 0.11(6H,s).

Step 3

(R)-(Cyclopropyl)[2-(tert-butyldimethylsilyloxymethyl)-phenyl]methanol

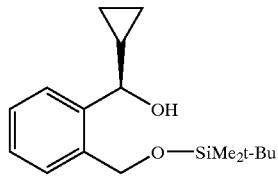

To a suspension of dichloro[(S)-2,2'-bis(diphenylphosphino)-1,1'-binaphthyl][(S)-1,1'-bis(p-methoxyphenyl)-2-isopropylethane-1,2-diamine]ruthenium (II) (111 mg) and potassium-tert-butoxide (44.9 mg) in isopropanol (100 ml) was added (cyclopropyl)[2-(tert-butyldimethylsilyloxymethyl)phenyl]methanone (5.81 g) obtained in Step 2, and the mixture was subjected to medium pressure hydrogenation (5.0 kgf/cm$^2$) at room temperature for 36 hr. The reaction mixture was concentrated under reduced pressure, and the residue was purified by silica gel column chromatography (ethyl acetate:hexane=1:5) to give the title compound (5.82 g).

$^1$H-NMR(300 MHz, δppm, DMSO-$d_6$) 7.49–7.46(1H,m), 7.39–7.37(1H,m), 7.25–7.22(2H,m), 4.99(1H,br s), 4.81 (2H,s), 4.32(1H,d,J=6.3 Hz), 1.32–1.09(1H,m), 0.91(9H,s), 0.49–0.22(4H,m), 0.10(3H,s), 0.08(3H,s). MS(ESI,m/z) 275 (M+H—H$_2$O)$^+$.

Step 4

(R)-2-[(1R)-(Cyclopropyl)[2-(tert-butyldimethylsilyloxymethyl)-phenyl]methoxymethyl]oxirane

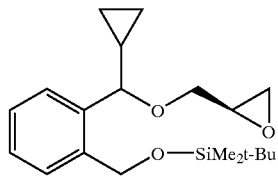

In the same manner as in Step 2 of Example 1, the title is compound (2.52 g) was obtained from (R)-(cyclopropyl)[2-(tert-butyldimethylsilyloxymethyl)phenyl]methanol (2.92 g) obtained in Step 3.

Step 5

(2R)-1-[1,1-Dimethyl-2-(naphthalen-2-yl)ethylamino]-3-[(1R)-(cyclopropyl)[2-(tert-butyldimethylsilyloxymethyl)-phenyl]methoxypropan-2-ol

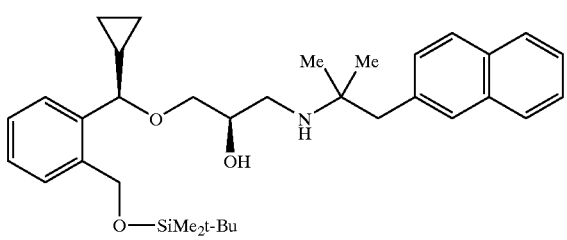

In the same manner as in Step 13 of Example 1, the title compound (1.79 g) was obtained from (R)-2-[(1R)-(cyclopropyl)[2-(tert-butyldimethylsilyloxymethyl)-phenyl]methoxymethyl]oxirane (1.22 g) obtained in Step 4.

Step 6
(2R)-1-[1,1-Dimethyl-2-(naphthalen-2-yl)ethylamino]-3-[(1R)-(cyclopropyl)[2-(hydroxymethyl)phenyl]methoxy]propan-2-ol

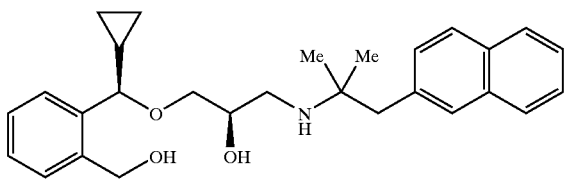

In the same manner as in Step 5 of Example 57, the title compound (710 mg) was obtained from (2R)-1-[1,1-dimethyl-2-(naphthalen-2-yl)ethylamino]-3-[(1R)-(cyclopropyl)[2-(tert-butyldimethylsilyloxymethyl)phenyl]methoxypropan-2-ol (1.70 g) obtained in Step 5.

Step 7
(2R)-1-[1,1-Dimethyl-2-(naphthalen-2-yl)ethylamino]-3-[(1R)-(cyclopropyl)[2-(hydroxymethyl)phenyl]methoxy]propan-2-ol hemifumarate

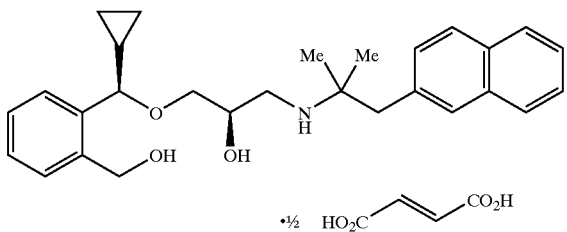

(2R)-1-[1,1-Dimethyl-2-(naphthalen-2-yl)ethylamino]-3-[(1R)-(cyclopropyl)[2-(hydroxymethyl)phenyl]methoxy]propan-2-ol (700 mg) obtained in Step 6 was dissolved in methanol (15 ml), and fumaric acid (94 mg) was added. The mixture was stirred for 30 min. The reaction mixture was concentrated under reduced pressure, and ether was added to the residue. The precipitated solid was collected by filtration to give the title compound (720 mg).

$^1$H-NMR(300 MHz, δppm, DMSO-d$_6$) 7.95–7.85(3H,m), 7.73(1H,s), 7.55–7.20(7H,m), 6.51(1H,s), 4.63(1H,d,J=13.2 Hz), 4.56(1H,d,J=13.2 Hz), 4.13(1H,d,J=7.5 Hz), 3.90–3.80 (1H,brs), 3.40–3.15(2H,m), 3.05–2.95(3H,m), 2.80–2.65 (1H,m), 1.20–1.00(7H,m), 0.60–0.20(4H,m). MS(ESI,m/z) 434(M+H-1/2C$_4$H$_4$O$_4$)$^+$.

Example 59

(2R)-1-[1,1-Dimethyl-2-(naphthalen-2-yl)ethylamino]-3-[(1S)-(cyclopropyl)[2-(hydroxymethyl)phenyl]methoxy]propan-2-ol hemifumarate Step 1
(S)-(Cyclopropyl)[2-(tert-butyldimethylsilyloxymethyl)-phenyl]methanol

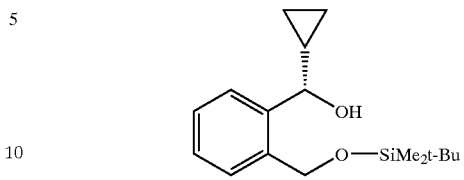

To a suspension of dichloro[(R)-2,2'-bis(diphenylphosphino)-1,1'-binaphthyl][(R)-1,1'-bis(p-methoxyphenyl)-2-isopropylethane-1,2-diamine]ruthenium(II) (111 mg) and potassium-tert-butoxide (44.9 mg) in isopropanol (100 ml) was added (cyclopropyl)[2-(tert-butyldimethylsilyloxymethyl)phenyl]methanone (5.81 g) obtained in Step 2 of Example 58, and the mixture was subjected to medium pressure hydrogenation (5.0 kgf/cm$^2$) at room temperature for 36 hr. The reaction mixture was concentrated under reduced pressure, and the residue was purified by silica gel column chromatography (ethyl acetate:hexane=1:5) to give the title compound (5.50 g).

$^1$H-NMR(300 MHz, δppm, DMSO-d$_6$) 7.49–7.46(1H,m), 7.40–7.37(1H,m), 7.22–7.20(2H,m), 4.99(1H,d,J=4.2 Hz), 4.81(2H,s), 4.31(1H,dd,J=4.5, 6.6 Hz), 1.20–1.09(1H,m), 0.91(9H,s), 0.47–0.21(4H,m), 0.10(3H,s), 0.08(3H,s). MS(ESI,m/z) 275(M+H—H$_2$O)$^+$.

Step 2
(R)-2-[(1S)-(Cyclopropyl)[2-(tert-butyldimethylsilyloxymethyl)-phenyl]methoxymethyl]oxirane

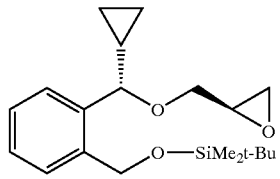

In the same manner as in Step 2 of Example 1, the title compound (2.62 g) was obtained from (S)-(cyclopropyl)[2-(tert-butyldimethylsilyloxymethyl)phenyl]methanol (2.92 g) obtained in Step 1.

Step 3
(2R)-1-[1,1-Dimethyl-2-(naphthalen-2-yl)ethylamino]-3-[(1S)-(cyclopropyl)[2-(tert-butyldimethylsilyloxymethyl)-phenyl]methoxy]propan-2-ol

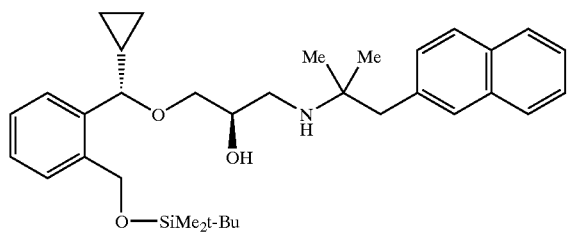

In the same manner as in Step 13 of Example 1, the title compound (1.80 g) was obtained from (R)-2-[(1S)-(cyclopropyl)[2-(tert-butyldimethylsilyloxymethyl)-phenyl]methoxymethyl]oxirane (1.22 g) obtained in Step 2.

Step 4
(2R)-1-[1,1-Dimethyl-2-(naphthalen-2-yl)ethylamino]-3-[(1S)-(cyclopropyl)[2-(hydroxymethyl)phenyl]methoxy]

propan-2-ol

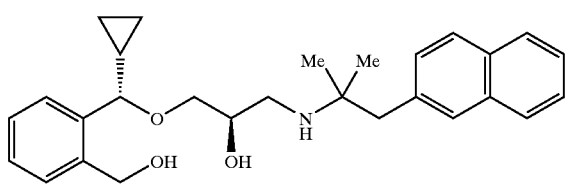

In the same manner as in Step 5 of Example 57, the title compound (1.26 g) was obtained from (2R)-1-[1,1-dimethyl-2-(naphthalen-2-yl)ethylamino]-3-[(1S)-(cyclopropyl)[2-(tert-butyldimethylsilyloxymethyl)phenyl]methoxy]propan-2-ol (1.70 g) obtained in Step 3.

Step 5

(2R)-1-[1,1-Dimethyl-2-(naphthalen-2-yl)ethylamino]-3-[(1S)-(cyclopropyl)[2-(hydroxymethyl)phenyl]methoxy]propan-2-ol hemifumarate

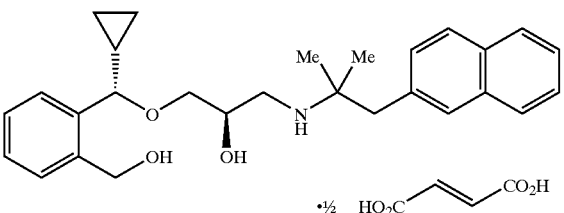

In the same manner as in Step 7 of Example 58, the title compound (1.33 g) was obtained from (2R)-1-[1,1-dimethyl-2-(naphthalen-2-yl)ethylamino]-3-[(1S)-(cyclopropyl)[2-(hydroxymethyl)phenyl]methoxy]propan-2-ol (1.25 g) obtained in Step 4.

$^1$H-NMR(300 MHz, δppm, DMSO-$d_6$) 7.90–7.80(3H,m), 7.71(1H,s), 7.50–7.20(7H,m), 6.48(1H,s), 4.63(1H,d,J=13.2 Hz), 4.56(1H,d,J=13.2 Hz), 4.12(1H,d,J=7.8 Hz), 3.80–3.70 (1H,brs), 3.35–3.15(2H,m), 2.95–2.85(3H,m), 2.80–2.65 (1H,m), 1.20–1.00(7H,m), 0.60–0.20(4H,m). MS(ESI,m/z) 434(M+H-1/2C$_4$H$_4$O$_4$)$^+$.

Example 60–Example 160

In the same manner as in Examples 1–59, the compounds of Example 60–Example 160 were obtained. They are shown in Table 8–Table 23.

TABLE 8

| Ex. 60 | 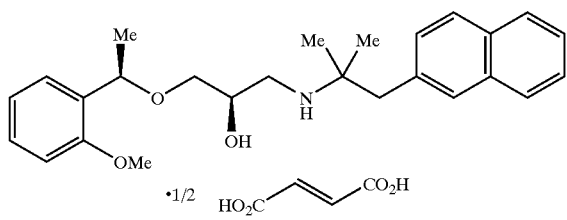 | $^1$H-NMR(300 MHz, δ ppm, DMSO-$d_6$)<br>7.95–7.75(3H, m), 7.71(1H, s), 7.55–7.45(2H, m),<br>7.40–7.20(3H, m), 7.05–6.90(2H, m), 6.48(1H, s), 4.80<br>(1H, q, J=6.4 Hz), 3.90–3.70(4H, m), 3.40–<br>3.20(2H, m), 3.00–2.80(3H, m), 2.75–2.60(1H, m),<br>1.28(3H, d, J=6.4 Hz), 1.15–1.85(6H, m).<br>MS(APCI, m/z) 408(M + H-1/2C$_4$H$_4$O$_4$)$^+$. |
|---|---|---|
| Ex. 61 | 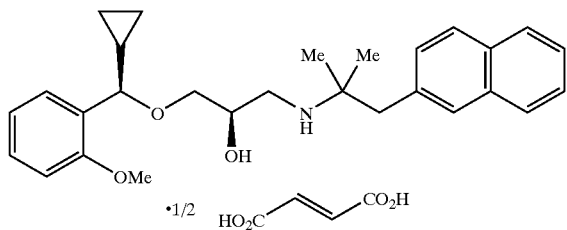 | $^1$H-NMR(300 MHz, δ ppm, CDCl$_3$) 7.95–7.75<br>(3H, m), 7.71(1H, s), 7.60–7.15(5H, m), 7.05–<br>6.85(2H, m), 6.48(1H, s), 4.29(1H, d, J=7.2 Hz), 3.85–<br>3.70(4H, m), 3.40–3.10(2H, m), 3.00–2.80(4H,<br>m), 2.75–2.60(1H, m), 1.20–1.00(7H, m),<br>0.60–0.20(4H, m).<br>MS(APCI, m/z) 434(M + H-1/2C$_4$H$_4$O$_4$)$^+$. |
| Ex. 62 | 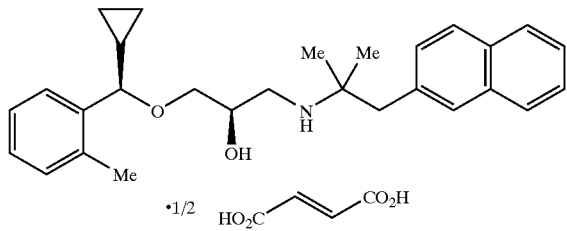 | $^1$H-NMR(300 MHz, δ ppm, DMSO-$d_6$) 7.90–7.80<br>(3H, m), 7.71(1H, s), 7.60–7.25(4H, m), 7.20–7.10<br>(3H, m), 6.49(1H, s), 4.09(1H, d, J=7.5 Hz),<br>3.80(1H, brs), 3.40–3.10(2H, m), 3.00–2.80(3H,<br>m), 2.75–2.60(1H, m), 2.32(3H, s), 1.25–<br>1.00(7H, m), 0.60–0.10(4H, m).<br>MS(APCI, m/z) 418(M + H-1/2C$_4$H$_4$O$_4$)$^+$. |
| Ex. 63 | 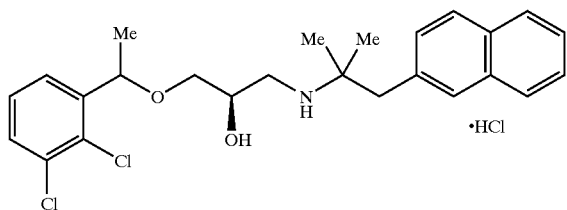 | $^1$H-NMR(300 MHz, δ ppm, DMSO-$d_6$) 9.00(1H, bs),<br>8.57(1H, bs), 7.95–7.85(3H, m), 7.62(1H, s), 7.65–7.35<br>(6H, m), 5.75–5.65(1H, m), 4.95–4.85(1H, m), 4.10–<br>4.00(1H, m), 3.50–3.30(2H, m), 3.30–3.10(3H,<br>m), 3.05–2.90(1H, m), 1.39(3H, d, J=6.4 Hz),<br>1.27(6H, s).<br>MS(APCI, m/z) 446(M + H—HCl)$^+$. |

TABLE 8-continued

| Ex. 64 | 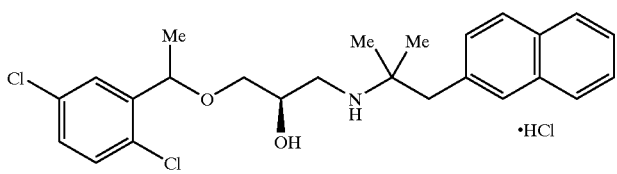 | $^1$H-NMR(300 MHz, δ ppm, DMSO-d$_6$) 8.98(1H, bs), 8.57(1H, bs), 7.95–7.85(3H, m), 7.59(1H, s), 7.60–7.45 (4H, m), 7.45–7.35(2H, m), 5.80–5.65(1H, m), 4.85– 4.75(1H, m), 4.10–4.00(1H, m), 3.50–3.30(2H, m), 3.25–3.10(3H, m), 3.05–2.90(1H, m), 1.40–1.35(3H, m), 1.27(6H, s). MS(APCI, m/z) 446(M + H—HCl)$^+$. |
| --- | --- | --- |
| Ex. 65 | 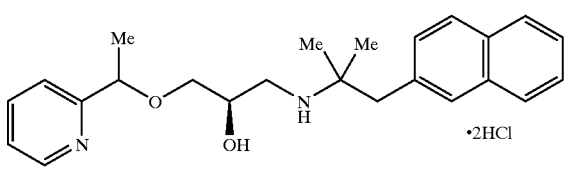 | $^1$H-NNR(300 MHz, δ ppm, DMSO-d$_6$) 9.33(1H, bs), 8.85–8.65(2H, m), 8.50–8.40(1H, m), 8.05–7.70 (6H, m), 7.60–7.35(3H, m), 5.05–4.90 (1H, m), 4.20–4.10(1H, m), 3.70–3.55(2H, m), 3.50–3.40(1H, m), 3.30–3.15(3H, m), 3.10–2.95(1H, m), 1.53(3H, d, J=6.6 Hz), 1.29(6H, s). MS(APCI, m/z) 379(M + H-2HCl)$^+$. |

TABLE 9

| Ex. 66 | 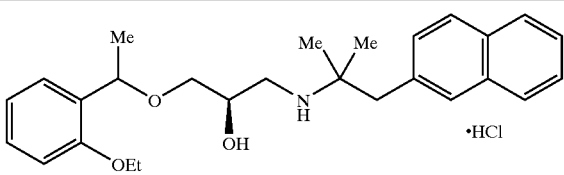 | $^1$H-NMR(300 MHz, δ ppm, DMSO-d$_6$) 8.94(1H, bs), 8.56(1H, bs), 7.95–7.85(3H, m), 7.77(1H, s), 7.55– 7.45(2H, m), 7.40–7.20(3H, m), 7.05–6.90(2H, m), 5.61(1H, d, J=4.8 Hz), 4.84(1H, dd, J=9.5, 6.3 Hz), 4.10–4.00(1H, m), 3.80(3H, s), 3.45– 3.10(5H, m), 3.00–2.85(1H, m), 1.32(3H, d, J= 6.3 Hz), 1.26(6H, s). MS(APCI, m/z) 408(M + H—HCl)$^+$. |
| --- | --- | --- |
| Ex. 67 | 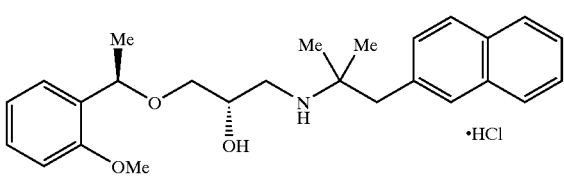 | $^1$H-NMR(300 MHz, δ ppm, DMSO-d$_6$) 8.87(1H, bs), 8.53(1H, bs), 7.95–7.85(3H, m), 7.77(1H, s), 7.55– 7.45(2H, m), 7.45–7.35(2H, m), 7.30–7.20(1H, m), 7.05–6.90(2H, m), 5.64(1H, d, J=4.8 Hz), 4.84(1H, dd, J=9.6, 6.3 Hz), 4.05–3.95(1H, m), 3.80(3H, s), 3.40–3.30(2H, m), 3.25–3.10(3H, m), 3.10–2.95(1H, m), 1.32(3H, d, J=6.6 Hz), 1.27(6H, s). MS(APCI, m/z) 408 + H-HCl)$^+$. |
| Ex. 68 | 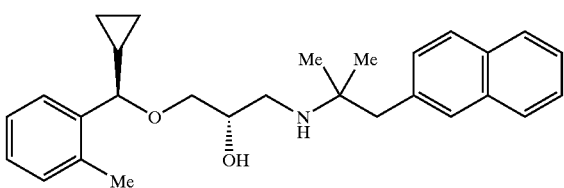 | $^1$H-NMR(300 MHz, δ ppm, DMSO-d$_6$) 7.90–7.70 (3H, m), 7.67(1H, s), 7.50–7.25(4H, m), 7.20– 7.10(3H, m), 4.65(1H, brs), 4.06(1H, d, J=7.4 Hz), 3.70–3.50(1H, m), 3.30–3.10(2H, m), 2.80–2.50(4H, m), 2.31(3H, s), 1.50–0.80(8H, m), 0.60–0.10 (4H, m). MS(APCI, m/z) 418 (M + H)$^+$. |
| Ex. 69 | 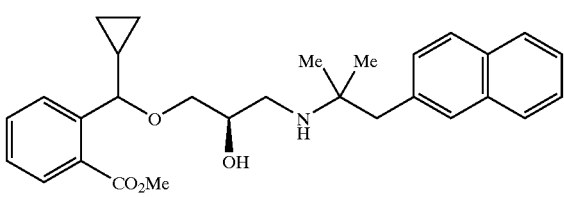 | $^1$H-NNR(300 MHz, δ ppm, CDCl$_3$) 7.90–7.20 (11H, m), 4.82(1H, d, J=7.3 Hz), 3.88(3H, s), 3.95–3.70(1H, m), 3.55–3.20.(2H, m), 2.90–2.60 (4H, m), 1.30–1.00(7H, m), 0.70–0.30(4H, m), MS(ESI, m/z) 462(M + H)$^+$. |
| Ex. 70 | 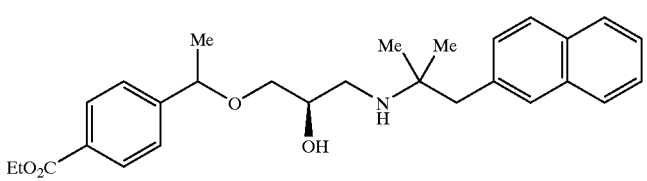 | $^1$H-NMR(300 MHz, δ ppm, CDCl$_3$) 8.10–8.00 (2H, m), 7.85–7.70(3H, m), 7.60(1H, s), 7.50–7.20(5H, m), 4.55–4.45(1H, m), 4.37(2H, dd, J=10.7, 5.9 Hz), 3.85– 3.70(1H, m), 3.40–3.25(2H, m), 2.90–2.55 (4H, m), 1.45–1.35(6H, m), 1.10–1.00(6H, m). MS(APCI, m/z) 450(M + H)$^+$. |
| Ex. 71 | 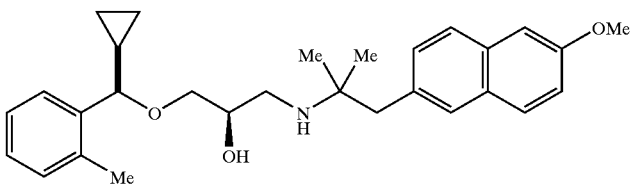 | $^1$H-NMR(300 MHz, δ ppm, DMSO-d$_6$) 7.40– 7.00(6H, m), 6.83(2H, d, J=8.5 Hz), 4.08(1H, d,J=7.5 Hz), 3.80–3.60(4H, m), 3.40–3.10 (2H, m), 2.90–2.50(4H, m) , 2.32(3H, s), 1.30–0.80(7H, m), 0.60–0.15(4H, m). MS(ESI, m/z) 398(M + H)$^+$. |

TABLE 9-continued

Ex. 72 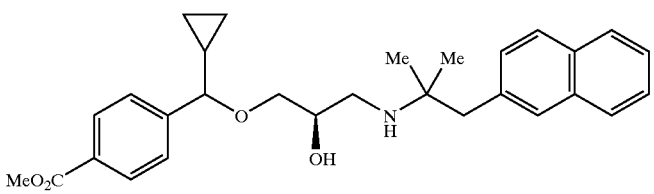
¹H-NMR(300 MHz, δ ppm, CDCl₃) 8.05–8.00 (2Hm), 7.85–7.70(3H, m), 7.61(1H, s), 7.50–7.25 (5H, m), 3.91(3H, s), 3.90–3.70(2H, m), 3.45–3.30(2H, m), 2.90–2.60(4H, m), 1.15–1.00(7H, m), 0.65–0.55(1H, m), 0.50–0.35(2H, m), 0.30–0.20(1H, m).
MS(ESI, m/z) 462 (M + H)⁺.

TABLE 10

Ex. 73 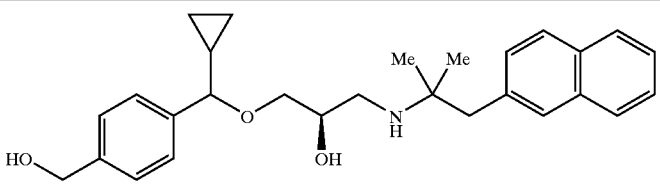
¹H-NMR(400 MHz, δ ppm, CDCl₃) 7.85–7.70 (3H, m), 7.61(1H, s), 7.50–7.20(7H, m), 4.67(2H, d, J=4.4 Hz), 3.80–3.65(2H, m), 3.45–3.30(2H, m), 2.90–2.60(4H, m), 1.20–1.00(7H, m), 0.65–0.60(1H, m), 0.50–0.40(2H, m), 0.30–0.20(1H, m).
MS(ESI, m/z) 434(M + H).⁺.

Ex. 74 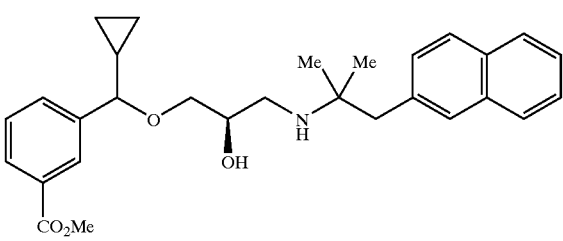
¹H-NMR(300 MHz, δ ppm, CDCl₃) 8.00–7.90 (2H, m), 7.85–7.70(3H, m), 7.61(1H, s), 7.55–7.25(5H, m), 3.91(3H, s), 3.85–3.70(3H, m), 3.50–3.30(2H, m), 2.90–2.60(4H, m), 1.20–1.00 (7H, m), 0.65–0.55(1H, m), 0.50–0.40(2H, m), 0.30–0.20(1H, m).
MS(ESI, m/Z) 462(M + H)⁺.

Ex. 75 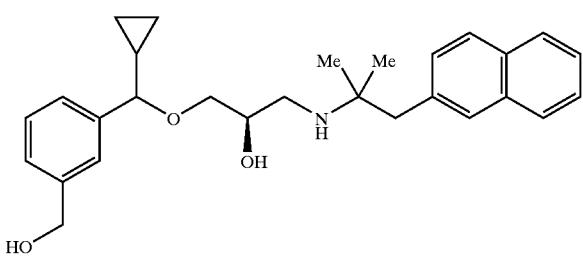
¹H-NMR(300 MHz, δ ppm, CDCl₃) 7.85–7.70 (3H, m), 7.61(1H, s), 7.50–7.15(7H, m), 4.69(2H, d, J=3.5 Hz), 3.80–3.60(2H, m), 3.45–3.35(2H, m), 2.90–2.70(4H, m), 1.20–1.00 (7H, m), 0.70–0.55(1H, m), 0.50–0.40(2H, m), 0.30–0.20(1H, m).
MS(ESI, m/z) 434(M + H)⁺.

Ex. 76 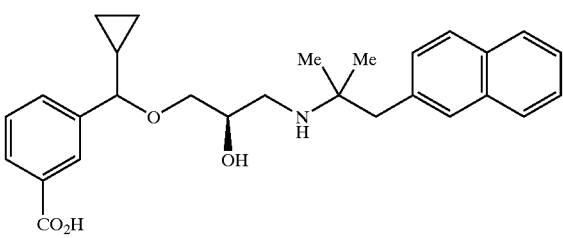
¹H-NNR(300 MHz, δ ppm, DMSO-d₆) 8.00–7.80(5H, m), 7.79(1H, s), 7.60–7.30(5H, m), 3.90–2.60(8H, m), 1.20–1.00(7H, m), 0.60–0.20(4H, m).
MS(ESI, m/z) 448(M + H)⁺.

Ex. 77 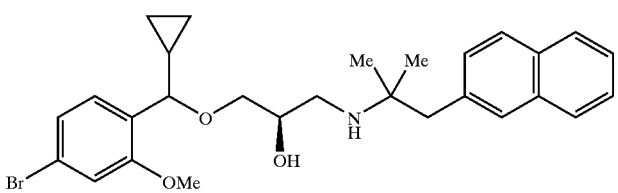
¹H-NNR(300 MHz, δ ppm, CDCl₃) 7.80–7.70 (3H, m), 7.61(1H, s), 7.50–7.20(5H, m), 6.80–6.70(1H, m), 4.22(1H, d, J= 7.8 Hz), 3.85–3.70(4H, m), 3.50–3.30(2H, m), 3.00–2.60(4H, m), 1.20–1.00(7H, m), 0.60–0.50 (1H, m), 0.60–0.50(1H, m), 0.50–0.30(3H, m).
MS(ESI, m/z) 513 (M + H)⁺.

Ex. 78 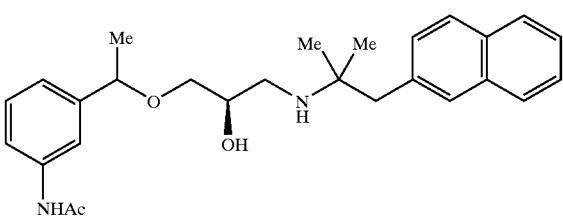
¹H-NMR(300 MHz, δ ppm, CDCl₃) 7.83–7.74 (3H, m), 7.61(1H, brs), 7.48–7.41(4H, m), 7.32–7.19(3H, m), 7.02–6.99(1H, m), 4.41–4.39(1H, m), 3.80–3.70(1H, m), 3.38–3.34(2H, m), 2.87–2.81(3H, m), 2.70–2.60 (1H, m), 2.15(3H, s), 1.43–1.37(3H, m), 1.12-1.09(6H, m).
MS(ESI, m/z) 435(M + H)⁺.

TABLE 10-continued

Ex. 79 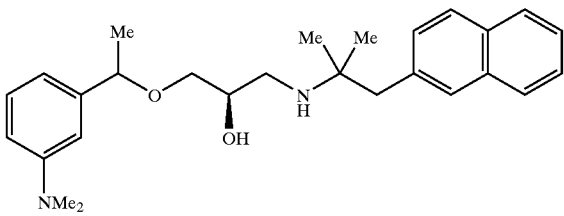
¹H-NMR(300 MHz, δ ppm, CDCl₃) 7.80–7.74 (3H, m), 7.65–7.60(1H, m), 7.46–7.43(2H, m), 7.30–7.19(2H, m), 6.66–6.63(3H, m), 4.37–4.35(1H, m), 3.85–3.75(1H, m), 3.40–3.34(2H, m), 2.95(6H, s), 2.98–2.60(4H, m), 1.44–1.40(3H, m), 1.12–1.08(6H, m).
MS(ESI, m/z) 421(M + H)⁺.

TABLE 11

Ex. 80 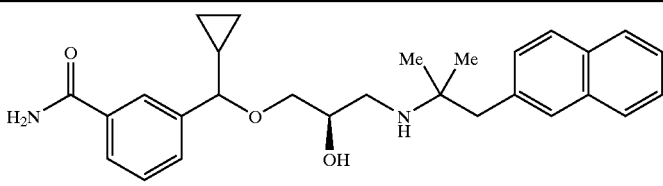
¹H-NMR(300 MHz, δ ppm CDCl₃) 7.90–7.70(5H, m), 7.60(1H, s), 7.50–7.20(5H, m), 6.30(1H, bs), 5.70(1H, bs), 3.85–3.70(2H, m), 3.50–3.30(2H, m), 2.90–2.60(4H, m), 1.20–1.00(7H, m), 0.70–0.60(1H, m), 0.55–0.40(2H, m), 0.35–0.25(1H, m).
MS(ESI, m/z) 447(M + H)⁺.

Ex. 81 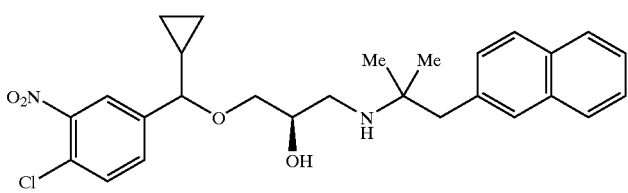
¹H-NNR(300 MHz, δ ppm, DMSO-d₆) 8.05–7.30(10H, m), 4.71(1H, brs), 3.90–3.80(1H, m), 3.75–3.50(1H, m), 3.45–3.10(2H, m), 2.90–2.50(4Hm), 1.10–0.80(7H, m), 0.70–0.20(4H, m).
MS(ESI, m/z) 4830(M + H)⁺.

Ex. 82 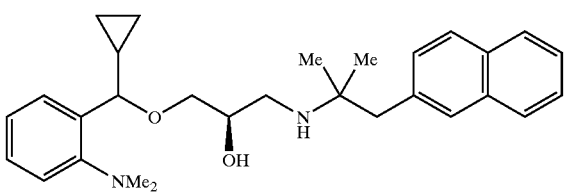
¹H-NMR(300 MHz, δ ppm CDCl₃) 7.79–7.74(3H, m), 7.62(1H, brs), 7.46–7.43(3H, m), 7.33–7.11(4H, m), 4.49–4.43(1H, m), 3.80–3.70(1H, m), 3.48–3.33(2H, m), 2.86–2.69(4H, m), 2.63(3H, s), 2.62(3H, s), 1.20–1.09(7H, m), 0.60–0.20(4H, m).
MS(ESI, m/z) 447(M + H)⁺.

Ex. 83 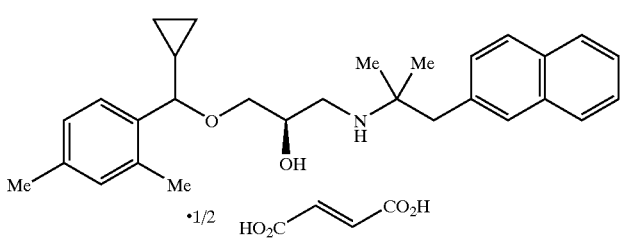
¹H-NMR(300 MHz, δ ppm CDCl₃) 7.80–7.76(3H, m), 7.64(1H, s), 7.46–7.44(2H, m), 7.30–7.17(4H, m), 6.99–6.92(2H, m), 6.85(1H, s), 4.10–3.95 (2H, m), 3.50–3.30(2H, m), 3.18–2.80(4H, m), 2.27(3H, s), 2.26(3H, s), 1.29–1.22(6H, m), 1.20–1.00(1H, m), 0.60–0.10(4H, m).
MS (ESI, m/z) 432 (M + H-1/2C₄H₄O₄)⁺.

Ex. 84 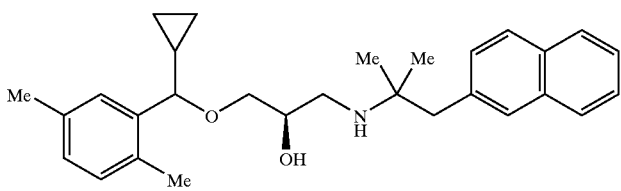
¹H-NMR(300 MHz, δ ppm CDCl₃) 7.82–7.73(3H, m), 7.60(1H, s), 7.45–7.43(2H, m), 7.32–7.28(1H, m), 7.16 (1H, s), 7.03–6.96(2H, m), 4.04(1H, d, J=7.5 Hz), 3.82–3.74(1H, m), 3.40–3.32(2H, m), 2.86–2.69(4H, m), 2.31–2.28(6H, m), 1.22–1.09(7H, m), 0.59–0.23(4H, m).
MS(ESI, m/z) 432(M + H)⁺.

Ex. 85 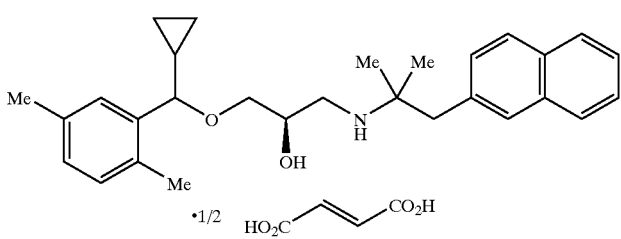
¹H-NMR(300 MHz, δ ppm CDCl₃) 7.80–7.74(3H, m), 7.63(1H, s), 7.45–7.43(2H, m), 7.32–7.28(1H, m), 7.12 (1H, s), 7.03–6.97(2H, m), 6.85(1H, s), 4.26–4.12(1H, m), 4.01(1H, d, J=7.8 Hz), 3.62–3.28(2H, m), 3.20–2.76(4H, m), 2.28–2.24(6H, m), 1.29–1.05(7H, m), 0.60–0.48 (1H, m),0.40–0.26(2H, m), 0.22–0.14(1H, m).
MS(ESI, m/z) 432(M + H-1/2C₄H₄O₄)⁺.

TABLE 11-continued

| Ex. 86 | 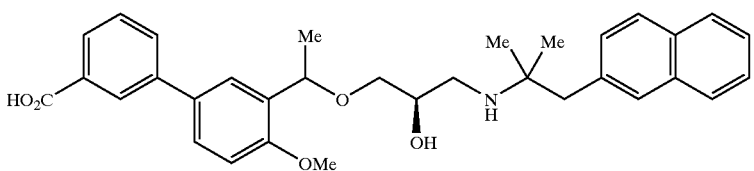 | ¹H-NMR(300 MHz, δ ppm DMSO-d₆) 8.19(1H, s), 7.90–7.30(12H, m), 7.20–7.10(1H, m), 4.40–4.30(1H, m), 3.90–3.80(4H, m), 3.45–3.25(2H, m), 3.00–2.85(3H, m), 2.80–2.65(1H, m), 1.25–1.00(7H, m), 0.60–0.30(4H, m). MS(ESI, m/z) 554(M + H)⁺. |

TABLE 12

| Ex. 87 | 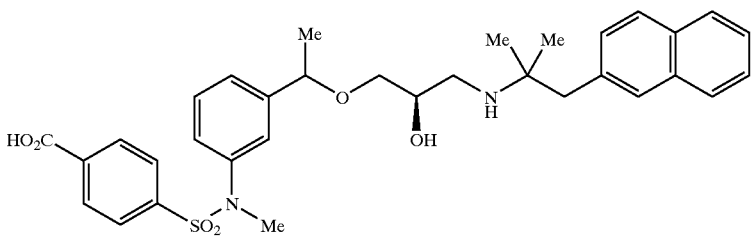 | ¹H-NNR(300 MHz, δ ppm, DMSO-d₆) 8.10–8.00(2H, m), 7.90–7.70(3H, m), 7.50–7.14(9H, m), 6.80–6.70(1H, m), 4.36–4.34(1H, m), 3.90–3.80(1H, m), 3.20–2.60(9H, m), 1.26–1.20(9H, m). MS(ESI, m/z) 591(M + H)⁺. |
| Ex. 88 | 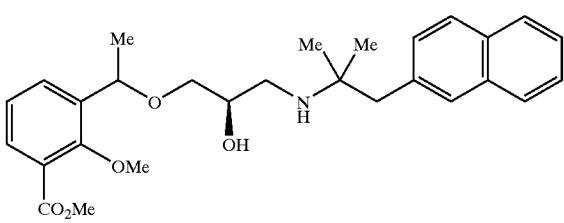 | ¹H-NMR(400 MHz, δ ppm, CDCl₃) 7.90–7.70(4H, m), 7.68–7.60(1H, m), 7.60–7.40(3H, m), 7.30–7.15(3H, m), 4.18–4.09(2H, m), 3.91–3.90(3H, m), 3.81–3.79(3H, m), 3.60–3.40(2H, m), 3.30–2.90(4H, m), 1.35–1.28(6H, m), 1.20–0.80(1H, m), 0.60–0.20 (4H, m). MS(ESI, m/z) 492 (M + H)⁺. |
| Ex. 89 | 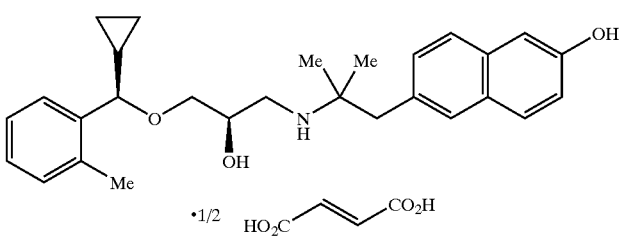 | ¹H-NNR(300 MHz, δ ppm, DMSO-d₆) 7.68(1H, d, J=8.4 Hz), 7.59–7.55 (2H, m), 7.33–7.32(1H, m), 7.25–7.18 (4H, m), 7.08–7.04(2H, m), 6.48(1H, s), 4.08(1H, d, J=7.8 Hz), 3.78(1H, brs), 3.36–3.17(4H, m), 2.90–2.85(2H, m), 2.31(3H, s), 1.10–1.07(7H, m), 0.52–0.50(1H, m), 0.37–0.33(2H, m) 0.14–0.10(1H, m). MS(ESI, m/z) 434(M + H-1/2C₄H₄O₄)⁺. |
| Ex. 90 | 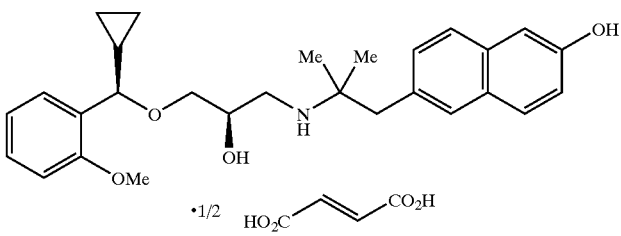 | ¹H-NNR(300 MHz, δ ppm, DMSO-d₆) 7.70(1H, d, J=8.7 Hz), 7.61–7.57(2H, m), 7.35–7.32(1H, m), 7.26–7.22(2H, m), 7.08–6.94(4H, m), 6.50(1H, s), 4.27(1H, d, J=7.1 Hz), 3.84–3.72(4H, m), 3.48–3.18(4H, m), 3.06–2.92(2H, m), 1.17–1.08(7H, m), 0.50–0.24(4H, m). MS(ESI, m/z) 450(M + H-1/2C₄H₄O₄)⁺. |
| Ex. 91 | 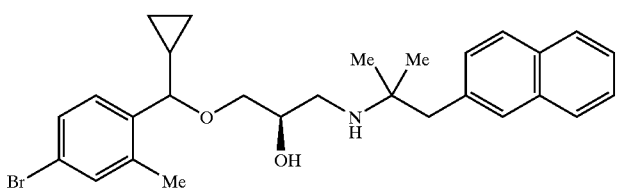 | ¹H-NNR(300 MHz, δ ppm, CdCl₃) 7.85–7.70(3H, m), 7.61(1H, s), 7.50–7.40 (2H, m), 7.35–7.15(4H, m), 4.10–4.00(1H, m), 3.85–3.70(1H, m), 3.40–3.25(2H, m), 2.90–2.60(4H, m), 2.29(3H, m), 1.20–1.00(7H, m), 0.65–0.55(1H, m), 0.50–0.15(3H, m). MS(ESI, m/z) 497(M + H)⁺. |

TABLE 12-continued

| Ex. 92 | 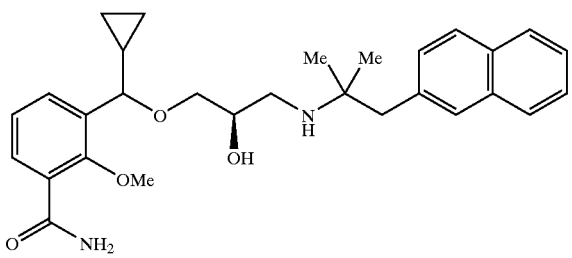 | $^1$H-NNR(300 MHz, δ ppm, DMSO-$d_6$)<br>8.00–7.94(1H, m), 7.80–7.70(3H, m),<br>7.61–7.55(2H, m), 7.46–7.43(3H, m),<br>7.28–7.16(2H, m), 5.80–5.70(1H, brs),<br>4.22–4.17(1H, m), 3.81–3.70(4H, m),<br>3.50–3.30(2H, m), 2.85–2.60(4H, m),<br>1.15–1.07(7H, m), 0.70–0.30(4H, m).<br>MS(ESI, m/z) 477 (M + H)$^+$. |
|---|---|---|
| Ex. 93 | 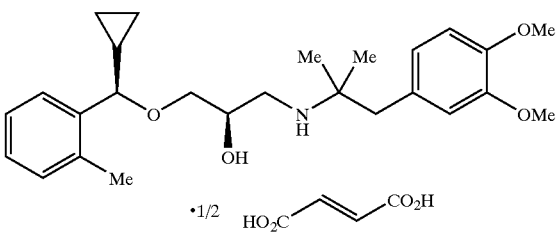 | $^1$H-NNR(300 MHz, δ ppm, DMSO-$d_6$)<br>7.40–7.10(4H, m), 6.86(1H, d, J=8.2 Hz),<br>6.77(1H, s), 6.70(1H, d, J=8.1 Hz),<br>6.47(1H, s), 3.90–3.60(7H, m), 3.40–<br>3.10(2H, m), 2.90–2.80(1H, m),<br>2.75–2.50(3H, m), 1.30–1.00(7H, m),<br>0.60–0.10(4H, m).<br>MS(ESI, m/z) 428(M + H-1/2$C_4H_4O_4$)$^+$. |

TABLE 13

| Ex. 94 | 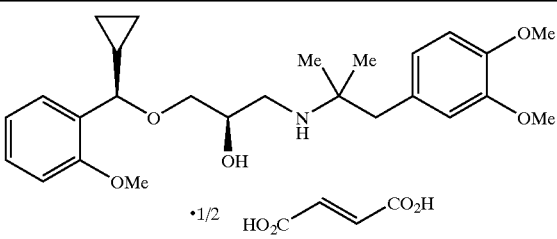 | $^1$H-NMR(300 MHz, δ ppm, DMSO-$d_6$)<br>7.40–7.10(4H, m), 7.10–6.90(2H, m), 6.881H, d,<br>J=8.2 Hz), 6.77(1H, s), 6.71(1H, d, J=8.2 Hz), 6.50(1H,<br>s), 4.27(1H, d, J=7.4 Hz), 3.95–3.65(10H, m), 3.40–<br>3.15(2H, m), 3.10–2.90(1H, m), 2.85–2.60(3H, m),<br>1.20–1.00(7H, m), 0.60–0.10(4H, m).<br>MS (ESI, m/z) 444(M + H-1/2$C_4H_4O_4$)$^+$. |
|---|---|---|
| Ex. 95 | 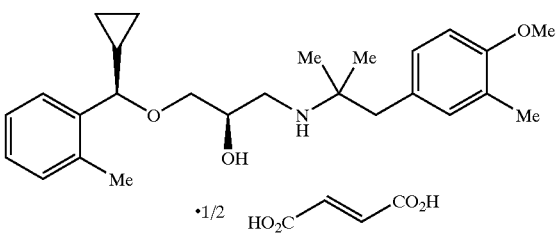 | $^1$H-NMR(300 MHz, δ ppm, DMSO-$d_6$)<br>7.40–6.90(6H, m), 6.87(1H, d, J=8.1 Hz), 6.53<br>(1H, m), 4.09(1H, d, J=7.5 Hz), 4.00–3.80(1H, m),<br>3.76(3H, s), 3.45–2.95(4H, m), 2.90–2.70(2H, m), 2.33<br>(3H, s),<br>2.13(3H, s), 1.20–1.00(7H, m), 0.60–0.10(4H, m).<br>MS(ESI, m/z) 412 (M + H-1/2$C_4H_4O_4$)$^+$. |
| Ex. 96 | 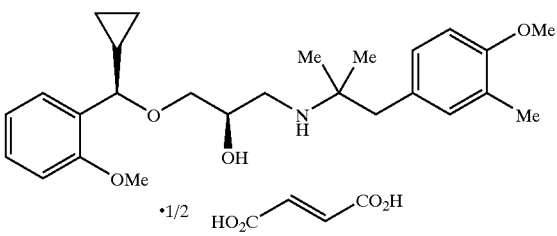 | $^1$H-NMR(300 MHz, δ ppm, DMSO-$d_6$)<br>7.40–7.15(2H, m), 7.05–6.90(4H, m), 6.89(1H,<br>d, J=8.1 Hz), 6.53(1H, m), 4.27(1H, d, J=7.5 Hz),<br>3.95–3.70(7H, m), 3.45–3.00(4H, m), 3.90–3.65(2H, m),<br>2.13(3H, s), 1.20–1.00(7H, m), 0.60–0.10(4H, m).<br>MS(ESI, m/z) 428(M + H-1/2$C_4H_4O_4$)$^+$. |
| Ex. 97 | 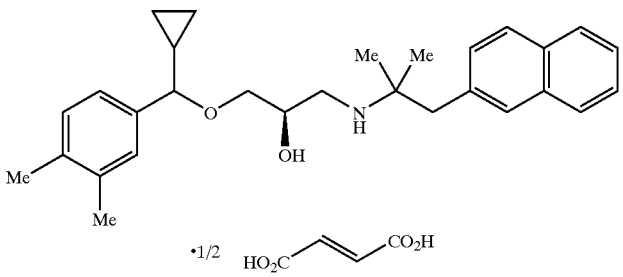 | $^1$H-NMR(300 MHz, δ ppm, CDCl$_3$) 7.82–7.76<br>(3H, m), 7.48(1H, s), 7.48–7.46(2H, m), 7.33–7.29(1H,<br>m), 7.11–6.99(3H, m), 6.88(1H, s), 4.24–4.12(1H, m),<br>3.61–3.38(3H, m), 3.23–2.82(4H, m), 2.25–2.23(6H,<br>m), 1.32–1.26(6H, m), 1.11–0.94(1H, m), 0.62–0.52(1H,<br>m), 0.46–0.35(2H, m), 0.20–0.14(1H, m).<br>MS(ESI, m/z) 432(M + H-1/2$C_4H_4O_4$)$^+$. |

TABLE 13-continued

Ex. 98 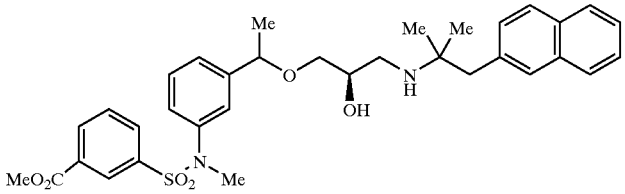
¹H-NMR(300 MHz, δ ppm, CDCl₃) 8.23–8.21 (2H, m), 7.79–7.74(4H, m), 7.65–7.62(2H, m), 7.50–7.43(3H, m), 7.29–7.17(2H, m), 7.10–6.90(2H, m), 4.38–4.34(1H, m), 3.91(3H, s), 3.80–3.70(1H, m), 3.31–3.28(2H, m), 3.19(3H, s), 2.89–2.69(4H, m), 1.33–1.30(3H, m), 1.14–1.12(6H, m).
MS(ESI, m/z) 605(M + H)⁺.

Ex. 99 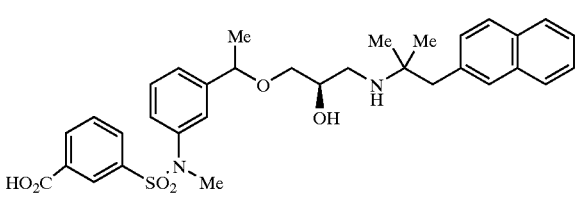
¹H-NMR(300 MHz, δ ppm, DMSO-d₆) 8.20–8.17(1H, m), 7.89–7.64(7H, m), 7.52–7.17(6H, m), 6.90–6.77(1H, m), 4.40–4.30(1H, m), 3.95–3.80(1H, m), 3.65–3.55(1H, m), 3.24–3.13(3H, m), 3.09(3H, s), 3.08–2.90(2H, m), 1.30–1.20(9H, m).
MS(ESI, m/z) 591(M + H)⁺.

TABLE 14

Ex. 100 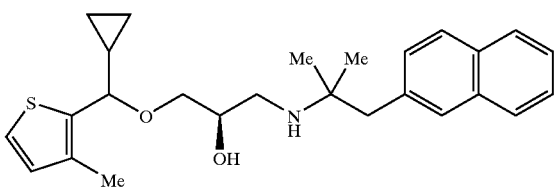
¹H-NMR(300 MHz, δ ppm, CDCl₃) 7.82–7.80(3H, m), 7.68–7.66(1H, m), 7.50–7.47(2H, m), 7.32–7.28(1H, m), 7.17–7.14(1H, m), 6.79–6.76(1H, m), 4.20–4.10(1H, m), 4.09–4.02(1H, m), 3.62–3.48(2H, m), 3.27–3.23(1H, m), 3.12–3.00(3H, m), 2.18–2.17(3H, m), 1.38–1.32(6H, m), 1.10–1.00(1H, m), 0.60–0.20(4H, m)
MS(ESI, m/z) 424(M + H)⁺.

Ex. 101 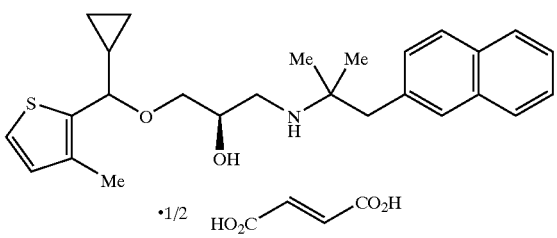
¹H-NMR(300 MHz, δ ppm, CDCl₃) 7.76–7.74(3H, m), 7.65(1H, s), 7.45–7.42(2H, m), 7.31–7.19(2H, m), 6.93–6.90(2H, m), 6.85(1H, s), 4.20–4.10(1H, m), 3.90(1H, dd, J=11.7, 8.1 Hz), 3.64–3.40(2H, m), 3.20–2.80(4H, m), 1.30–1.24(6H, m), 1.10–1.00(1H, m), 0.60–0.45(3H, m), 0.30–0.20(1H, m).
MS(APCI, m/z) 410(M + H-1/2C₄H₄O₄)⁺.

Ex. 102 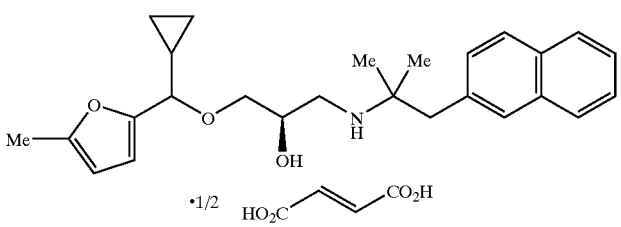
¹H-NMR(300 MHz, δ ppm, CDCl₃) 7.78–7.75(3H, m), 7.67(1H, s), 7.46–7.43(2H, m), 7.32–7.26(1H, m), 6.85(1H, s), 6.11–6.09(1H, m), 5.87(1H, s), 4.33(1H, brs), 4.20–4.10(1H, m), 3.60–3.45(3H, m), 3.20–2.80(3H, m), 2.24(3H, s), 1.28–1.22(6H, m), 1.20–1.10(1H, m), 0.60–0.30(3H, m), 0.20–0.10(1H, m).
MS(ESI, m/z) 408(M + H-1/2C₄H₄O₄)⁺.

Ex. 103 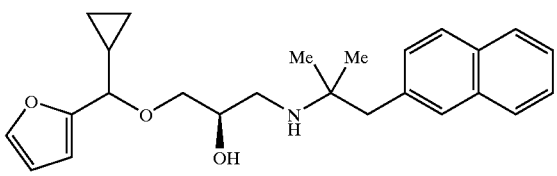
¹H-NMR(300 MHz, δ ppm, CDCl₃) 7.83–7.30(3H, m), 7.70(1H, s), 7.50–7.47(2H, m), 7.37–7.30(2H, m), 6.33–6.31(1H, m), 6.26–6.25(1H, m), 4.30–4.20(1H, m), 3.63–3.52(3H, m), 3.40–3.30(1H, m), 3.15–3.10(3H, m), 1.42–1.37(6H, m), 1.15–1.00(1H, m), 0.60–0.30(3H, m), 0.20–0.10(1H, m).
MS(ESI, m/z) 394(M + H)⁺.

Ex. 104 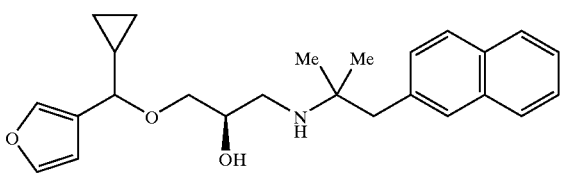
¹H-NMR(300 MHz, δ ppm, CDCl₃) 7.83–7.78(3H, m), 7.68(1H, brs), 7.49–7.46(2H, m), 7.38–7.29(3H, m), 6.36(1H, brs), 4.30–4.10(1H, m), 3.63–3.49(3H, m), 3.29–3.25(1H, m), 3.18–3.08(3H, m), 1.37–1.34(6H, m), 1.05–0.80(1H, m), 0.56–0.33(3H, m), 0.13–0.08(1H, m).
MS(ESI, m/z) 394(M + H)⁺.

TABLE 14-continued

| Ex. 105 | 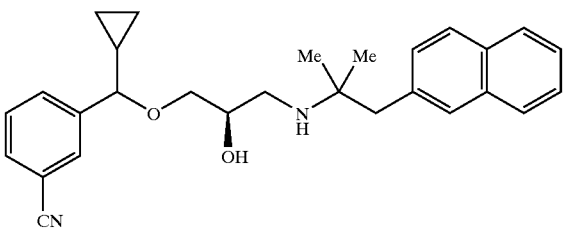 | ¹H-NMR(300 MHz, δ ppm, CDCl₃) 7.85–7.75(3H, m), 7.70–7.40(7H, m), 7.35–7.25(1H, m), 3.90–3.80(1H, m), 3.75–3.65(1H, m), 3.55–.3.35(2H, m), 300–2.85(3H, m), 2.85–2.70(1H, m), 1.29–0.95(7H, m), 0.70–0.60(1Hm,), 0.55–0.45(2H, m), 0.30–0.20(1H, m). MS(ESI, m/z) 429(M + H)⁺. |
|---|---|---|

TABLE 15

| Ex. 106 | 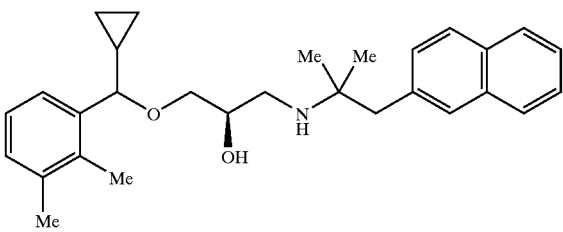 | ¹H-NMR(300 MHz, δ ppm, CDCl₃) 7.85–7.70(3H, m), 7.61(1H, s), 7.50–7.40(2H, m), 7.35–7.20(2H, m), 7.15–7.05(2H, m), 4.10(1H, m), 3.90–3.75(1H, m), 3.45–3.30(2H, m), 2.95–2.65(4H, m), 2.35–2.20 (6H, m) 1.35–1.00(7H, m), 0.65–0.55(1H, m), 0.50–0.20(3H, m). MS(ESI, m/z) 432(M + H)⁺. |
|---|---|---|
| Ex. 107 | 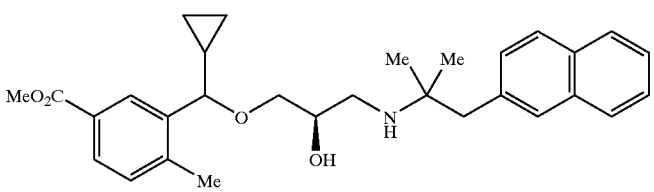 | ¹H-NMR(300 MHz, δ ppm, CDCl₃) 8.15–8.05(1H, m), 8.00–7.90(1H, m), 7.85–7.70(3H, m), 7.65–7.60(1H, m), 7.50–7.40(2H, m), 7.35–7.25(1H, m), 6.95–6.85(1H, m), 4.25–4.20(1H, m), 3.95–3.80(7H, m), 3.55–3.35(2H, m), 3.00–2.70(4H, m), 1.25–1.00(7H, m), 0.65–0.55(1H, m), 0.50–0.25(3H, m). MS(ESI, m/z) 492(M + H)⁺. |
| Ex. 108 | 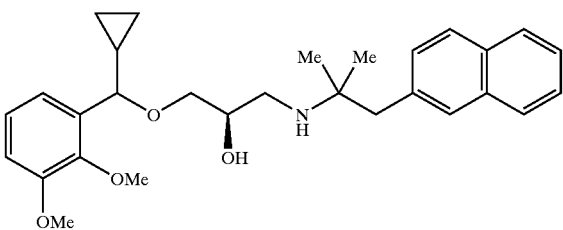 | ¹H-NMR(300 MHz, δ ppm, CDCl₃) 7.85–7.70(3H, m), 7.61(1H, s), 7.50–7.35(2H, m), 7.30–7.25(1H, m), 7.10–6.95(2H, m), 6.90–6.80(1H, m), 4.20–4.10(1H, m), 3.90–3.70(7H, m), 3.50–3.30(2H, m), 2.90–2.60(4H, m), 1.20–1.00(7H, m), 0.70–0.25(4H, m). MS(ESI, m/z) 464(M + H)⁺. |
| Ex. 109 | 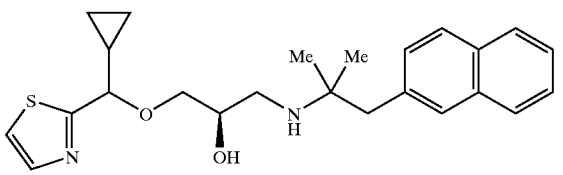 | ¹H-NMR(300 MHz, δ ppm, CDCl₃) 7.82–7.70(3H, m), 7.63(1H, s), 7.47–7.43(2H, m), 7.31–7.26(3H, m), 4.15(1H, dd, J=7.7, 5.7 Hz), 3.90–3.80(1H, m) 3.70–3.54(2H, m), 2.90–2.78(4H, m), 1.28–1.15(7H, m), 0.70–0.45(4H, m). MS(APCI, m/z) 411(M + H)⁺. |
| Ex. 110 | 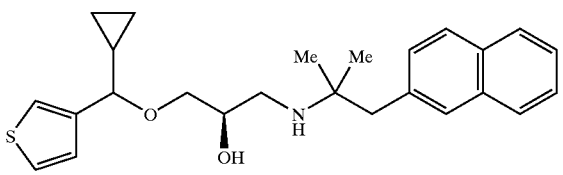 | ¹H-NMR(300 MHz, δ ppm, CDCl₃) 7.82–7.77(3H, m), 7.65(1H, s), 7.48–7.45(2H, m), 7.31–7.25(2H, m), 7.14(1H, s), 7.04–7.01(1H, m), 4.07–4.00(1H, m), 3.72–3.67(1H, m), 3.60–3.46(2H, m), 3.16–2.90(4H, m), 1.28–1.26(6H, m), 1.10–0.95(1H, m), 0.60–0.35(3H, m), 0.20–0.15(1H, m). MS(APCI, m/z) 409(M + H)⁺. |
| Ex. 111 | 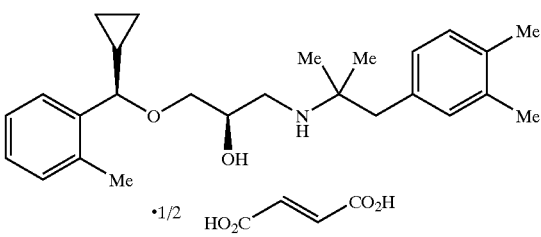 | ¹H-NMR(300 MHz, δ ppm, DMSO-D₆) 7.40–7.10(4H, m), 7.07(1H, d, J=7.8 Hz), 6.96(1H, s) 6.91(1H, d, J=7.8Hz), 6.53(1H, s), 4.101H, d, J= 7.5 Hz), 4.00–3.80(1H, m), 3.40–3.00(3H, m), 2.90–2.70(3H, m), 2.33(3H, s), 2.20(3H, s), 2.19(3H, s), 1.20–1.00(7H, m), 0.60–0.10(4H, m). MS(ESI, m/z) 396(M + H-1/2C₄H₄O₄)⁺. |

TABLE 15-continued

| Ex. 112 | 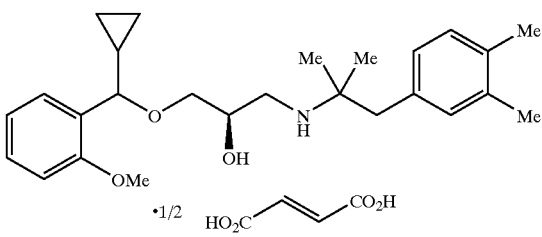 | $^1$H-NMR(300 MHz, δ ppm, DMSO-D$_6$) 7.40–7.20(4H, m), 7.15–6.85(5H, m), 6.46(1H, s), 4.35–4.20(1H, m), 3.90–3.65(4H, m), 3.40–3.10(2H, m), 2.95–2.65(4H, m), 2.18(6H, s)1.20–1.0(7H, m), 0.60–0.10(4H, m).<br>MS (ESI, m/z) 412 (M + H-1/2C$_4$H$_4$O$_4$)$^+$. |

TABLE 16

| Ex. 113 | 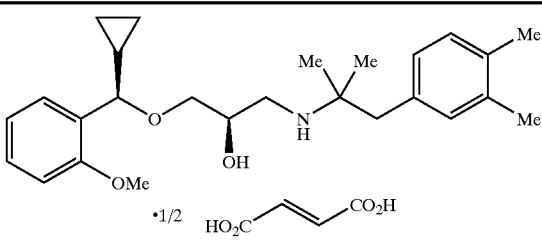 | $^1$H-NMR(300 MHz, δ ppm, CDCl$_3$) 7.40–7.20(4H, m), 7.15–6.85(5H, m), 6.53(1H, s), 4.27(1H, d, J=7.5 Hz), 3.95–3.70(4H, m), 3.50–3.00(8H, m), 2.95–2.70(3H, m), 2.20(3H, s), 2.19(3H, s), 1.20–1.00(7H, m), 0.60–0.10(4H, m).<br>MS(ESI, m/z) 412(M + H-1/2C$_4$H$_4$O$_4$)$^+$. |
| Ex. 114 | 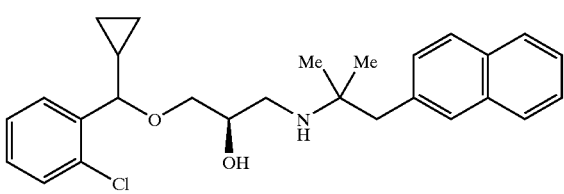 | $^1$H-NMR(300 MHz, δ ppm, CDCl$_3$) 7.85–7.70(3H, m), 7.61(1H, s), 7.50–7.40(3H, m), 7.35–7.15(4H, m), 4.40–4.30(1H, m), 3.90–3.75(1H, m), 3.50–3.30(2H, m), 2.95–2.65(4H, m), 1.20–1.00(7H, m), 0.65–0.50(1H, m), 0.50–0.35(3H, m).<br>MS(ESI, m/z) 438(M + H)$^+$. |
| Ex. 115 | 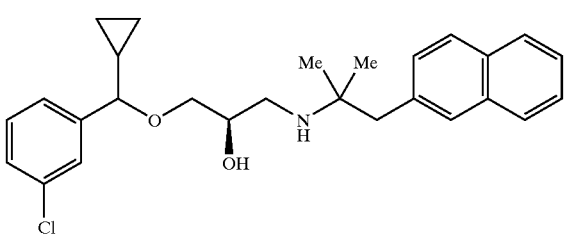 | $^1$H-NMR(300 MHz, δ ppm, CDCl$_3$) 7.85–7.70(3H, m), 7.62(1H, s), 7.50–7.40(2H, m), 7.35–7.10(5H, m), 3.85–3.75(1H, m), 3.70–3.55(1H, m), 3.50–3.30(2H, m), 2.95–2.65(4H, m), 1.20–1.00(7H, m), 0.70–0.55(1H, m), 0.50–0.40(2H, m), 0.30–0.20(1H, m).<br>MS(ESI, m/z) 438(M + H)$^+$. |
| Ex. 116 | 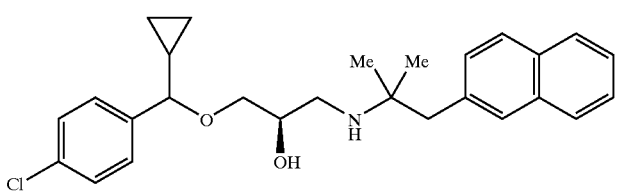 | $^1$H-NMR(300 MHz, δ ppm, CDCl$_3$) 7.85–7.70(3H, m), 7.61(1H, s), 7.50–7.40(2H, m), 7.35–7.15(5H, m), 3.85–3.75(1H, m), 3.70–3.60(1H, m), 3.50–3.30(2H, m), 2.90–2.80(3H, m), 2.75–2.65(1H, m), 1.20–1.00(7H, m), 0.70–0.60(1H, m), 0.50–0.40(2H, m), 0.30–0.20(1H, m).<br>MS(ESI, m/z) 438(M + H)$^+$. |
| Ex. 117 | 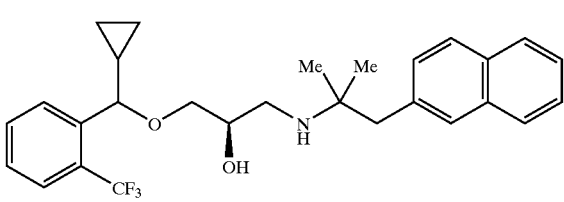 | $^1$H-NMR(300 MHz, δ ppm, CDCl$_3$) 7.85–7.25(11H, m), 4.35–4.20(1H, m), 3.80–3.70(1H, m), 3.45–3.35(1H, m), 3.30–3.15(1H, m), 2.90–2.75(3H, m), 2.75–2.60(1H, m), 1.20–1.00(7H, m), 0.65–0.30(4H, m).<br>MS(ESI, m/z) 472(M + H)$^+$. |
| Ex. 118 | 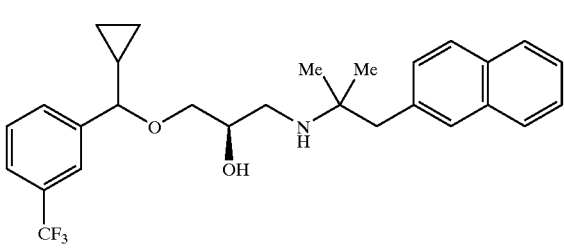 | $^1$H-NMR(300 MHZ, δ ppm, CDCl$_3$) 7.85–7.70(3H, m), 7.65–7.40(7H, m), 7.35–7.25(1H, m), 3.90–3.70(2H, m), 3.50–3.30(2H, m), 2.95–2.60(4H, m), 1.20–1.00(7H, m), 0.70–0.60(1H, m), 0.55–0.40(2H, m), 0.30–0.20(1H, m).<br>MS(ESI, m/z) 472(M + H)$^+$. |

TABLE 16-continued

| Ex. 119 | 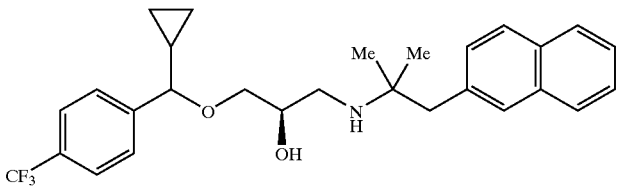 | $^1$H-NMR(300 MHz, δ ppm, CDCl$_3$) 7.85–7.70(3H, m), 7.65–7.55(3H, m), 7.50–7.35(4H, m), 7.35–7.25(1H, m), 3.85–3.70(2H, m), 3.50–3.30(2H, m), 2.95–2.80(3H, m), 2.80–2.65(1H, m), 1.20–1.00(7H, m), 0.70–0.55(1H, m), 0.50–0.40(2H, m), 0.30–0.20(1H, m). MS(ESI, m/z) 472(M + H)$^+$. |

TABLE 17

| Ex. 120 | 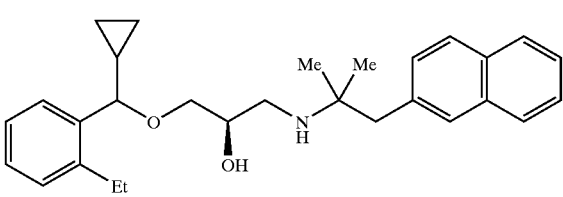 | $^1$H-NMR(300 MHz, δ ppm, CDCl$_3$) 7.90–7.77(3H, m), 7.64(1H, brs), 7.63–7.46(2H, m), 7.32–7.18(5H, m), 4.17–4.08(2H, m), 3.59–3.53(1H, m), 3.45–3.43(1H, m), 3.26–3.22(1H, m), 3.10–3.03(3H, m), 2.66–2.59(2H, m), 1.32–1.28(6H, m), 1.22–1.17(3H, m), 1.11–1.00(1H, m), 0.60–0.50(1H, m), 0.40–0.30(2H, m), 0.25–0.20(1H, m). MS(ESI, m/z) 432(M + H)$^+$. |
| Ex. 121 | 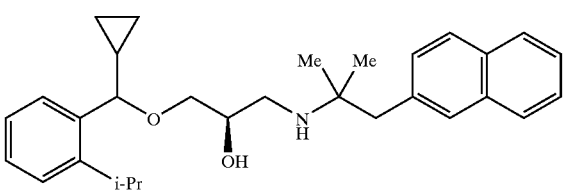 | $^1$H-NMR(300 MHz, δ ppm, CDCl$_3$) 7.90–7.78(3H, m), 7.65(1H, brs), 7.50–7.46(2H, m), 7.29–7.17(5H, m), 4.21–4.11(2H, m), 3.60–3.52(1H, m), 3.45–3.42(1H, m), 3.30–3.05(4H, m), 1.34–1.18(12H, m), 1.20–1.00(1H, m), 0.60–0.50(1H, m), 0.40–0.30(2H, m), 0.20–0.10(1H, m). MS(ESI, m/z) 446(M + H)$^+$. |
| Ex. 122 | 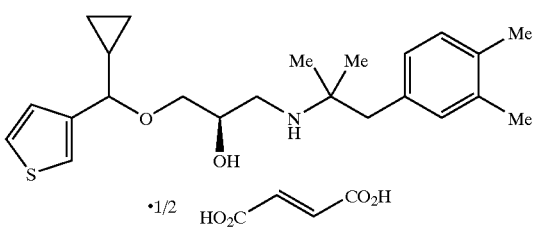 | $^1$H-NMR(300 MHz, δ ppm, DMSO-d$_6$) 7.96–7.82(3H, m), 7.73(1H, s), 7.50–7.47(3H, m), 7.41–7.38(2H, m), 7.13(1H, d, J=5.1 Hz), 3.90–3.81(2H, m), 3.44–3.28(3H, m), 3.10–2.70(4H, m), 1.20–1.05(7H, m), 0.60–0.50 (1H, m), 0.45–0.35(2H, m), 0.30–0.20(1H, m). MS(ESI, m/z) 410(M + H-1/2C$_4$H$_4$O$_4$)$^+$. |
| Ex. 123 | 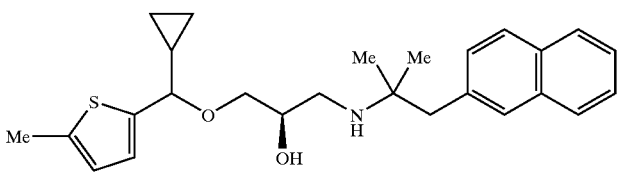 | $^1$H-NMR(300 MHz, δ ppm, CDCl$_3$) 7.84–7.78(3H, m), 7.66(1H, s), 7.48–7.46(2H, m), 7.32–7.29(1H, m), 6.72(1H, t, J=3.0 Hz), 6.58(1H, s), 4.16–4.06(1H, m), 3.81–3.75(1H, m), 3.61–3.54(2H, m), 3.22–3.16(1H, m), 3.06–2.95(3H, m), 2.44(1H,d, J=3.0 Hz), 1.32–1.28 (6H, m), 1.16–1.06(1H, m), 0.62–0.42(3H, m), 0.30–0.20(1H, m). MS(ESI, m/z) 424(M + H)$^+$. |
| Ex. 124 | 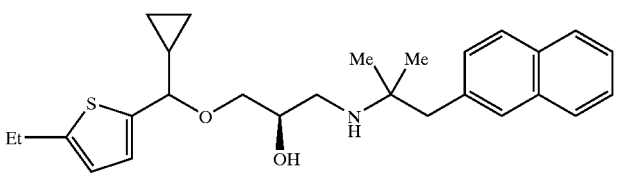 | $^1$H-NMR(300 MHz, δ ppm, CDCl$_3$) 7.83–7.78(3H, m), 7.66(1H, s), 7.49–7.45(2H, m), 7.31–7.28(1H, m), 6.74(1H, t, J=3.4 Hz), 6.62–6.60(1H, m), 4.14–4.09 (1H, m), 3.79(1H, t, J=8.5 Hz), 3.62–3.50(2H, m), 3.24–3.02(4H, m), 2.84–2.75(2H, m), 1.32–1.23(9H, m), 1.12–1.04(1H, m), 0.66–0.40(3H, m), 0.28–0.20(1H, m). MS(ESI, m/z) 437(M + H)$^+$. |
| Ex. 125 | 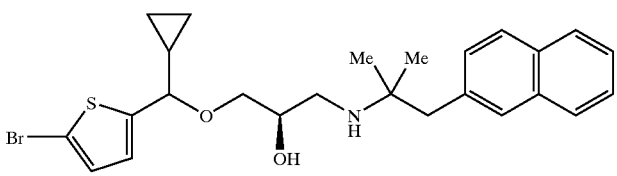 | $^1$H-NMR(300 MHz, δ ppm, CDCl$_3$) 7.81–7.79(3H, m), 7.68(1H, s), 7.49–7.45(2H, m), 7.32–7.29(1H, m), 6.88(1H, t, J=3.7 Hz), 6.70(1H, d, J=6.7 Hz), 4.14–4.08(1H, m), 3.79(1H, t, J=8.7 Hz), 3.62–3.50(2H, m), 3.22–2.90(4H, m), 1.34–1.30(6H, m), 1.10–1.00(1H, m), 0.60–0.40(3H, m), 0.30–0.20(1H, m). MS(ESI, m/z) 490(M + H)$^+$. |

TABLE 18

| Ex. 126 | 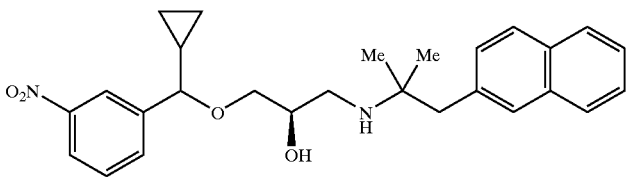 | ¹H-NMR(300 MHz, δ ppm, CDCl₃) 8.20–8.05(2H, m), 7.85–7.70(3H, m), 7.70–7.60(2H, m), 7.55–7.40(3H, m), 7.35–7.25(1H, m), 3.85–3.70(2H, m), 3.55–3.35(2H, m), 2.95–2.60(4H, m), 1.20–1.00(7H, m), 0.70–0.60(1H, m), 0.55–0.40(2H, m), 0.35–0.20(1H, m). MS(ESI, m/z) 449(M +⁺H)⁺. |
|---|---|---|
| Ex. 127 | 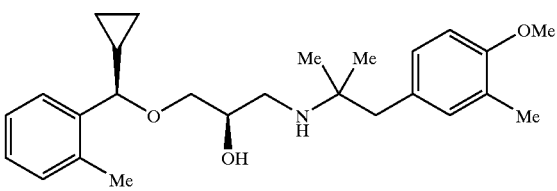 | ¹H-NMR(300 MHz, δ ppm, CDCl₃) 7.40–7.10(4H, m), 7.00–6.85(3H, m), 6.75(1H, d, J=8.2 Hz), 4.20–4.00(3H, m), 3.80(3H, s), 3.60–3.30(2H, m), 3.20–2.80(2H, m), 2.73(2H, s), 2.32(3H, s), 2.18(3H, s), 1.30–1.00(7H, m), 0.70–0.10(4H, m). MS(ESI, m/z) 412(M + H)⁺. |
| Ex. 128 | 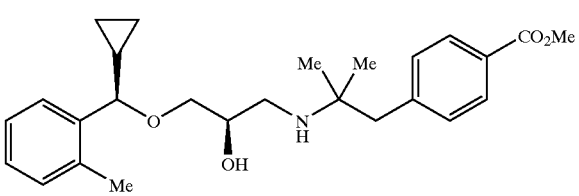 | ¹H-NMR(300 MHz, δ ppm, CDCl₃) 7.98–7.95(2H, d, J=8.3 Hz), 7.36–7.34(1H, m), 7.24–7.16(5H, m), 4.11–4.08(1H, d, J=7.7 Hz), 4.05–3.95 (1H, m), 3.91(3H, s), 3.52–3.37(2H, m), 3.05–3.01(1H, m), 2.88–2.85(1H, m), 2.34(3H, s), 1.23–1.20(1H, m), 1.14(6H, s), 0.70–0.55(1H, m), 0.50–0.20(3H, m). MS(ESI, m/z) 426(M + H)⁺. |
| Ex. 129 | 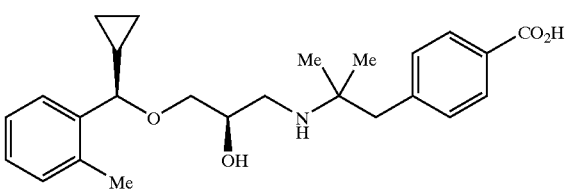 | ¹H-NMR(300 MHz, δ ppm, DMSO-d₆) 7.86–7.83(2H, d, J=8.1 Hz), 7.34–7.14(6H, m), 4.10–4.07(1H, d, J=7.5 Hz), 3.80–3.70(1H, m), 3.35–3.30(2H, m), 3.22–3.17(1H, m), 2.87–2.81(3H, m), 2.66–2.59(1H, m), 2.32(3H, s), 1.25–1.10 (1H, m), 1.05–1.04(6H, s), 0.60–0.15(4H, m). MS(ESI, m/z) 412 (M + H)⁺. |
| Ex. 130 | 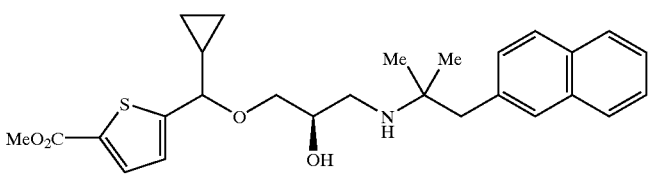 | ¹H-NNR(300 MHz, δ ppm, CDCl₃) 7.81–7.76(3H, m), 7.65–7.63(2H, m), 7.48–7.45(2H, m), 7.32–7.29(1H, m), 6.94(1H, d, J=3.7 Hz), 4.10–4.06(1H, m), 3.90–3.84(4H, m), 3.64–3.60(1H, m), 3.56–3.50(1H, m), 3.18–2.90(4H, m), 1.30–1.28(6H, m), 1.12–1.02(1H, m), 0.68–0.46(3H, m), 0.32–0.24(1H, m). MS(ESI, m/z) 468(M + H)⁺. |
| Ex. 131 | 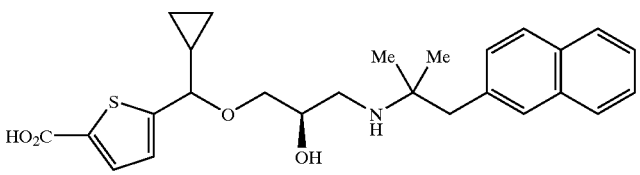 | ¹H-NMR(300 MHz, δ ppm, DMSO-d₆) 7.91–7.85(3H, m), 7.73(1H, s), 7.49–7.46(3H, m), 7.36(1H, d, J=8.1 Hz), 7.03(1H, s), 4.06(1H, d, J=8.1 Hz), 3.89–2.80(7H, m), 1.24–1.19(7H, m), 0.60–0 20 (4H, m). MS(ESI, m/z) 454(M + H)⁺. |
| Ex. 132 | 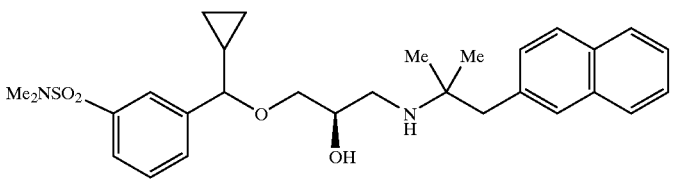 | ¹H-NMR(300 MHz, δ ppm, CDCl₃) 7.85–7.40(10H, m), 7.35–7.30(1H, m), 3.85–3.70(2H, m), 3.50–3.35(2H, m), 3.00–2.85(3H, m), 2.80–2.65 (7H, m), 1.20–1.00(7H, m), 0.70–0.60(1H, m), 0.55–0.40(2H, m), 0.30–0.20(1H, m). MS(ESI, m/z) 511(M + H)⁺. |

TABLE 19

| Ex. 133 | 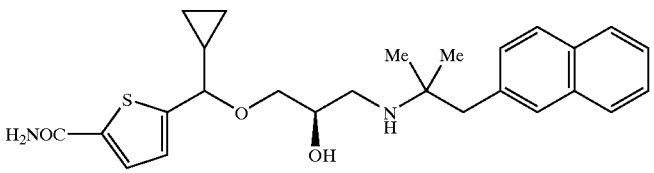 | ¹H-NNR(300 MHz, δ ppm, DMSO-d₆) 7.87–7.77(3H, m), 7.67(1H, s), 7.60(1H, d, J=3.7 Hz), 7.46–7.44 (2H, m), 7.37–7.35(1H, m), 7.01(1H, d, J=3.7 Hz), 3.99(1H, dd, J=7.8, 3.2 Hz), 3.65–3.60(1H, m), 3.45–3.33(2H, m), 2.78–2.70(4H, m), 1.10–0.97(7H, m), 0.60–0.40(3H, m), 0.32–0.26(1H, m). MS(ESI, m/z) 453(M + H)⁺. |
|---|---|---|

TABLE 19-continued

| | | |
|---|---|---|
| Ex. 134 | 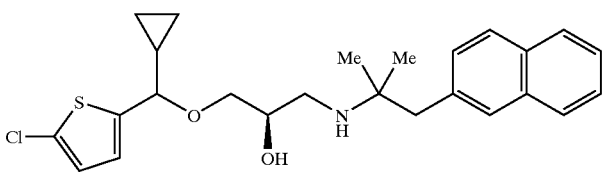 | $^1$H-NMR(300 MHz, δ ppm, CDCl$_3$) 7.83–7.80(3H, m), 7.68(1H, s), 7.49–7.46(2H, m), 7.31(1H, d, J=8.4 Hz), 6.75–6.70(2H, m), 4.18–4.12(1H, m), 3.75(1H, t, J=9.3 Hz), 3.64–3.51(2H, m) 3.23–2.99(4H, m), 1.36–0.95(7H, m), 0.70–0.40(3H, m), 0.30–0.20(1H, m). MS (ESI, m/z) 444(M + H)$^+$. |
| Ex. 135 | 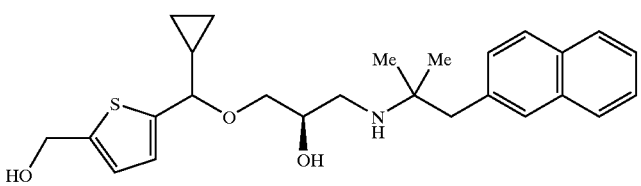 | $^1$H-NNR(300 MHz, δ ppm, DMSO-d$_6$) 7.88–7.78(3H, m), 7.68(1H, s), 7.49–7.45(2H, m), 7.37(1H, d, J=8.4 Hz), 6.82(2H, dd, J=14.7, 3.3 Hz), 5.37(1H, t, J=5.4 Hz), 3.94(1H, dd, J=8.1, 3.3 Hz), 3.64(1H, brs), 3.38–3.17(2H, m), 2.81–2.75(2H, m), 1.14–1.06(7H, m), 0.60–0.50(1H, m), 0.48–0.40(2H, m), 0.30–0.20(1H, m). MS(ESI, m/z) 440(M + H)$^+$. |
| Ex. 136 | 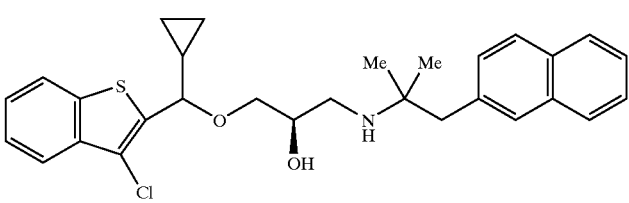 | $^1$H-NMR(300 MHz, δ ppm, CDCl$_3$) 7.80–7.74(5H, m), 7.62(1H, s), 7.47–7.39(4H, m), 7.27–7.25(1H, m,) 4.37(1H, dd, J=14.4, 7.8 Hz), 4.10–4.04(1H, m), 3.63–3.48 (2H, m), 3.16–2.97(4H, m), 1.28–1.10(7H, m), 0.63–0.42(4H, m). MS(ESI, m/z) 494(M + H)$^+$. |
| Ex. 137 | 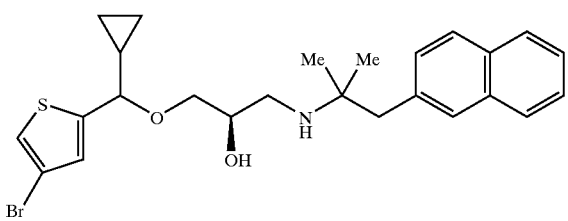 | $^1$H-NMR(300 MHz, δ ppm, CDCl$_3$) 7.82–7.77(3H, m), 7.67(1H, s), 7.48–7.45(2H, m), 7.30(1H, d, J=8.4 Hz), 7.12(1H, dd, J=4.7, 1.4 Hz), 6.86(1H, s), 4.16–4.06(1H, m), 3.80(1H, t, J=8.8 Hz), 3.62–3.50(2H, m), 3.24–2.97(4H, m), 1.34–1.25(6H, m), 1.06–1.02 (1H, m), 0.60–0.40(3H, m), 0.30–0.20(1H, m). MS(ESI, m/z) 490(M + H)$^+$. |
| Ex. 138 | 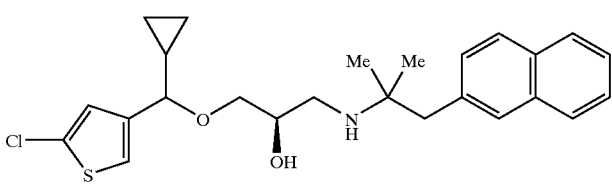 | $^1$H-NMR(300 MHz, δ ppm, CDCl$_3$) 7.81–7.78(3H, m), 7.68(1H, s), 7.49–7.46(2H, m), 7.30(1H, d, J=8.4 Hz), 6.90(1H, s), 6.81(1H, dd, J=3.2, 1.7 Hz), 4.20–4.14(1H, m), 3.62–3.06(7H, m), 1.38–1.35(6H, m), 1.00–0.70(1H, m), 0.60–0.30(3H, m), 0.20–0.10(1H, m). MS(ESI, m/z) 444(M + H)$^+$. |

TABLE 20

| | | |
|---|---|---|
| Ex. 139 | 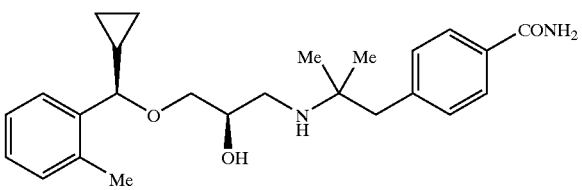 | $^1$H-NMR(300 MHz, δ ppm, CDCl$_3$) 7.72–7.70(2H, d, J= 8.2 Hz), 7.38–7.26(1H, m), 7.24–7.16(5H, m), 6.30–5.50 (2H, br), 4.13–4.10(1H, d, J=7.4 Hz), 3.85–3.70(1H, m), 3.35–3.29(2H, m), 2.78–2.59(4H, m), 2.35(3H, s), 1.30–1.20(1H, m), 1.04(3H, s) 1.02(3H, s), 0.65–0.20(4H, m). MS(ESI, m/z) 411(M + H)$^+$. |
| Ex. 140 | 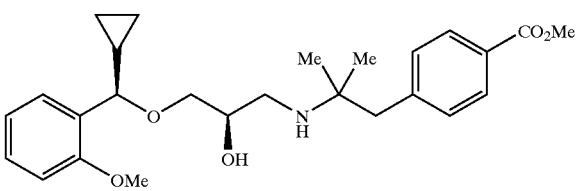 | $^1$H-NMR(300 MHz, δ ppm, DMSO-d$_6$) 7.89(2H, d, J=8.1Hz), 7.36–7.33(3H, m), 7.28–7.22(1H, m), 7.01–6.94(2H, m), 4.30–4.26(1H, m), 4.08–3.76(7H, m), 3.24–3.16(2H, m), 2.86(3H, brs), 2.76–2.64(1H, m), 1.12–1.08(7H, m), 0.50–0.40(1H, m), 0.45–0.20(3H, m). MS(ESI, m/z) 442(M + H)$^+$. |

TABLE 20-continued

| Ex. 141 | 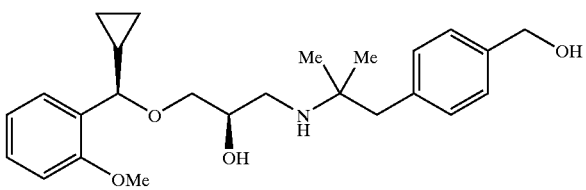 | ¹H-NMR(300 MHz, δ ppm, DMSO-d₆) 7.36–7.32(1H, m), 7.27–7.18(3H, m), 7.18–7.11(2H, m), 7.00–6.93(2H, m), 5.12–5.04(1H, m), 4.45(2H, d, J=4.5 Hz), 4.28(1H, d, J= 6.9 Hz), 4.07(1H, brs), 3.77(3H, s), 3.61(1H, brs), 3.24–3.17 (3H, m), 2.70–2.59(2H, m), 1.10–1.00(1H, m), 0.94–0.92 (6H, m), 0.50–0.40(1H, m), 0.30–0.20(3H, m). MS(ESI, m/z) 414(M + H)⁺. |
| --- | --- | --- |
| Ex. 142 | 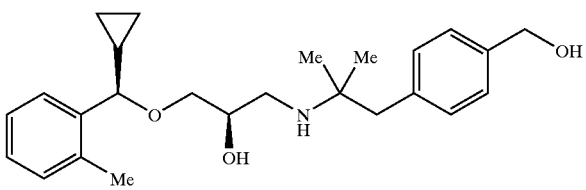 | ¹H-NMR(300 MHz, δ ppm, DMSO-d₆) 7.33–7.31(1H, m), 7.20–7.08(7H, m), 5.09(1H, t, J=5.7 Hz), 4.45(2H, d, J=5.5 Hz), 4.11–4.06(4H, m), 3.60(1H, brs), 3.30–3.24(1H, m), 2.70–2.57(2H, m), 2.31(3H, s), 1.20–1.10(1H, m), 0.93–0.91(6H, m), 0.55–0.45(1H, m), 0.40–0.30(2H, m), 0.25–0.15(1H, m). MS(ESI, m/z) 398(M + H)⁺. |
| Ex. 143 | 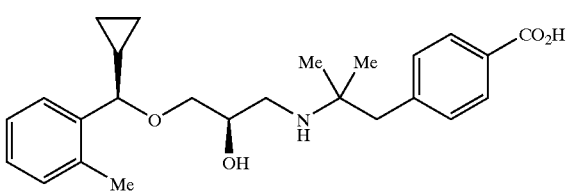 | ¹H-NMR(300 MHz, δ ppm, DMSO-d₆) 7.91(2H, d, J= 8.1 Hz), 7.36–7.24(4H, m), 7.02–6.96(2H, m), 4.31–4.26 (1H, m), 3.88(1H, brs), 3.78(3H, s), 3.20–2.85(4H, m), 2.60–2.50(2H, m), 1.18(7H, brs), 0.60–0.40(1H, m), 0.40–0.20(3H, m). MS(ESI, m/z) 428(M + H)⁺. |
| Ex. 144 | 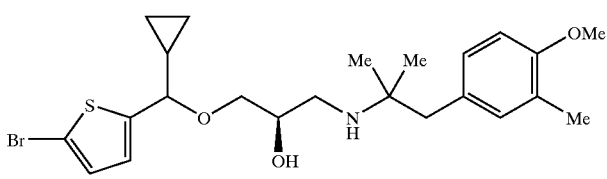 | ¹H-NMR(300 MHz, δ ppm, CDCl₃) 7.00–6.89(3H, m), 6.78–6.73(2H, m), 4.22–4.18(1H, m), 3.87–3.83(1H, m), 3.80(3H, s), 3.65–3.53(2H, m), 3.30–3.20(1H, m), 3.12–3.01(1H, m), 2.88–2.85(2H, m), 2.18(3H, s), 1.33(6H, d, J=11.1 Hz), 1.15–1.00(1H, m), 0.70–0.45 (3H, m), 0.30–0.20(1H, m). MS(ESI m/z) 484(M + H)⁺. |

TABLE 21

| Ex. 145 | 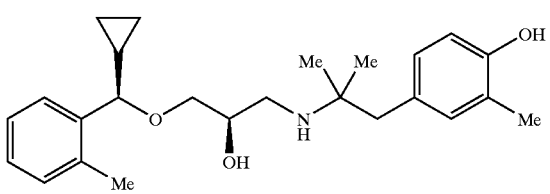 | ¹H-NMR(300MHz, δppm, DMSO-d₆) 9.18(1H, s), 7.40–7.10(4H, m), 6.90–6.60(3H, m), 4.20–4.00((2H, m), 3.95–3.75(1H, m), 3.40–2.90(3H, m), 2.85–2.60(3H, m), 2.33(3H, s), 2.09(3H, s)1.30–1.00(7H, m), 0.60–0.10(4H, m). MS(ESI, m/z) 398(M + H)⁺. |
| --- | --- | --- |
| Ex. 146 | 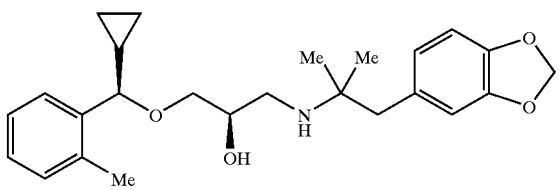 | ¹H-NMR(300MHz, δppm, CDCl₃) 7.40–7.30(1H, m), 7.20–7.00(3H, m), 6.80–6.50(3H, m), 5.93(2H, s), 4.10(1H, d, J=7.6Hz), 3.95–3.75(1H, m), 3.50–3.20(2H, m), 3.00–2.55(4H, m), 2.34(3H, s), 1.30–1.00(7H, m), 0.70–0.10(4H, m). MS(ESI, m/z) 412(M + H)⁺. |
| Ex. 147 | 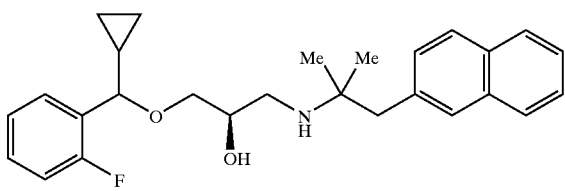 | ¹H-NMR(300MHz, δppm, CDCl₃) 7.85–7.70(3H, m), 7.61(1H, s), 7.50–7.35(3H, m), 7.35–6.95(4H, m), 4.15–4.05(1H, m), 3.80–3.70(1H, m), 3.50–3.30(2H, m), 2.90–2.60(4H, m), 1.20–1.00(7H, m), 0.70–0.55(1H, m), 0.50–0.25(3H, m). MS(ESI, m/z) 422(M + H)⁺. |

TABLE 21-continued

| Ex. 148 | (structure) | ¹H-NMR(300MHz, δppm, CDCl₃) 7.85–7.70(3H, m), 7.62(1H, s), 7.50–7.40(2H, m), 7.35–7.20(2H, m), 7.10–6.90(3H, m), 3.90–3.75(1H, m), 3.66(1H, t, J=8.1Hz), 3.50–3.30(2H, m), 2.95–2.60(4H, m), 1.20–1.00(7H, m), 0.70–0.55(1H, m), 0.50–0.40(2H, m), 0.30–0.20(1H, m). MS(ESI, m/z) 422(M + H)⁺. |
|---|---|---|
| Ex. 149 | (structure) | ¹H-NMR(300MHz, δppm, CDCl₃) 7.85–7.70(3H, m), 7.61(1H, s), 7.50–7.40(2H, m), 7.35–7.20(3H, m), 7.10–6.95(2H, m), 3.85–3.75(1H, m), 3.66(1H, t, J=7.8Hz), 3.45–3.30(2H, m), 2.90–2.65(4H, m), 1.20–1.00(7H, m), 0.70–0.55(1H, m), 0.50–0.35(2H, m), 0.30–0.15(1H, m). MS(ESI, m/z) 422(M + H)⁺. |
| Ex. 150 | (structure) | ¹H-NMR(300MHz, δppm, CDCl₃) 7.85–7.70(3H, m), 7.61(1H, s), 7.55–7.40(4H, m), 7.40–7.20(2H, m), 7.20–7.05(1H, m), 4.40–4.35(1H, m), 3.80–3.70(1H, m), 3.45–3.25(2H, m), 2.90–2.60(4H, m), 1.20–1.00(7H, m), 0.60–0.35(4H, m). MS(ESI, m/z) 483(M + H)⁺. |
| Ex. 151 | (structure) | ¹H-NMR(300MHz, δppm, CDCl₃) 7.85–7.70(3H, m), 7.61(1H, s), 7.50–7.10(7H, m), 3.85–3.70(1H, m), 3.63(1H, t, J=7.2Hz), 3.50–3.30(2H, m), 2.95–2.60(4H, m), 1.20–1.00(7H, m), 0.70–0.55(1H, m), 0.50–0.40(2H, m), 0.30–0.20(1H, m). MS(ESI, m/z) 483(M + H)⁺. |

TABLE 22

| Ex. 152 | (structure) | ¹H-NMR(300MHz, δppm, CDCl₃) 7.85–7.70(3H, m), 7.61(1H, s), 7.50–7.40(4H, m), 7.35–7.20(1H, m), 7.20–7.10(2H, m), 3.85–3.75(1H, m), 3.63(1H, t, J=7.8Hz), 3.45–3.30(2H, m), 2.95–2.80(3H, m), 2.80–2.65(1H, m), 1.20–1.00(7H, m), 0.70–0.55(1H, m), 0.50–0.35(2H, m), 0.30–0.15(1H, m). MS(ESI, m/z) 483(M + H)⁺. |
|---|---|---|
| Ex. 153 | (structure) | ¹H-NMR(300MHz, δppm, CDCl₃) 7.85–7.70(3H, m), 7.61(1H, s), 7.50–7.40(2H, m), 7.35–7.25(1H, m), 6.90–6.75(3H, m), 3.95–3.75(7H, m), 3.61(1H, t, J=8.5Hz), 3.50–3.35(2H, m), 2.95–2.80(3H, m), 2.80–2.65(1H, m), 1.20–1.00(7H, m), 0.70–0.55(1H, m), 0.50–0.40(2H, m), 0.30–0.15(1H, m). MS(APCI, m/z) 464(M + H)⁺. |

TABLE 22-continued

| Ex. | | |
|---|---|---|
| Ex. 154 | 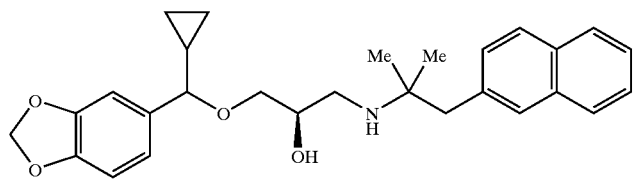 | ¹H-NMR(300MHz, δppm, CDCl₃) 7.85–7.70(3H, m), 7.61(1H, s), 7.50–7.40(2H, m), 7.35–7.25(1H, m), 6.83(1H, s), 6.80–6.65(2H, m), 5.94(2H, d, J=1.1Hz), 3.85–3.70(1H, m), 3.57(1H, t, J=7.7Hz), 3.40–3.30(2H, m), 2.90–2.80(3H, m), 2.80–2.65(1H, m), 1.20–1.00(7H, m), 0.65–0.55(1H, m), 0.50–0.35(2H, m), 0.30–0.15(1H, m).<br>MS(APCI, m/z) 448(M + H)⁺. |
| Ex. 155 | 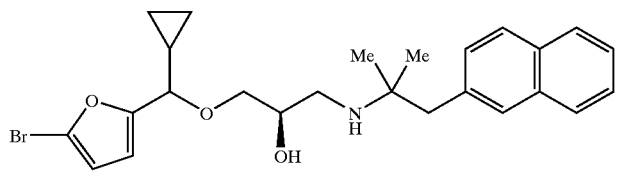 | ¹H-NMR(300MHz, δppm, CDCl₃) 7.85–7.70(3H, m), 7.63(1H, s), 7.50–7.40(2H, m), 7.35–7.30(1H, m), 6.24–6.23(2H, m), 3.90–3.75(1H, m), 3.70–3.60(1H, m), 3.60–3.45(2H, m), 2.95–2.85(3H, m), 2.85–2.65(1H, m), 1.30–1.05(7H, m), 0.70–0.60(1H, m), 0.60–0.40(2H, m), 0.30–0.20(1H, m).<br>MS(APCI, m/z) 473(M + H)⁺. |
| Ex. 156 | 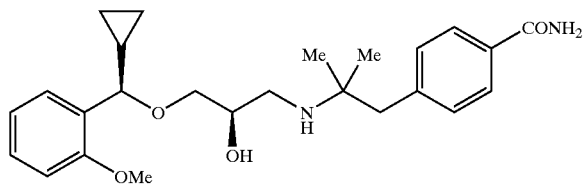 | ¹H-NMR(300MHz, δppm, DMSO-d₆) 7.95–7.80(2H, m), 7.36–7.23(4H, m), 7.01–6.95(2H, m), 4.31–4.27(1H, n), 4.08(1H, brs), 3.84(1H, brs), 3.78(3H, s), 3.31–2.73(5H, m), 1.11(7H, brs), 0.50–0.20(4H, m).<br>MS(ESI, m/z) 427(M + H)⁺. |
| Ex. 157 | 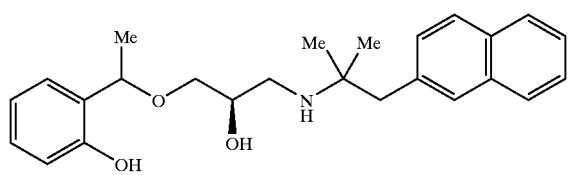 | ¹H-NMR(300MHz, δppm, CDCl₃) 7.82–7.71(3H, m), 7.61(1H, s), 7.45–7.42(2H, m), 7.32–7.20(3H, m), 6.97(1H, t, J=7.4Hz), 6.88(1H, d, J=8.1Hz), 5.08–5.03(1H, m), 4.10–3.90(3H, m), 3.00–2.80(4H, m), 1.52(3H, dd, J=6.6, 1.4Hz), 1.14(6H, d, J=4.9Hz).<br>MS(ESI, m/z) 394(M + H)⁺. |

TABLE 23

| Ex. | | |
|---|---|---|
| Ex. 158 | 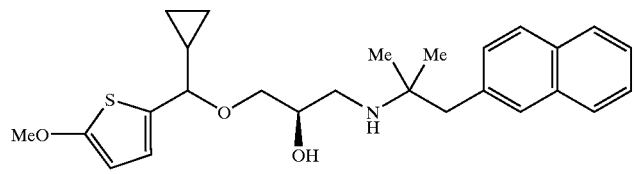 | ¹H-NMR(300MHz, δppm, CDCl₃) 7.82–7.76(3H, m), 7.65(1H, s), 7.47–7.45(2H, m), 7.27(1H, d, J=10.6Hz), 6.56(1H, dd, J=3.6, 1.8Hz), 6.01–5.99(1H, m), 4.05–3.95(1H, m), 3.86–3.83(3H, m), 3.72(1H, t, J=7.7Hz), 3.60–3.45(2H, m), 3.12–2.89(4H, m), 1.27–1.24(6H, m), 1.09–1.00(1H, m), 0.60–0.40(3H, m), 0.30–0.20(1H, m).<br>MS(ESI, m/z) 440(M + H)⁺. |
| Ex. 159 | 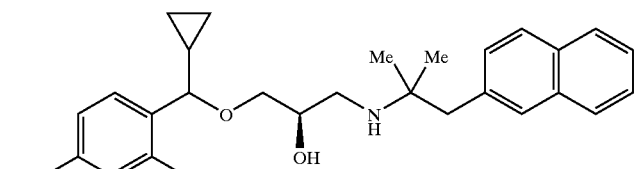 | ¹H-NMR(300MHz, δppm, CDCl₃) 7.82–7.73(3H, m), 7.61(1H, s), 7.47–7.40(2H, m), 7.31–7.27(2H, m), 6.51–6.43(2H, m), 4.15(1H, d, J=7.8Hz), 3.80–3.77(7H, m), 3.48–3.33(2H, m), 2.84–2.68(4H, m), 1.19–1.68(7H, m), 0.60–0.50(1H, m), 0.38–0.25(3H, m).<br>MS(ESI, m/z) 464(M + H)⁺. |

TABLE 23-continued

| Ex. | | $^1$H-NMR(300MHz, δppm, CDCl$_3$) |
|---|---|---|
| 160 | 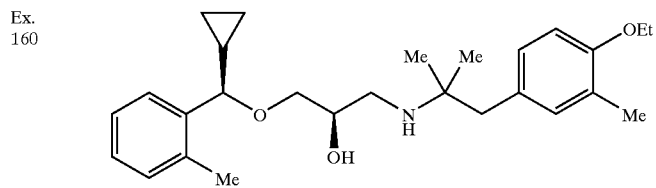 | 7.40–7.10(4H, m), 7.00–6.85(3H, m), 6.72(1H, d, J=8.7Hz), 4.09(1H, d, J=7.5Hz), 4.05–3.85(3H, m), 3.50–3.30(2H, m), 3.20–2.75(2H, m), 2.67(2H, s), 2.33(3H, s), 2.19(3H, s), 1.41–3H, t, J=6.9Hz), 1.25–1.00(7H, m), 0.65–0.10(4H, m). MS(ESI, m/z) 426(M + H)$^+$. |

EXPERIMENTAL EXAMPLES

The biological activity of the compound of the present invention was examined.

Experimental Example 1
Evaluation of Antagonistic Action on Calcium Receptor Using Reporter Gene Luciferase cDNA and human calcium receptor cDNA were transfected into a cell strain derived from rat adrenal and the transformed cells were cultured overnight in a medium (F12 medium containing 0.5% dialyzed horse serum and 0.25% dialyzed bovine fetal serum). The next day, a dimethyl sulfoxide solution containing a test compound at 0.01–100 mM was diluted 100-fold with the medium and added to the test compound group at 10 μl per well. A medium containing 50 mM calcium chloride was added to the control group at 10 μl per well, such that the final calcium concentration of the medium became 5 mM. A medium alone was added to the blank group. After culture for 4 hr, luciferase substrate (PicaGene LT-2.0, TOYO INK) was added and the luciferase activity was measured with a photoluminometer. The inhibitory rate (%) was calculated from the obtained measured values according to the following formula.

$$\text{Inhibitory rate (\%)} = 100 \; \frac{\text{measured value of compound group} - \text{measured value of blank group}}{\text{measured value of control group} - \text{measured value of blank group}} \times 100$$

Based on the results, the concentration (IC$_{50}$) showing 50% inhibitory rate was determined.

For reference, a compound of the above-mentioned formula [1-3] wherein R$^{11}$, R$^{12}$ and R$^{21}$ are hydrogen atoms and R$^{71}$ and R$^{72}$ in combination show —CH=CH—CH=CH—

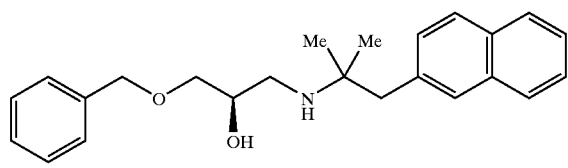

(Comparative Example 1) was also subjected to the testing. The results are shown in Table 24 and Table 25.

Experimental Example 2
PTH Secretion Promoting Action

The test compound was orally administered to 6 to 9-week-old male SD rats (Charles River Japan, Inc.) fasted for 20 hr, using a solvent (5% ethanol, 0.5% aqueous methyl cellulose solution) at a dose of 30 mg/5 ml/kg and 100 mg/5 ml/kg. A solvent alone was orally administered to the control group at a dose of 5 ml/kg. The blood was drawn from the tail vein immediately before and 0.5, 1, 2, 4, 6 hr after the administration of the test compound, and sera were obtained. The serum PTH concentration was measured using rat PTH (1-84) ELISA kit (Nohon Medi-Physics). The results of the serum PTH concentration before and 30 min and 4 hr after the administration of the test compound are shown in Table 24, and the results of the serum PTH concentration before and 30 min and 2 hr after the administration of the test compound of the 30 mg/5 ml/kg administration group are shown in Table 25.

Figure 2:
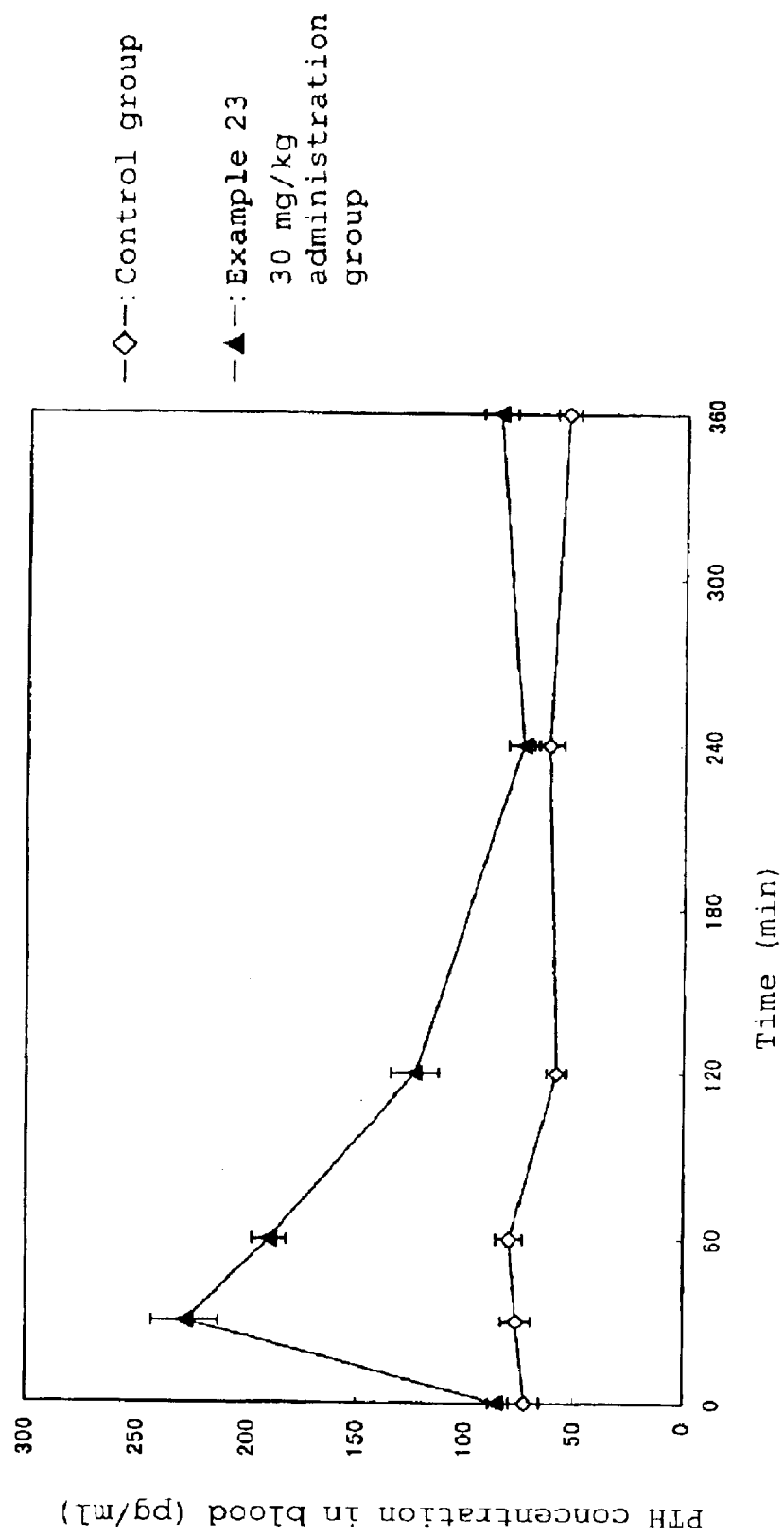
FIG. 2 shows the time-course changes of serum PTH concentration when 30 mg/kg of a compound of Example 23 was administered to rat.
Figure 3:
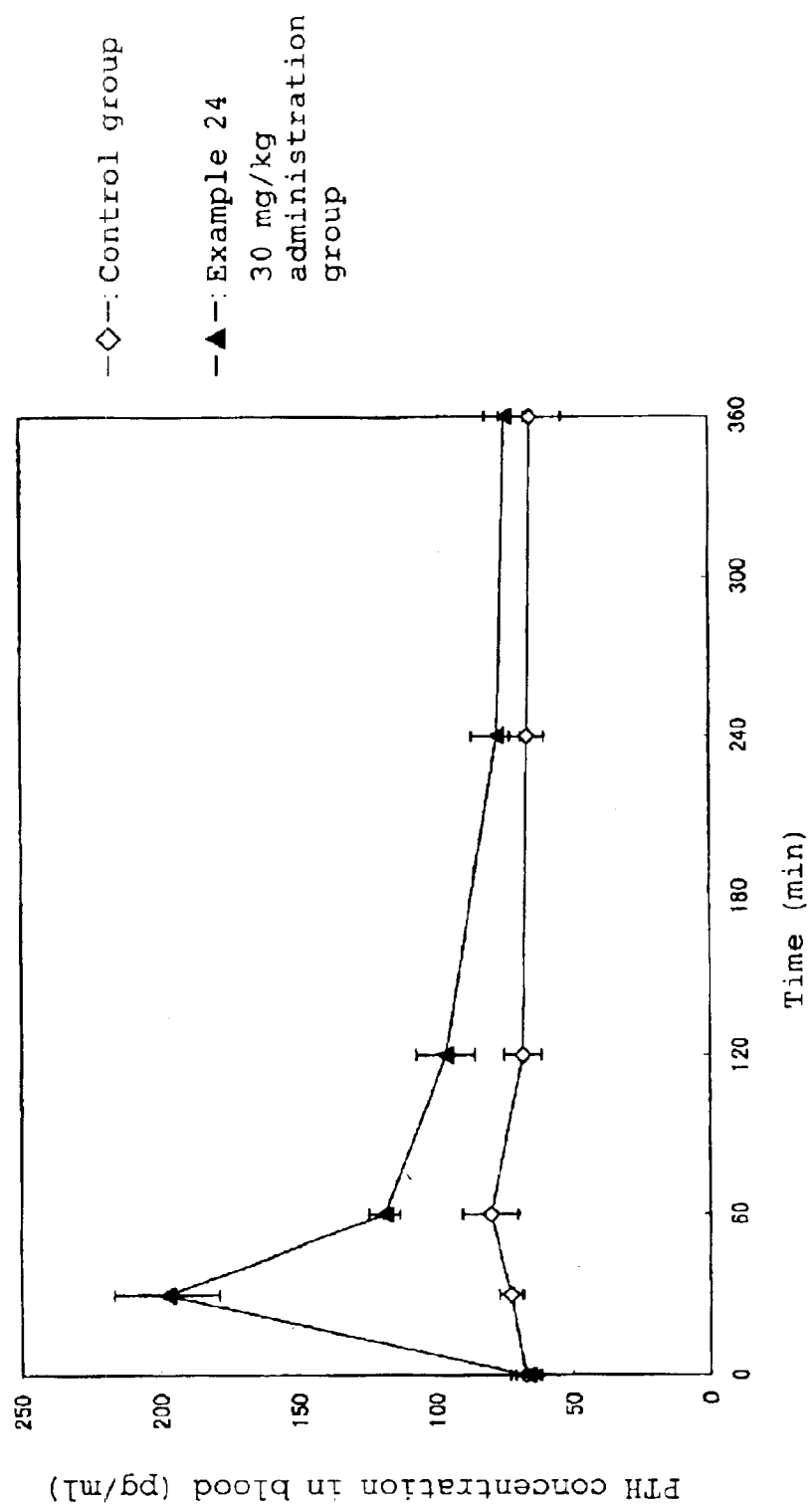
FIG. 3 shows the time-course changes of serum PTH concentration when 30 mg/kg of a compound of Example 24 was administered to rat.
Figure 4:
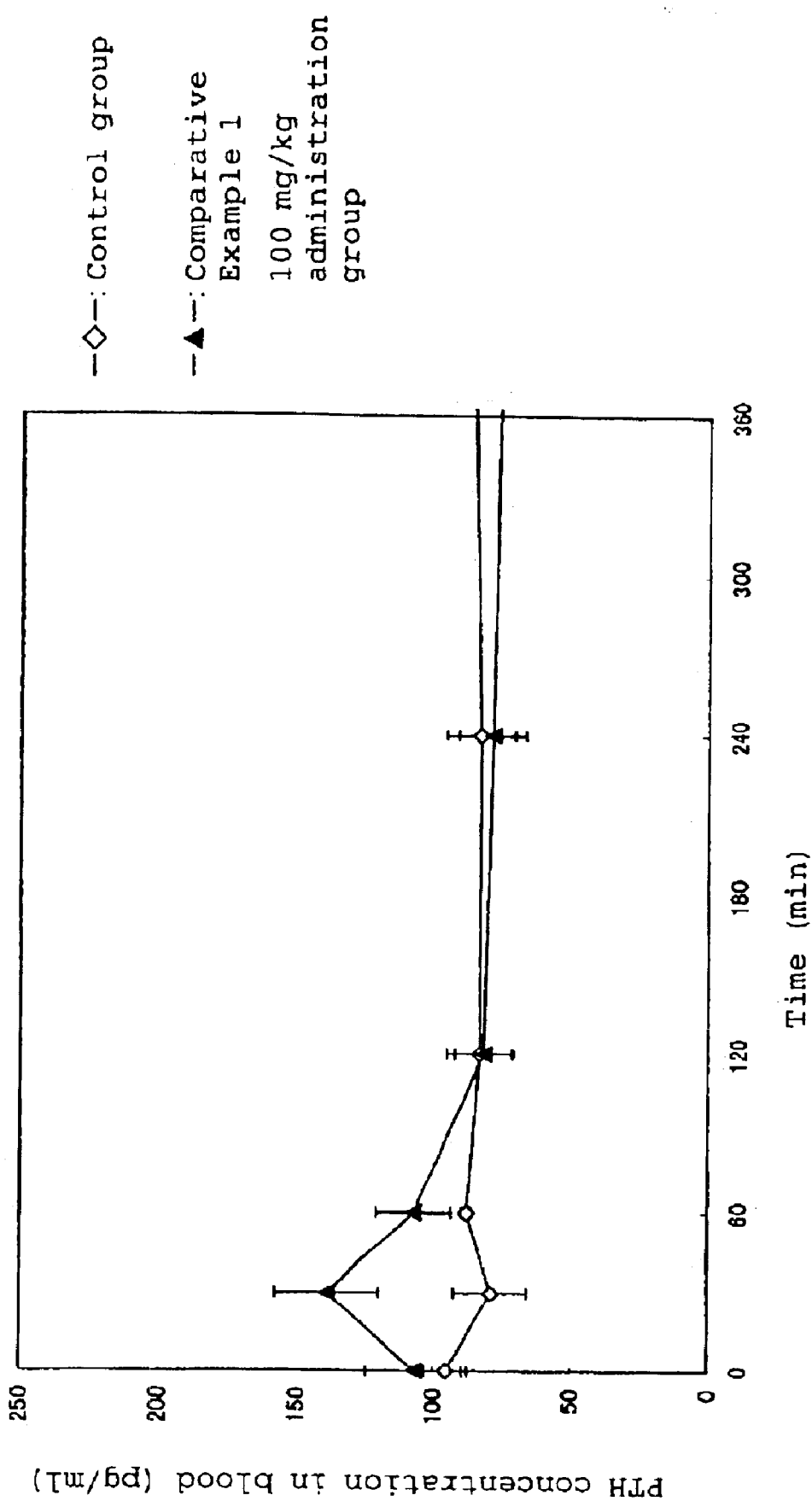
FIG. 4 shows the time-course changes of serum PTH concentration when 100 mg/kg of a compound of Comparative Example 1 was administered to rat.
Figure 5:
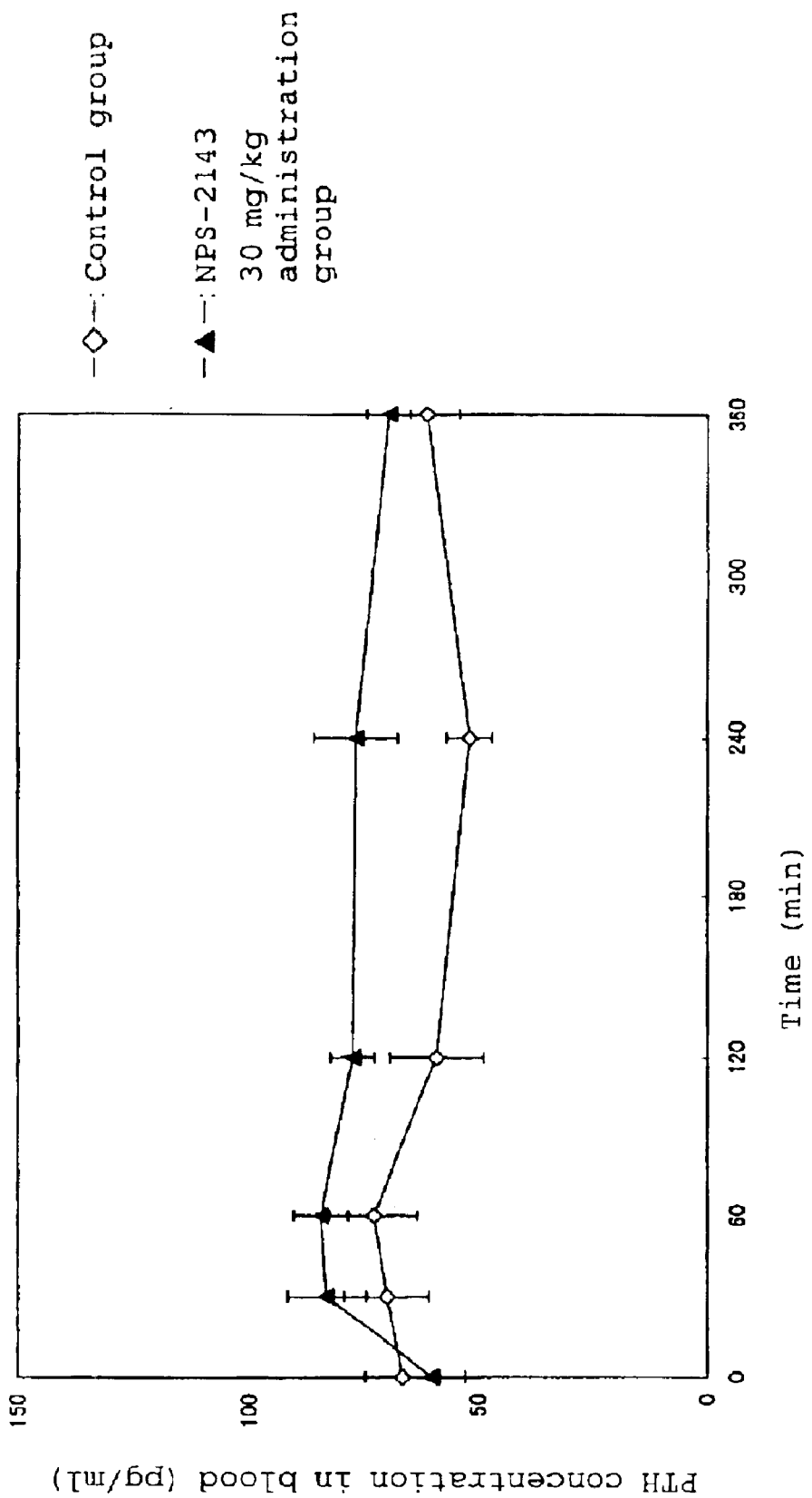
FIG. 5 shows the time-course changes of serum PTH concentration when 30 mg/kg of NPS-2143 was administered to rat.

In FIG. 1, FIG. 2 and FIG. 3, the time-course changes of the serum PTH concentration at the dose (30 mg/kg) of Example 22, Example 23 and Example 24 are shown. For reference, moreover, FIG. 4 shows the time-course changes of the serum PTH concentration at the dose of Comparative Example 1 (100 mg/kg), and FIG. 5 shows the time-course changes of the serum PTH concentration at the dose of NPS-2143 of 30 mg/kg.

TABLE 24

| | | serum PTH concentration (pg/ml) | | |
|---|---|---|---|---|
| | | Before administration | 30 min later | 240 min later |
| test compound | IC$_{50}$ (μM) | 30 mg/kg administration group (upper line) 100 mg/kg administration group (lower line) | | |
| Example 1 | 0.041 | 56.9 ± 9.4 | 141.5 ± 15.3 | 54.1 ± 7.7 |
| | | 55.8 ± 3.9 | 160.0 ± 13.8 | 58.3 ± 7.3 |
| Example 2 | 0.027 | 52.0 ± 3.4 | 148.4 ± 10.1 | 60.0 ± 5.8 |
| | | 68.9 ± 7.6 | 154.8 ± 17.1 | 85.8 ± 17.3 |
| Example 5 | 0.070 | 78.9 ± 11.8 | 155.6 ± 14.9 | 84.8 ± 12.3 |
| | | — | — | — |
| Example 22 | 0.059 | 62.2 ± 5.2 | 185.7 ± 10.0 | 73.4 ± 11.0 |
| | | — | — | — |
| Example 23 | 0.027 | 85.3 ± 3.6 | 228.3 ± 15.0 | 73.9 ± 6.9 |
| | | — | — | — |
| Example 24 | 0.022 | 66.5 ± 4.3 | 197.7 ± 18.9 | 77.5 ± 9.0 |
| | | — | — | — |
| Example 62 | 0.045 | 99.3 ± 43.6 | 259.2 ± 29.4 | 82.2 ± 9.9 |
| | | — | — | — |
| Comparative Example 1 | 0.56 | 107.1 ± 17.5 | 139.0 ± 18.8 | 78.9 ± 12.3 |

(— means unmeasured, mean ± S.E.)

TABLE 25

| test compound | IC$_{50}$ ($\mu$M) | serum PTH concentration (pg/ml) | | |
|---|---|---|---|---|
| | | Before administration | 30 min later | 120 min later |
| Example 80 | 0.064 | 44.3 ± 6.3 | 156.6 ± 15.3 | 76.1 ± 12.6 |
| Example 82 | 0.051 | 66.7 ± 5.0 | 121.9 ± 9.0 | 68.5 ± 11.4 |
| Example 95 | 0.029 | 105.8 ± 44.2 | 199.1 ± 25.8 | 80.4 ± 9.6 |
| Example 100 | 0.067 | 52.2 ± 4.4 | 130.1 ± 53.7 | 49.3 ± 4.4 |
| Example 105 | 0.049 | 38.3 ± 8.6 | 115.4 ± 20.0 | 74.3 ± 12.1 |
| Example 111 | 0.024 | 51.2 ± 12.8 | 236.3 ± 60.8 | 65.3 ± 6.4 |
| Example 127 | 0.133 | 65.0 ± 6.9 | 265.3 ± 22.3 | 75.2 ± 7.3 |

(- means unmeasured, mean ± S.E.)

Experimental Example 3
PTH Secretion Promoting Action

The test compound was orally administered to 4 to 6-week-old female Fisher rats (Charles River Japan, Inc.) fasted for 20 hr, using a solvent (5% ethanol, 0.5% aqueous methyl cellulose solution) at a dose of 30 mg/5 ml/kg. A solvent alone was orally administered to the control group at a dose of 5 ml/kg. The blood was drawn from the tail vein immediately before and 0.5, 1, 2, 4 hr after the administration of the test compound, and sera were obtained. The serum PTH concentration was measured using rat PTH (1-84) ELISA kit (Nohon Medi-Physics). The results of the serum PTH concentration before and 30 min and 4 hr after the administration of the test compound are shown in Table 26.

TABLE 26

| test compound | serum PTH concentration (pg/ml) | | |
|---|---|---|---|
| | Before administration | 30 min later | 240 min later |
| Example 58 | 179.2 ± 45.6 | 644.4 ± 65.2 | 394.1 ± 100.9 |
| Example 59 | 189.8 ± 90.9 | 313.4 ± 103.3 | 62.2 ± 10.3 |
| Example 62 | 82.9 ± 14.5 | 620.6 ± 34.2 | 100.1 ± 11.7 |

(mean ± S.E.)

When osteoporosis is to be treated by increasing the blood PTH concentration by inhibition of the action of calcium receptor, the compound to be used for this end should have at least the following properties.

(i) The compound has a sufficient antagonistic action on calcium receptors. In other words, the compound has a sufficiently low IC$_{50}$ value. In the specification of WO99/51241, it is described, "In general, a compound showing a low IC$_{50}$ value in the assay of calcium receptor inhibitor is a more superior compound. A compound showing an IC$_{50}$ value of not lower than 50 $\mu$M is considered to be inactive. A preferable compound shows an IC$_{50}$ value of not more than 10 $\mu$M, more preferably 1 $\mu$M, and most preferably not more than 0.1 $\mu$M."

(ii) Administration of the compound results in a sufficient increase in the blood PTH concentration.

(iii) The time-course concentrations in blood after administration of the compound are not sustainable. Desirably, the PTH concentration before administration is restored at 3, 4 hr after administration of the compound.

From the above-mentioned test results, the compound of the present invention clearly shows the above-mentioned characteristics.

As regards (i); As shown in Table 24 and Table 25, the IC$_{50}$ value of the compound of the present invention is not more than 1 $\mu$M, and the compound has a sufficient antagonistic action on calcium receptors. The compound of the present invention is considered to be preferable in view of the IC$_{50}$ value.

As regards (ii); As shown in Table 24–Table 26 and FIGS. 1–3, at 30 min later, the 30 mg/kg administration group showed a 2.0–3.0 times higher blood PTH concentration than that before administration, and the 100 mg/kg administration group showed a 2.2–3.6 times higher blood PTH concentration than that before administration, and the compound of the present invention has been confirmed to have a superior PTH secretion promoting action. In contrast, as shown in Table 24 and FIG. 4, at 30 min after administration, the compound of Comparative Example 1 only showed a 1.3 times higher blood PTH concentration even at the dose of 100 mg/kg. The compound was not found to have a superior PTH secretion promoting action, and cannot be expected to be a pharmaceutical product.

As regards (iii); As shown in Table 24–Table 26 and FIGS. 1–3, PTH secretion by the compound of the present invention reached a peak at 30 min after administration, sharply decreased thereafter and returned to the blood PTH concentration before administration in about 2–4 hr. It is clear that the compound of the present invention is superior from this aspect. In contrast, as a result of the reproductive test of NPS-2143 of the reference, the sustained secretion promoting action of NPS-2143 was confirmed (from FIG. 5).

INDUSTRIAL APPLICABILITY

As is clear from the above-mentioned Experimental Example 1, the compound of the formula [I] of the present invention has a superior calcium receptor antagonistic action. Accordingly, the compound is expected to be useful as a therapeutic drug of diseases accompanied by abnormal calcium homeostasis, such as osteoporosis, hypoparathyreosis, osteosarcoma, periodontal disease, bone fracture, steoarthrosis, chronic rheumatoid arthritis, Paget's disease, humoral hypercalcemia, autosomal dominant hypocalcemia and the like. As is clear from Experimental Examples 2 and 3, the compound of the present invention has a temporary PTH secretion promoting action. Accordingly, the compound is particularly useful as a therapeutic agent for osteoporosis.

This application is based on patent application Nos. 244536/2000 and 132879/2001 filed in Japan, the contents of which are hereby incorporated by reference.

What is claimed is:
1. A compound of the formula [I]

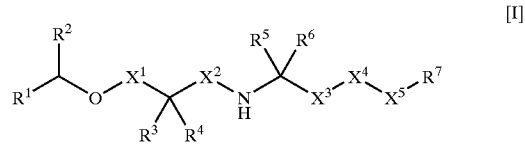

wherein
R$^1$ is aryl group or heteroaryl group wherein said aryl group and heteroaryl group are optionally substituted by 1 to 3 substituents selected from halogen atom, C$_{1-6}$ alkyl group, halo(C$_{1-6}$)alkyl group, hydroxy(C$_{1-6}$)alkyl group, C$_{1-6}$ alkoxy(C$_{1-6}$)alkyl group, hydroxyl group, C$_{1-6}$ alkoxy group, halo(C$_{1-6}$)alkoxy group, mercapto group, C$_{1-6}$ alkylthio group, C$_{1-6}$ alkylsulfanyl group, C$_{1-6}$ alkylsulfonyl group, aminosulfonyl group, C$_{1-6}$ alkylsulfamoyl group, di(C$_{1-6}$ alkylsulfamoyl group, carboxy group, ($C_{1-6}$ alkoxy)carbonyl group, $C_{1-7}$ acyl group, carbamoyl group, ($C_{1-6}$ alkyl)carbamoyl group, di($C_{1-6}$ alkyl)carbamoyl group, cyano group, nitro group, amino group, $C_{1-6}$ alkylamino group, di($C_{1-6}$) alkylamino group, $C_{1-7}$ acylamino group, $C_{1-3}$ alkylenedioxy group,

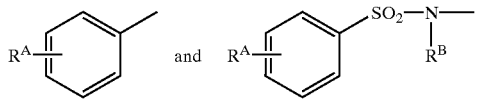

wherein $R^A$ is ($C_{1-6}$ alkoxy)carbonyl group or carboxy group, and $R^B$ is hydrogen atom or $C_{1-6}$ alkyl group;

$R^2$ is $C_{1-6}$ alkyl group wherein said $C_{1-6}$ alkyl group is optionally substituted by 1 to 3 substituents selected from halogen atom, hydroxyl group, $C_{1-6}$ alkoxy group, carboxy group, amino group, $C_{1-6}$ alkylamino group, di($C_{1-6}$ alkylamino group and oxo group, $C_{3-7}$ cycloalkyl group, $C_{2-6}$ alkenyl group, $C_{2-6}$ alkynyl group, aralkyl group, carboxy group, ($C_{1-6}$ alkoxy)carbonyl group or cyano group;

$R^3$ is hydrogen atom, $C_{1-6}$ alkyl group, hydroxyl group, $C_{1-6}$ alkoxy group, mercapto group, $C_{1-6}$ alkylthio group, carboxy group, ($C_{1-6}$ alkoxy)carbonyl group, ($C_{1-6}$ alkyl)carbamoyl group di($C_{1-6}$ alkyl)carbamoyl group, amino group, $C_{1-6}$ alkylamino group or di($C_{1-6}$)alkylamino group;

$R^4$ is hydrogen atom, $C_{1-6}$ alkyl group or $C_{1-6}$ alkenyl group, or $R^3$ and $R^4$ in combination form an oxo group;

$R^5$ and $R^6$ are the same or different and each is $C_{,1-6}$ alkyl group or $R^5$ and $R^6$ in combination form a cyclopropyl group together with the carbon atom they bind to;

$R^7$ is aryl group or heteroaryl group wherein said aryl group and heteroaryl group are optionally substituted by 1 to 3 substituents selected from halogen atom, $C_{1-6}$ alkyl group, halo($C_{1-6}$)alkyl group, hydroxy($C_{1-6}$)alkyl group, $C_{3-7}$ cycloalkyl group, hydroxyl group, $C_{1-6}$ alkoxy group, halo($C_{1-6}$)alkoxy group, carboxy group, ($C_{1-6}$ alkoxy)carbonyl group, nitro group, cyano group, $C_{1-6}$ alkylsulfonyloxy group, carbamoyl group and $C_{1-3}$ alkylenedioxy group;

$X^1$ is a single bond, $C_{1-6}$ alkylene group or $C_{2-6}$ alkynylene group wherein said $C_{1-6}$ alkylene group and $C_{2-6}$ alkynylene group are optionally substituted by $C_{1-6}$ alkyl group or oxo group;

$X^2$ is $C_{1-6}$ alkylene group wherein said $C_{1-6}$ alkylene group is optionally substituted by $C_{1-6}$ alkyl group or halo($C_{1-6}$)alkyl group;

$X^3$ is a single bond or $C_{1-6}$ alkylene group wherein said $C_{1-6}$ alkylene group is optionally substituted by hydroxyl group or oxo group;

$X^4$ and $X^5$ in combination form a single bond, methylene group, —NH—, oxygen atom, sulfur atom, —C(=O)—, —$CH_2NH$—, —$CH_2O$—, —$CH_2S$—, —$CH_2CO$—, —$NHCH_2$—, —$OCH_2$—, —$SCH_2$—, —$COCH_2$—, —CH=CH— or —C≡C—, a salt thereof, a solvate thereof or a prodrug thereof.

2. A compound of the formula [I']

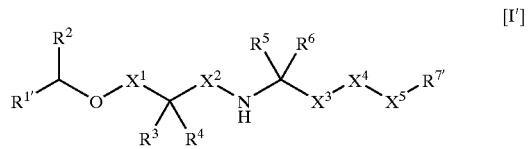

wherein $R^{1'}$ is aryl group or heteroaryl group wherein said aryl group and heteroaryl group are optionally substituted by 1 to 3 substituents selected from halogen atom, $C_{1-6}$ alkyl group, halo($C_{1-6}$)alkyl group, hydroxy($_{1-6}$)alkyl group, $C_{1-6}$ alkoxy($C_{1-6}$)alkyl group, hydroxyl group, $C_{1-6}$ alkoxy group, halo($C_{1-6}$)alkoxy group, mercapto group, $C_{1-6}$ alkylthio group, $C_{1-6}$alkylsulfanyl group, $C_{1-6}$ alkylsulfonyl group, aminosulfonyl group, $C_{1-6}$ alkylsulfamoyl group, di($C_{1-6}$)alkylsulfamoyl group, carboxy group, ($C_{1-6}$ alkoxy)carbonyl group, $C_{1-7}$ acyl group, carbamoyl group, ($C_{1-6}$ alkyl)carbamoyl group, di($C_{1-6}$ alkyl)carbamoyl group, cyano group, nitro group, amino group, $C_{1-6}$ alkylamino group, di($C_{1-6}$) alkylamino group and $C_{1-7}$ acylamino group;

$R^{7'}$ is aryl group or heteroaryl group wherein said aryl group and heteroaryl group are optionally substituted by 1 to 3 substituents selected from halogen atom, $C_{1-6}$ alkyl group, halo($C_{1-6}$)alkyl group, $C_{3-6}$ cycloalkyl group, hydroxyl group, $C_{1-6}$ alkoxy group, halo($C_{1-6}$) alkoxy group, carboxy group, ($C_{1-6}$ alkoxy)carbonyl group, nitro group, cyano group and $C_{1-6}$ alkylsulfonyloxy group; and $R^2$, $R^3$, $R^4$, $R^5$, $R^6$, $X^1$, $X^2$, $X^3$, $X^4$ and $X^5$ are same as defined in claim 1 respectively, a salt thereof, a solvate thereof or a prodrug thereof.

3. A compound of the formula [I"]

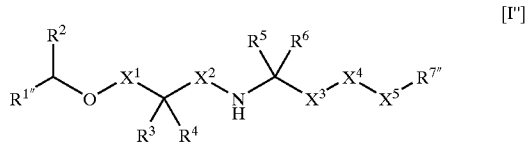

wherein $R^{1''}$ is aryl group or heteroaryl group wherein said aryl group and heteroaryl group are optionally substituted by 1 to 3 substituents selected from $C_{1-3}$ alkylenedioxy group,

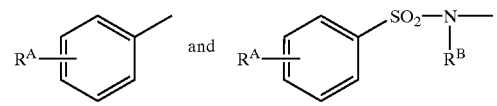

wherein $R^A$ is ($C_{1-6}$ alkoxy)carbonyl group or carboxy group and $R^B$ is hydrogen atom or $C_{1-6}$ alkyl group;

$R^{7'''}$ is aryl group or heteroaryl group wherein said aryl group and heteroaryl group are optionally substituted by 1 to 3 substituents selected from hydroxy($C_{1-6}$)alkyl group, carbamoyl group and $C_{1-3}$ alkylenedioxy group; and $R^2$, $R^3$, $R^4$, $R^5$, $R^6$, $X^1$, $X^2$, $X^3$, $X^4$ and $X^5$ are same as defined in claim 1 respectively, a salt thereof, a solvate thereof or a prodrug thereof.

4. A compound of the formula [I-2]

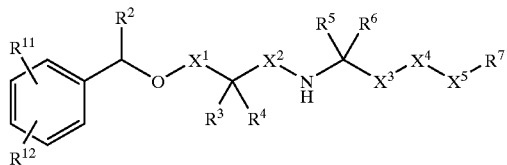

[I-2]

wherein $R^{11}$ and $R^{12}$ are the same or different and each is hydrogen atom, halogen atom, $C_{1-4}$ alkyl group, hydroxy($C_{1-6}$)alkyl group, $C_{1-6}$alkoxy($C_{1-6}$)alkyl group, hydroxyl group, $C_{1-4}$ alkoxy group, cyano group or nitro group, or $R^{11}$ and $R^{12}$ in combination form a $C_{1-3}$ alkylenedioxy group, $R^{21}$ is $C_{1-4}$ alkyl group wherein said alkyl group is optionally substituted by $C_{1-4}$ alkoxy group, $C_{3-5}$ cycloalkyl group, $C_{2-4}$ alkenyl group, or aralkyl group, and $R^3$, $R^4$, $R^5$, $R^6$, $R^7$, $X^1$, $X^2$, $X^3$, $X^4$ and $X^5$ are same as defined in claim 1 respectively, a salt thereof, a solvate thereof or a prodrug thereof.

5. The compound of claim 4, which is represented by the formula [I-3]

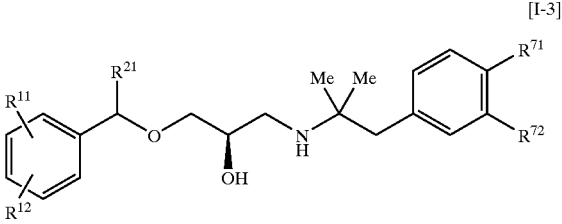

[I-3]

wherein $R^{71}$ and $R^{72}$ are the same or different and each is hydrogen atom, $C_{1-4}$ alkyl group or $C_{1-4}$ alkoxy group, or in combination form a —CH=CH—CH=CH— or $C_{1-3}$ alkylenedioxy group, and $R^{11}$, $R^{12}$ and $R^{21}$ are same as defined in claim 4 respectively, a salt thereof, a solvate thereof or a prodrug thereof.

6. The compound of claim 5, wherein $R^{11}$ and $R^{12}$ are the same or different and each is hydrogen atom, chlorine atom, methyl group, hydroxymethyl group, hydroxyl group, methoxy group, cyano group or nitro group, or $R^{11}$ and $R^{12}$ in combination form a methylenedioxy group, and $R^{21}$ is optionally branched $C_{1-4}$ alkyl group or $C_{3-5}$ cycloalkyl group, a salt thereof, a solvate thereof or a prodrug thereof.

7. The compound of claim 6, wherein $R^{21}$ is methyl group, ethyl group, cyclopropyl group or cyclobutyl group, a salt thereof, a solvate thereof or a prodrug thereof.

8. The compound of claim 7, wherein $R^{11}$ is hydrogen atom, $R^{12}$ is methyl group, methoxy group or hydroxymethyl group, or $R^{11}$ and $R^{12}$ in combination form a methylenedioxy group, and $R^{21}$ is methyl group or cyclopropyl group, a salt thereof, a solvate thereof or a prodrug thereof.

9. The compound of claim 8, wherein $R^{21}$ is cyclopropyl group, a salt thereof, a solvate thereof or a prodrug thereof.

10. The compound of claim 9, wherein $R^{71}$ and $R^{72}$ in combination form —CH=CH—CH=CH—, a salt thereof, a solvate thereof or a prodrug thereof.

11. The compound of claim 9, wherein $R^{71}$ and $R^{72}$ are groups selected from $C_{1-4}$ alkyl group and $C_{1-4}$ alkoxy group, a salt thereof, a solvate thereof or a prodrug thereof.

12. The compound of claim 1, which is selected from (2R)-1-[1,1-dimethyl-2-(naphthalen-2-yl)ethylamino]-3-[(cyclopropyl)(2-methoxyphenyl)methoxy]propan-2-ol, (2R)-1-[1,1-dimethyl-2-(naphthalen-2-yl)ethylamino]-3-[(cyclopropyl)(2-methylphenyl)methoxy]propan-2-ol, (2R)-1-[1,1-dimethyl-2-(naphthalen-2-yl)ethylamino]-3-[(cyclopropyl)(phenyl)methoxy]propan-2-ol, (2R)-1-[1,1-dimethyl-2-(naphthalen-2-yl)ethylamino]-3-[1-(2-methoxyphenyl)ethoxy]propan-2-ol, (2R)-1-[1,1-dimethyl-2-(naphthalen-2-yl)ethylamino]-3-[1-(2-methylphenyl)ethoxy]propan-2-ol, (2R)-1-[1,1-dimethyl-2-(naphthalen-2-yl)ethylamino]-3-[1-(2-methoxyphenyl)propoxy]propan-2-ol, (2R)-1-[1,1-dimethyl-2-(naphthalen-2-yl)ethylamino]-3-[1-(2-cyanophenyl)ethoxy]propan-2-ol, (2R)-1-[1,1-dimethyl-2-(naphthalen-2-yl)ethylamino]-3-[1-(3-methoxyphenyl)ethoxy]propan-2-ol and (2R)-1-[1,1-dimethyl-2-(naphthalen-2-yl)ethylamino]-3-[1-(3-methylphenyl)ethoxy]propan-2-ol, a salt thereof, a solvate thereof or a prodrug thereof.

13. (2R)-1-[1,1-Dimethyl-2-(naphthalen-2-yl)ethylamino]-3-[(cyclopropyl)(2-hydroxymethylphenyl)methoxy]propan-2-ol, a salt thereof, a solvate thereof or a prodrug thereof.

14. A pharmaceutical composition comprising the compound of claim 1, a salt thereof, a solvate thereof or a prodrug thereof as an active ingredient.

15. A calcium receptor antagonist comprising the compound of claim 1, a salt thereof, a solvate thereof or a prodrug thereof as an active ingredient.

16. A therapeutic agent for osteoporosis comprising the compound of claim 1, a salt thereof a solvate thereof or a prodrug thereof as an active ingredient.

* * * * *